(12) United States Patent
Glessner et al.

(10) Patent No.: US 10,844,434 B2
(45) Date of Patent: Nov. 24, 2020

(54) METHODS TO DIAGNOSE AND TREAT ATTENTION-DEFICIT, HYPERACTIVITY DISORDER (ADHD)

(71) Applicant: The Children's Hospital of Philadelphia, Philadelphia, PA (US)

(72) Inventors: Joseph Glessner, Mullica Hill, NJ (US); Josephine Elia, Penllyn, PA (US); Hakon Hakonarson, Malvern, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 15/063,482

(22) Filed: Mar. 7, 2016

(65) Prior Publication Data

US 2017/0009296 A1 Jan. 12, 2017

Related U.S. Application Data

(63) Continuation of application No. 13/776,662, filed on Feb. 25, 2013, now abandoned, which is a continuation-in-part of application No. PCT/US2011/048993, filed on Aug. 24, 2011.

(60) Provisional application No. 61/376,498, filed on Aug. 24, 2010, provisional application No. 61/466,657, filed on Mar. 23, 2011.

(51) Int. Cl.
| | | |
|---|---|---|
| C12Q 1/6883 | (2018.01) | |
| C12Q 1/6876 | (2018.01) | |
| A61K 31/454 | (2006.01) | |

(52) U.S. Cl.
CPC .......... *C12Q 1/6883* (2013.01); *A61K 31/454* (2013.01); *C12Q 1/6876* (2013.01); *C12Q 2600/136* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | |
|---|---|---|
| 9,884,057 B2 | 2/2018 | Hakonarson et al. |
| 2004/0116505 A1 | 6/2004 | Krauss et al. |
| 2005/0233321 A1 | 10/2005 | Hess et al. |
| 2007/0244152 A1 | 10/2007 | Lowy |
| 2007/0299113 A1 | 12/2007 | Kalvinsh et al. |
| 2009/0176740 A1 | 7/2009 | Phillips, II |
| 2010/0120628 A1 | 5/2010 | Belouchi et al. |
| 2010/0143921 A1 | 6/2010 | Sadee et al. |
| 2010/0216734 A1 | 8/2010 | Barlow et al. |
| 2011/0269688 A1 | 11/2011 | Hakonarson et al. |
| 2012/0149677 A1 | 6/2012 | Dudkin et al. |
| 2013/0143867 A1 | 6/2013 | Fogel et al. |
| 2013/0203814 A1 | 8/2013 | Glessner et al. |
| 2013/0225623 A1 | 8/2013 | Buxbaum et al. |
| 2014/0303243 A1 | 10/2014 | Hakonarson et al. |
| 2014/0315992 A1 | 10/2014 | Hakonarson et al. |
| 2016/0032390 A1 | 2/2016 | Hakonarson et al. |
| 2017/0083664 A1 | 3/2017 | Hakonarson et al. |
| 2017/0087139 A1 | 3/2017 | Hakonarson et al. |
| 2017/0087140 A1 | 3/2017 | Hakonarson et al. |
| 2017/0087141 A1 | 3/2017 | Hakonarson et al. |
| 2018/0110767 A1 | 4/2018 | Hakonarson et al. |

FOREIGN PATENT DOCUMENTS

| | | |
|---|---|---|
| WO | WO 2003/054167 | 7/2003 |
| WO | WO 2005/094801 | 10/2005 |
| WO | 2007104035 A1 | 9/2007 |
| WO | WO 2008/136995 | 11/2008 |
| WO | WO 2009/105718 | 8/2009 |
| WO | WO 2010/057112 | 5/2010 |
| WO | 2012027491 A1 | 3/2012 |
| WO | 2013006857 A1 | 1/2013 |
| WO | 2016022324 A1 | 2/2016 |
| WO | 2016205348 A1 | 12/2016 |

OTHER PUBLICATIONS

Lesch, K-P. et al.,"Genome-wide copy number variation analysis in attention-deficit/hyperactivity disorder: association with neuropeptide Y gene dosage in an extended pedigree", Molecular Psychiatry. Mar. 23, 2010 (Published online), vol. 16, pp. 491-503.
Stergiakouli, E. and Thapar, A., "Fitting the pieces together: current research on the genetic basis of attention-deficit/hyperactivity disorder (ADHD)", Neuropsychiatric Disease and Treatment. Aug. 23, 2010, vol. 6, pp. 551-560.
Jones, G. et al., "Exploratory dose-escalation study of NFC-1 in ADHD adolescents with glutamatergic gene network variants.", 62nd Annual Meeting. AACAP, Oct. 2015.
Hirouchi, Masaaki, "Role of metabotropic glutamate receptor subclasses in modulation of adenylyl cyclase activity by a nootropic NS-105" European Journal of Pharmacology 387: 9-17 (2009).
International Search Report and Written Opinion issued in PCT/US2016/050559 dated Feb. 16, 2017.
Malykh, Andrei G. et al: "Piracetam and piracetam-like drugs: from basic science to novel clinical application to CNS disorders" Drugs, 70(3): 287-312 (2010).
Tarver, J. et al.: "Attention-deficit hyperactivity disorder (ADHD): an updated review of the essential facts" Child: Care, Health and Development, 40(6):762-774 (2014).
Akhundian, J., Iranian Journal of Pediatrics, 2001, 11(2): 32-36; abstract only.
Database Geo [online] NCBI, "Illumina HumanHap550 Genotyping Beadchip v1," Feb. 5, 2008, XP002717448.
Elia, J. et al., "Rare Structural Variants Found in Attention-Deficit Hyperactivity Disorder are Preferentially Associated with Neurodevelopmental Genes," Molecular Psychiatry, 2010, 15(6): 637-646, and supplementary table s1 (p. 1-7).

(Continued)

*Primary Examiner* — Carla J Myers
(74) *Attorney, Agent, or Firm* — Kathleen D. Rigaut; Howson & Howson LLP

(57) ABSTRACT

Compositions and methods for the detection and treatment of ADHD are provided.

5 Claims, 18 Drawing Sheets

(56) References Cited

OTHER PUBLICATIONS

Extended European Search Report in copending European Patent Application No. 11820610.1, dated Jan. 2, 2014.
Forero, D. et al., "Candidate Genes Involved in Neural Plasticity and the Risk for Attention-Deficit Hyperactivity Disorder: a Meta-Analysis of 8 Common Variants," Journal of Psychiatry and Neuroscience, 2009, 34(5): 361-366.
International Search Report for PCT/US2011/048993, dated Jan. 27, 2012.
Klopocki et al., Annual Review Genomics Human Genetics, 2011, 12:53-72.
Krom, M. et al., "A Common Variant in DRD3 Receptor is Associated with Autism Spectrum Disorder," Biological Psychiatry, 2009, 65(7): 625-630.
Neale, B. et al., "Genome-Wide Association Scan of Attention Deficit Hyperactivity Disorder," American Journal of Medical Genetics Part B: Neuropsychiatric Genetics, 2008, vol, 147B, pp. 1337-1344.
O'Connor et al., "Metabotropic Glutamate Receptor 7: At the Interface of Cognition and Emotion," Eur J Pharacol., Apr. 2, 2010;639: 123-131 [Abstract].
Semenova et al., "The Effects of the mGluR5 Antagonist MPRP and the mGluR2/3 Antagnonist LY341495 on Rats'Performance in the 5-choice Serial Reaction Time Task," Neuropharmacology, 2007, 52(3):863-872 [Abstract].
File history for U.S. Appl. No. 13/776,662, filed Feb. 25, 2013.
Hadley et al. "The impact of metabotropic glutamate receptor and other gene family interaction networks on autism" Nature Communications, 5:4074 (2014).
Manning, M. et al. "Array-based technology and recommendations for utilization in medical genetics practice for detection of chromosomal abnormalities" Genetics in Medicin, 12(11):742-745 (2010).
Miller, Caroline, "How Anxiety Leads to Disruptive Behavior: kids who seem oppositional are often severely anxious" Child Mind Institute: Anxiety and Disruptive Behavior in Children, pp. 1-3. https://childmind.org/article/how-anxiety-leads-to-disruptive-behavior/) visited Nov. 27, 2017.
Murck, et al. "Taking Personalized Medicine Seriously:Biomarker Approaches in Phase IIb/III Studies in Major Depression and Schizophrenia" Innov clin Neurosci 12(3-4 Suppl A):26S-40S (2015).
Nagamitsu, S. et al. "Upregulated GABA inhibitory function in ADHD children with child behavior checklist-dysregulation profile: 123I-iomazenil SPECT study" Frontiers in Psychiatry 6: 84 (Jun. 2015).
Nakagawa et al. "Effects of a newly synthesized pyroglutaminanide defivative, LAM-105 on learning and memory in rats." Japanaese J. Pharmacol 46(Suppl.) Abstract O-258 (1988).
Nakagawa et al. "A pyroglutaminanide defivative, LAM-105, improved the deficit in a spatial memory task induced by transient forebrain ischemia in rats." Japanaese J. Pharmacol 46(Suppl. 1) Abstract P-491 (1990).
Navarro, J.F. et al. "P.1.d.006 Effects of LY379268, a selective agonist of mGlu2/3 receptors, on isolation-induced aggression in male mice" European Neuropsychopharmacology, 18: S252 (2008).
National Institute of Mental Health "Anxiety Disorder" NIH Publication No. 09 3879 (2009).
National Institute of Mental Health "Tourette Syndrome" NIH Publication No. 12-2163 (2012).
Niswender, C.M. and Conn, P.J. "Metabotropic Glutamate Receptors: Physiology, Pharmacology and Disease" Ann. Rev. Pharmacol. Toxicol. 50:295-322 (2010).
Nock, M. K., et la. "Prevalence, Subtypes, and Correlates of DSM-IV Conduct Disorder in the National Comorbidity Survey Replication" Psychol Med., 36(5):699-710 (2006).
Nomura et al. "Nefiracetam facilities hippocampal neurotransmissin by a mechanism independent of the poracetam and aniracetam action." Brain Research, 870: 157-162 (2000).

Ogasawara et al. "Involvement of Cholinergic and GABAergic Systems in the Reversal of Memory Disruption by NS-105, a Cognition Enhancer." Pharmacology Biochemistry and Behavior, 64(1): 41-52 (1999).
Oka, et al. "A novel cognition enhancer NS-105 modulates adenylate cyclase activity through metabotropic glutamate receptors in primary neuronal culture" Nauny-Schmiedeberg's Arch Pharmacol, 356:189-196 (1997).
Oka, M. et al. "Involvement of metabotropic glutamate receptores in Gi- and Gs-dependent modulation of adenylate cyclase activity induced by a novel cognition enhancer NS-105 in rat brain" Brain Research, 754: 121-130 (1997).
Palucha, et al.: "Metabotropic glutamate receptor ligands as possible anxiolytic and antidepressant drug", Pharmacology and Therapeutics, 115(1):116-147 (2007).
Park, S. et al. "Associatation between the GRM7 rs3792452 polymorphism and attention deficit hyperactiveity disorder in a Korean sample" Behavioral and Brain Functions, 9:1 (2013).
Park, S. et al. "The Metabotropic Glutamate Receptor Subtype 7 rw 3792452 Polymorphism is Associated with the Response to Methylphenidate in Children with Attention-Deficit/Hyperactivity Disorder" J. Child Adolesc. Phychopharmacoloty 24(4): 223-227 (2014).
The Research Unit on Pediatric Psychopharmacology Anxiety Study Group "Fluvoxamine for the Treatment of Anxiety Disorders in Children and Adolescents" N Engl J Med, vol. 344(17):1279-1285 (2001).
Sansone, S., et al. "Psychometric Study of the Aberrant BEhavior Checklist in Fragile X Syndrome and Implications or Targeted Treatment" J Autism Dev Disord, 42(7):1377-1392 (2012).
Schneider, M. et al. "Psychiatric Disorders From Childhood to Adulthood in 22q11.2 Deletion Syndrome: Results from the International Consortium on Brain Behavior in 22q11.2 Deletion Syndrom" Am J. Pshychiatry 171(6):627-639 (2014).
Shaffer, L. et al. "American College of Medical Genetics guideline on the cytogenetic evaluation of the individual with the developmental delay or mental retardation" Genetics in Medicine, 7(9):650-654 (2005).
Shannon et al. "Cytoscape: A Software Environment for Integrated Models of Biomolecular Interaction Networks," Genome Research, 2498-2504 (2003).
Shimidzu et al."Effect of a novel cognition enhancer NS-105 on learned helplessness in rats: Possible involvement of GABA B receptor up-regulation after repeated treatement" European Journal of Pharmacology 338:225-232 (1997).
Singer et al."Baclofen treatment in Tourette syndrome." Neurology 56: 599-604 (2001).
Steele, et al. "Remission Versus Response as the Goal of Therapy in ADHD: A New Standard for the Field?" Clinical Therapeutics, 28(11):1892-1908 (2006).
Stofanko, M., et al. "Simple, Rapid and Inexpensive Quantitative Fluorescent PCT Method for Detection of Microdeletion and Microduplication Syndromes" PLOS ONE, 8(4): e61328 (2013).
Toteja, N., et al. "Prevalence and correlates of antipsychotic polypharmacy in children and adolescents receiving antipsychotic treatment" Int J Neuropsychopharmacol., 17(7):1095-1105 (2014).
Van Ameringen, M. et al. "Anticonvulsants in Anxiety Disorders" CPA-Bull. de l'APC (2003) pp. 9-13.
Wang et al. "PennCNV: An integrated hidden Markov model designed for high-resolution copy number variation detection in whole-genome SNP genotyping data" Genome Research 17: 1665-1674 (2007).
Wang and Bucan "Copy Number Variation Detection via High-Density SNP Genotyping." Cold Spring Harbor Protocalls, 3(6): 1-6 (2008).
Waschbusch, D. A., et al. "Development and Validation of the Conduct Disorder Rating Scale" Assessment, 14(1):65-74 (2007).
Wigal, S. B., et al. "NWP06, an Extended-Release Oral Suspension of Methylphenidate, Improved Attention-Deficit/Hyperactivity Disorder Symptoms Compared with Placebo in a Labratory Classroom Study" Journal of Child and Adolescent Psychopharmacology, 23(1):3-10 (2013).

(56) References Cited

OTHER PUBLICATIONS

Winblad, "Piracetam: A Review of Pharmacological Properties and Clinical Uses" CNS Drug Reviews, 11(2):169-182 (2005).
Winnicka, et al. "Piracetam—An Old Drug with Novel Properties?" Acta Poloniae Pharmaceutica—Drug Research, 62(5):405-409 (2005).
Wittmann, Marion et al: "Activation of Group III mGluRs Inhibits GABAergic and Glutamatergic Transmission in Substantia Nigra Pars Reticulata" Journal of Neurophysiology, 1960-1968 (2001). Journal of Neurophysiology.
Zavadenko et al. "Atomoxetine and piracetam in the treatment of attention deficit hyperactivity disorder in children" ZH Nevrol Psikhiatr IM S S Korsakova, 108(7):abstract (2008).
"Fasoracetam: LAM 105, NS 105" Drugs R&D, 2(2): 135-136 (1999).
Akutagava-Martins, et al. "Glutamatergic Copy Number Variants and Their Role in Attention-Deficit/Hyperactivity Disorder" Am J Med Genet Part B. 165B:502-509 (2014).
Aman, M.G. "Annotated Biography on the Aberrant Behavior Checklist (ABC)." Unpublished Manuscript. Columbus, OH: The Ohio State University (2010).
Baker, K. and Vorstman, J. "Is there a core neuropsychiatric phenotype in 22q11.2 deletion syndrome" Curr Opin Neurol, 25:131-137 (2012).
Bloch, Michael et al: "Recent advances in Tourette syndrome," Current Opinion in Neurology, 24(2):119-125 (2011).
Caporino, et al. "Defining Treatment Response and Remission in Child Anxiety: Signal Detection Analysis Using Pediatric Anxiety Rating Scale" J Am Acad Child Adolesc Psychiatry, 52(1):57-67 (2013).
Cohen, S., et al. "Clinical Assessment of Tourette Syndrome and Tic Disorders" Neurosci Biobehavb Rev., 37(6):997-1007 (2013).
Corkum, P. "Actigraphy and Parental Ratings of Sleep in Children with Attention-Deficit/Hyperactivity Disorder (ADHD)" Sleep, 24(3):303-312 (2001).
Declaration of Hakon Hakonarson, MD, PhD dated Apr. 12, 2018, filed Apr. 16, 2018 in U.S. Appl. No. 15/258,969.
Declaration of Hakon Hakonarson, MD, PhD dated Apr. 12, 2018, filed Apr. 16, 2018 in U.S. Appl. No. 15/258,977.
Declaration of Hakon Hakonarson, MD, PhD dated Mar. 8, 2017.
Dietrich, Andrea et al: "The Tourette International Collaborative Genetics (TIC Genetics) study, finding the genes causing Tourette syndrome: objectives and methods", European Child and Adolescent Psychiatry, 24(2):141-151 (2014).
Ebell, M. H. "Diagnosis of Anxiety Disorders in Primary Care" Am Fam Physician, 78(4):501-502 (2008).
Elia, et al. "Genome-wide copy number variation study associates metabotropic glutamate receptor gene networks with attention deficit hyperactivity disorder" Nat Genet., 44(1):78-84 (2011).
Elia, J. et al. "Genome-wide copy number variation study associates metabotropic glutamate receptor gene netwarks with attention deficit hyperactivity disorder" Nat Genet., 44(1):78-84 (2015).
Ercan, E. S., et al. "Risperidone in the treatment of conduct disorder in preschool children without intellectual disability" Child and Adolescent Psychiatry and Mental Health, 5:10 (2011).
Firth, H. V. "22q11.2 Duplication" Gene Reviews—NCBI Bookshelf (2013).
Fistova, et al. "Study specific effects of nootropic drugs on glutamate receptors in the rat brain" Eksp Klin Farmakol. 74(1):abstract (2011).
Forkmann, T., et al."The clinical global impression scale and the influence of patient or staff perspective on outcome" BMC Psychiatry, 11:83 (2011).
Gasparini et al. "Allosteric Modulaators for mGlu Receptors" Current Neuropharmacology, 5:187-194 (2007).
Gerevich, J. et al. "The generalizability of the Buss-Perry Aggression Questionnaire" Int. J. Meth. Psychiatr. Res. 16(3): 124-136 (2007).
Ghelardini, et al. "DM235 (Sunifiram): a Novel Nootropic with Potential as a Cognitive Enhancer," Naunyn-Schmiedeberg's Archives of Pharmacology, 365:419-426 (2002).
Goonman, et al. "Interpreting ADHS Rating Scale Scores: Linking ADHD Rating Scale Scores and CGI Levels in Two Randomized Controlled Trials of Lisdexamfetamine Dimesylate in ADHD" Primary Psychiartry, 17(3):44-52 (2010).
Gregory, Karen J. et al: "Pharmacology of metabotropic glutamate receptor allosteric modulators: structural basis and therapeutics potential for CNS disorders", Progress in Molecular Biology and Translational Science, 115: 61-121 (2013).
Gualtieri, et al. "Design and Study of Piracetam-like Nootropics, Controversial Members of the Problematic Class of Cognition-Enhancing Drugs" Current Pharmaceutical Design, 8:125-138 (2002).
Halperin, J. M., et al. "Reliability, Validity, and Preliminary Normative Data for the Children's Aggression Scale-Teacher Version" J. Am. Acad. Child Adolesc. Psychiatry 42(8): 965-971 (2003).
Hamelin and Lehmann Effects of putative cognition enhancers on the NMDA receptor by [3H]MK801 binding, European Journal of Pharmacology 281: R11-R13 (1995).
Harty, S.C. et a. "Adolescents with Childhood ADHD and Comorbid Disruptive Behavior Disorders: Aggression, Anger, and Hostility" Child Psychiatry Hum. Dev. 40(1): 85-97 (2009).
Hellings, et al. "The Overt Aggression Scale for Rating Aggression in Outpatient Youth with Autistic Disorder: Preliminary Findings" J of Neuropsychiatry and Clinical Neurosciences, 17:29-35 (2005).
Henrichsen, et al. "Copy number variants, diseases and gene expression" Human Molecular Genetics 18(1):R1-R8 (2009).
Hidalgo, et al. "An effect-size analysis of pharmacologic treatments for generalized anxiety disorder" Journal of Psychopharmacology, 21(8):864-872 (2007).
Hirouchi et al. "Role of metabotropic glutamate receptor subclasses in modulation of adenylyl cyclase activity by a nootropic NS-105" European Journal of Pharmacology, 387:9-17 (2000).
Hodgins et al., "Adolescents with conduct disorder: does anxiety make a difference?" The J. of Forensic Psychiatric and Psychology (2011 ), vol. 22(5), pp. 669-691.
International Search Report and International Written Opinion for PCT/US2016/037596, dated Sep. 16, 2016.
International Search Report and Written Opinion issued in PCT/US2016/050573 dated Dec. 21, 2016.
International Search Report and Written Opinion issued in PCT/US2016/050580 dated Dec. 20, 2016.
International Search Report and Written Opinion issued in PCT/US2016/050581 dated Dec. 21, 2016.
James, A. C. "Prescribing antipsychotics for children and adolescents" Advances in psychiatric treatment, 16:63-75 (2010).
Jonas, et al. "The 22q11.2 Deletion Syndrome as a Window into Complex Neuropsychiatric Disorders Over the Lifespan" Biol Psychiatry, 75(5):351-360 (2014).
Kam, H.J., et al. "High-Resolution Actigraphic Analysis of ADHD: A Wide Range of Movement Variability Observation in Three School Courses—A Pilot Study" Healthc Inform Res, 17(1):29-37 (2011).
Kelleher III et al. "High-Throughput Sequencing of mGluR Signaling Pathway Genes Reveals Enrichment of Rare Variants in Autism" PLos ONE, 7(4):e35003 (2012).
Kendler, Kenneth S. et al: "Familial Influences on Conduct Disorder Reflect 2 Genetic Factors and 1 Shared Environmental Factor", JAMA Psychiatry, 70(1): 78.
Leigh, M. et al. "A Randomized Double-Blind, Placebo-Controlled Trial of Minocycline in Children and Adolescents with Fragile X Syndrome" J. Dev Behav Pediatr, 34(3):147-155 (2013).
Malykh et al. "Piracetam and Piracetam-Like Drugs: From Basic Science to Novel Clinical Applications to CNS Disorders" Drugs 70(30):287-312 (2010).
International Search Report and International Written Opinion for PCT/US2016/050559, dated Sep. 16, 2017.
Addington, A. et al. "Annual Research Review: Impact of advances in genetics in understanding developmental psychopathology" J. Child Psychol. Psychiast (2012) vol. 53(5) 510-518.
Aevi Genomic Medicine, Aevi Genomic Medicine Announces Top-Line Results from Placebo-Controlled ASCEND Trial (Parts A & B) of AEVI-001 in Children with ADHD, News Release, https://

(56) References Cited

OTHER PUBLICATIONS aevigenomicmedicine.gcs-web.com/news-releases/news-release-details/aevi-genomic-medicine-announces-top-line-results-placebo, Jan. 2, 2019.
Auerbach, B. D. et al. "Mutations causing syndromic autism define an axis of synaptic pathophysiology" Nature, 480(7375):63-8 (2011).
Childress, A. et al. "Current Investigational Drugs for the Treatment of Attention-Deficit/Hyperactivity Disorder" Expert Opinion on Investigational Drugs, 2016, vol. 25(4):463-474.
Clarke, R. A. et al. "Tourette Syndrome and Klippel-Feil Anomaly in a Child with Chromosome 22q11 Duplication" (2009) Case Reports in Medicine ID 361518 pp. 1-5.
Cooper, G. M. et al. "Systematic assessment of copy number variant detection via genome-wide SNP genotyping" nature genetics 2008, 40(10):1199-1203.
Elia, J., et al. "Fasoracetam in adolescents with ADHD and glutamatergic gene network variants disrupting mGluR neurotransmitter signaling." Nature Communications. (Jan. 16, 2018), vol. 9, Issue 4, pp. 1-9. (Year 2018).
Fewtrell, MS, et al. "Hirschsprung's disease associated with a deletion of chromosome 10 (q11.2q21.2): a further link with the neurocristopathies?" J Med Genet 1994: 31:325-327.
Jarrett, M. A. et al. "A conceptual review of the comorbidity of attention-deficit/hyperactivity disorder and anxiety: Implications for future research and practice" Clinical Psychology Review, 28:1266-1280 (2008).
Jones, G. et al. "Exploratory dose-escalation study of NFC-1 in ADHD adolescents with glutamatergic gene network variants" 62nd Annual Meeting AACAP, 2015, poster.
Karayiorgou, M. et al. "22q11.2 microdeletions: linking DNA structural variation to brain dysfunction and schizophrenia" Nature Reviews—Neuroscience, 2010, vol. 11:402-416.
Lo-Castro, A., et al. "ADHD and genetic syndromes." Brain and Development. (2011), vol. 33, pp. 456-461. (Year: 2011).
Office Action issued in Canadian Application No. 2,807,505 dated May 7, 2018.
Rizzo et al. "Clinical Pharmacology of Comorbid Attention Deficit Hyperactivity Disorder in Tourette Syndrome" Int. Rev. Neurobiol, Chapter 14, 415-444 (2013).
Turgay, A. "Treatment of Comorbidity in Conduct Disorder with Attention-Deficit Hyperactivity Disorder (ADHD)" Essent. Psychopharmacol., 6(5):277-290 (2005).
U.S. National Library of Medicine. "Phase I Single Dose, Open-Label Pharmacokinetic Study and Single-Blind, Placebo-Controlled Dose Escalation Study of NFC-1 in Adolescents With Attention Deficit Hyperactivity Disorder (NFC1-GREAT)." Clinical Trials.gov Identifier: NCT02286817. Nov. 10, 2014. (Year: 2014).

Figure 1A
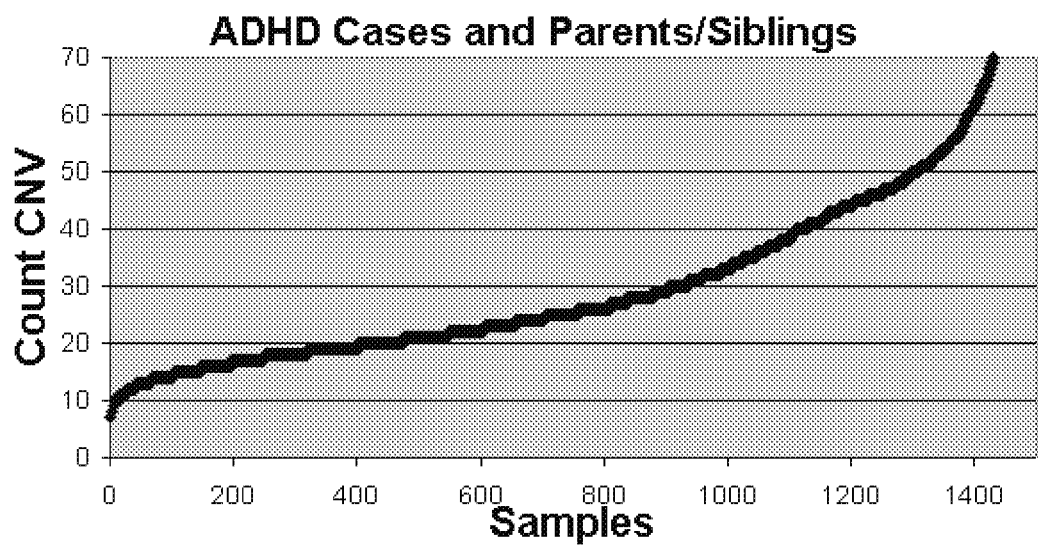
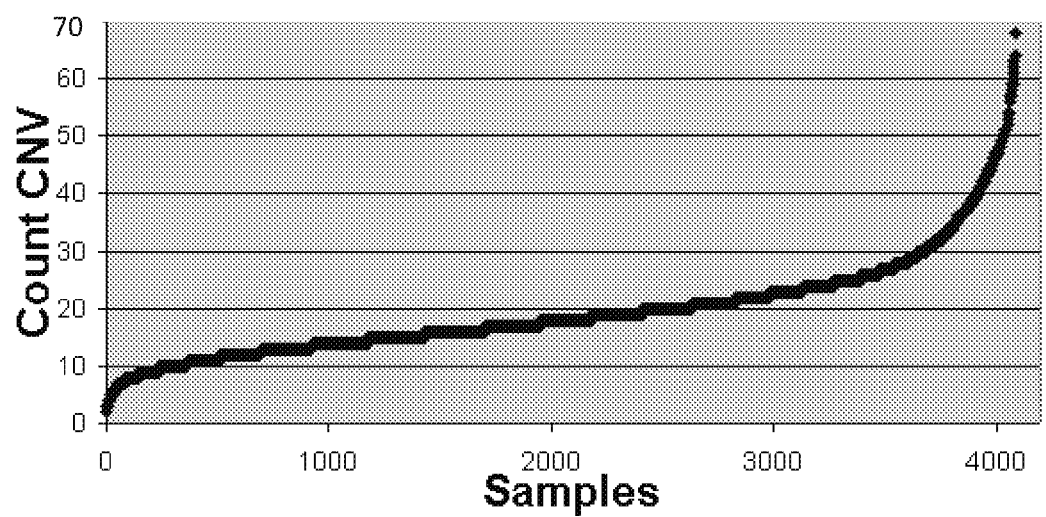
Figure 1B

METHODS TO DIAGNOSE AND TREAT ATTENTION-DEFICIT, HYPERACTIVITY DISORDER (ADHD)

This application is a continuation of U.S. application Ser. No. 13/776,662 filed Feb. 25, 2013, which is a continuation in part of PCT/US2011/048993 filed Aug. 24, 2011 which in turn claims priority to U.S. Provisional Applications 61/376,498 and 61/466,657 filed Aug. 24, 2010 and Mar. 23, 2011 respectively, the entire contents of each being incorporated by reference as though set forth in full.

FIELD OF THE INVENTION

This invention relates to the fields of genetics and the diagnosis of attention deficit hyperactivity disorder (ADHD). More specifically, the invention provides compositions and methods useful for the diagnosis and treatment of ADHD.

BACKGROUND OF THE INVENTION

Several publications and patent documents are cited through the specification in order to describe the state of the art to which this invention pertains. Each of these citations is incorporated herein by reference as though set forth in full.

Attention Deficit Hyperactivity Disorder (ADHD) is a common neuropsychiatric disorder with heritability estimates ranging from 30 to 90% (Derks, et al. 2008; Wood, et al. 2008; Haberstic, et al. 2008). Most neurodevelopmental disorders have been resistant to the genome wide association (GWA) approach, although recent progress has been made in autism (Glessner, et al. 2009; Derks, et al. 2008; Wod, et al. 2008; Haberstic, et al. 2008; Wang, et al. 2009). GWA studies have been reported in ADHD utilizing a cohort of 958 parent-child trios recruited through the International Multicentre ADHD Genetics (IMAGE) study. Results of these studies did not report any association at genome-wide significance level (Franke, et al. 2009; Neale, et al. 2008). Using quantitative measures of ADHD, Lasky-Su and colleagues recently reported nominal evidence from a PBAT analysis of tagging SNPs located at CDH13 (rs6565113) and GFOD1 (rs552655) (Lasky-Su, et al. 2008). A SNP in strong linkage disequilibrium with rs6565113 impacting CDH13 was also reported in a GWA study of an independent sample of ADHD adults (Lesch, et al. 2008). The applicants reported previously on copy number variation (CNV) loci observed in the first 335 ADHD cases we recruited (Elia, et al. 2009). While none of the CNV loci detected in that study met criteria for significance, it is noteworthy that one family was observed to have a GRM5 deletion impacting all three affected children, inherited from their affected father. A GRM7 deletion in one family with ADHD was additionally detected (Elia, et al. 2009). CNVs of metabotropic glutamate receptors (mGluR) in addition to the discovery of the NK3 gene in ADHD have suggested new therapeutic approaches to the treatment of ADHD.

The development of improved accurate diagnostic tests for this disorder based on associated genetic alterations is highly desirable. Such tests would facilitate conclusive diagnosis and provide avenues for the development of therapeutic agents having efficacy for the treatment of ADHD.

SUMMARY OF THE INVENTION

In accordance with the present invention, methods are provided for the diagnosis and treatment of ADHD. An exemplary method entails detecting the presence of at least one CNV in a target polynucleotide wherein if said CNV(s) is/are present, said patient has an increased risk for developing ADHD.

In one aspect of the present invention, a method for detecting a propensity for developing attention deficit hyperactivity disorder (ADHD) in a patient in need thereof is provided. An exemplary method entails detecting the presence of at least 1, 2, 3, 4, 5, 6, 10, 20, 30 or all of the SNP containing nucleic acid in a target polynucleotide, said SNP being informative of the presence of an ADHD associated copy number variation (CNV), wherein if said SNP is present, said patient has an increased risk for developing ADHD, wherein said SNP containing nucleic acid is provided in Table 13.

In another embodiment of the invention a method for identifying agents which alter neuronal signaling and/or morphology is provided. Such a method comprises providing cells expressing at least one nucleic acid comprising the ADHD associated CNVs of the invention, (step a); providing cells which express the cognate wild type sequences which lack the CNV (step b); contacting the cells from each sample with a test agent and analyzing whether said agent alters neuronal signaling and/or morphology of cells of step a) relative to those of step b), thereby identifying agents which alter neuronal signaling and morphology. In a preferred embodiment the test agent modulates metabotropic glutamate receptor (mGluR) gene activity. In another embodiment the test agent is selected from a group consisting of an mGluR positive allosteric modulators (PAM) (e.g., mGluR5 PAM, mGluR7 PAM), an mGluR negative allosteric modulator (NAM) (e.g., mGluR2/3 NAM), and a tachykinin-3/neurokinin-3 receptor (TAC3/NK3R) antagonist. In another embodiment, the test agent is selected from the group consisting of ADX63365, ADX50938, ADX71149, ADX48621, AMN082, 1-(hetero)aryl-3-aminopyrrolidine derivatives (e.g. those provided in U.S. Patent Application Publication No. 2008/0300266), LY341495, GSK1144814, and SB223412. Methods of treating ADHD patients via administration of test agents identified using the methods described herein in patients in need thereof are also encompassed by the present invention. The invention also provides at least one isolated ADHD related SNP-containing nucleic acid selected from the group listed in Table 13. In one embodiment, a multiplex SNP panel containing all of the informative SNPs from Table 13 is provided. Such SNP containing nucleic acids which indicate the presence of ADHD associated CNV(s) may optionally be contained in a suitable expression vector for expression in neuronal cells. Alternatively, they may be immobilized on a solid support. In yet another alternative, the panel may be provided in silico.

According to yet another aspect of the present invention, there is provided a method of treating ADHD in a patient determined to have at least one prescribed single nucleotide polymorphism indicative of the presence of an ADHD-associated copy number variation, as described herein below, by administering to the patient a therapeutically effective amount of at least one member of the piracetam family of nootropic agents. This method provides a test and treat paradigm, whereby a patient's genetic profile is used to personalize treatment with therapeutics targeted towards specific neurophysiological defects found in individuals exhibiting ADHD. Such a test and treat model may benefit up to 50% of patients with ADHD with greater efficacy and fewer side effects than non-personalized treatment. Thus, any of the patients exhibiting an alteration in glutaminergic signaling can be tested for the presence of such a genetic alteration and then treated with the appropriate pharmaceutical such as the agents listed above.

BRIEF DESCRIPTION OF THE DRAWINGS

FIGS. 1A-B. A graphical distribution of CNV calls per individual cases (1A) compared to controls (1B).

DETAILED DESCRIPTION OF THE INVENTION

Figure 2:
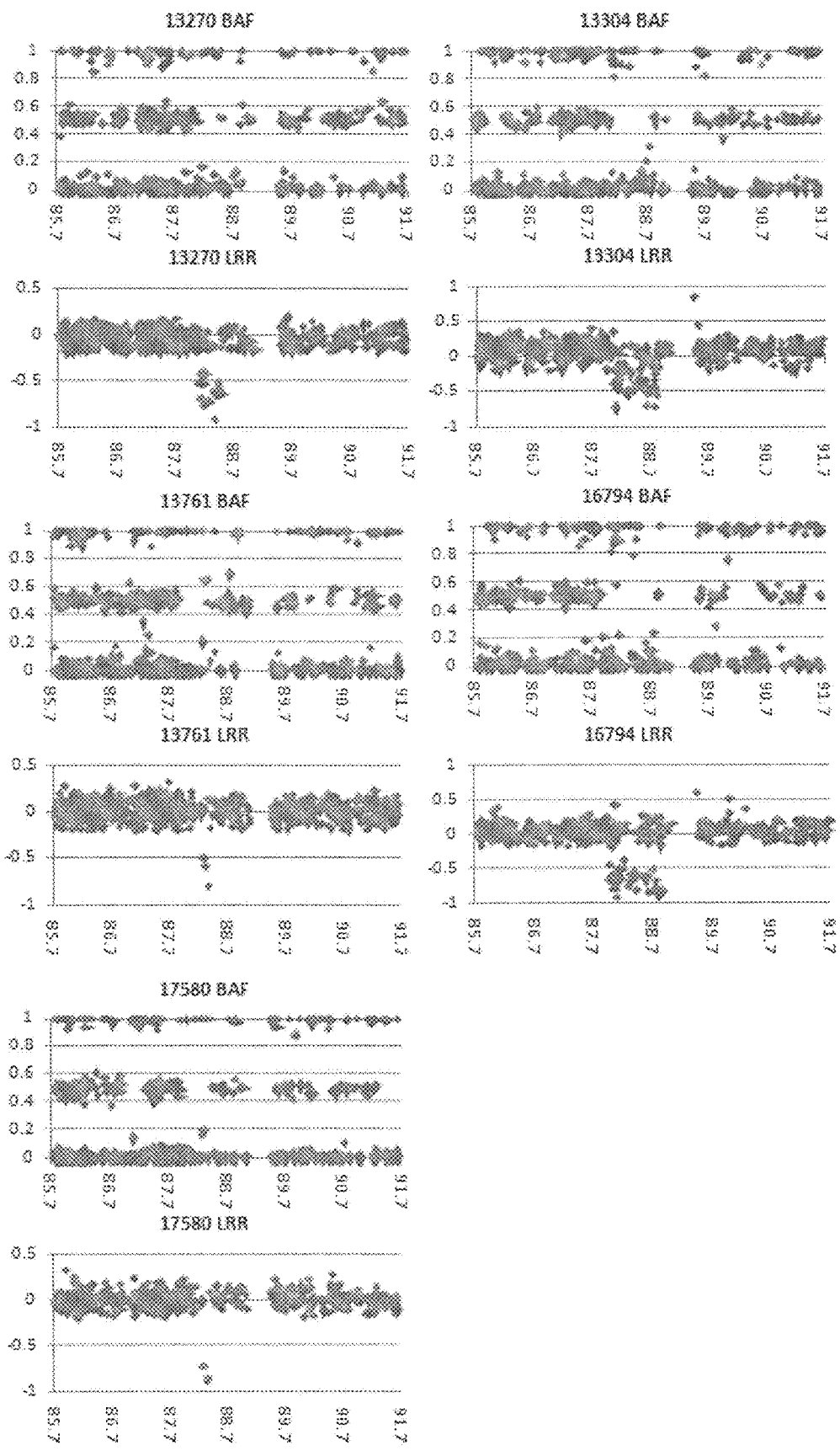
FIG. 2. A graphical display of the Normalized SNP Level Perlegen 600K Data. The X axis shows base pair position in Megabases on chromosome 11. Raw SNP Level Data Showing GRM5 Deletion in five samples from IMAGE Perlegen 600K Data Normalized by Adapted PennCNV-Affy Protocol. Genotype data termed B-allele frequency (BAF) and intensity data termed Log R Ratio (LRR) plotted.
Figure 3A:
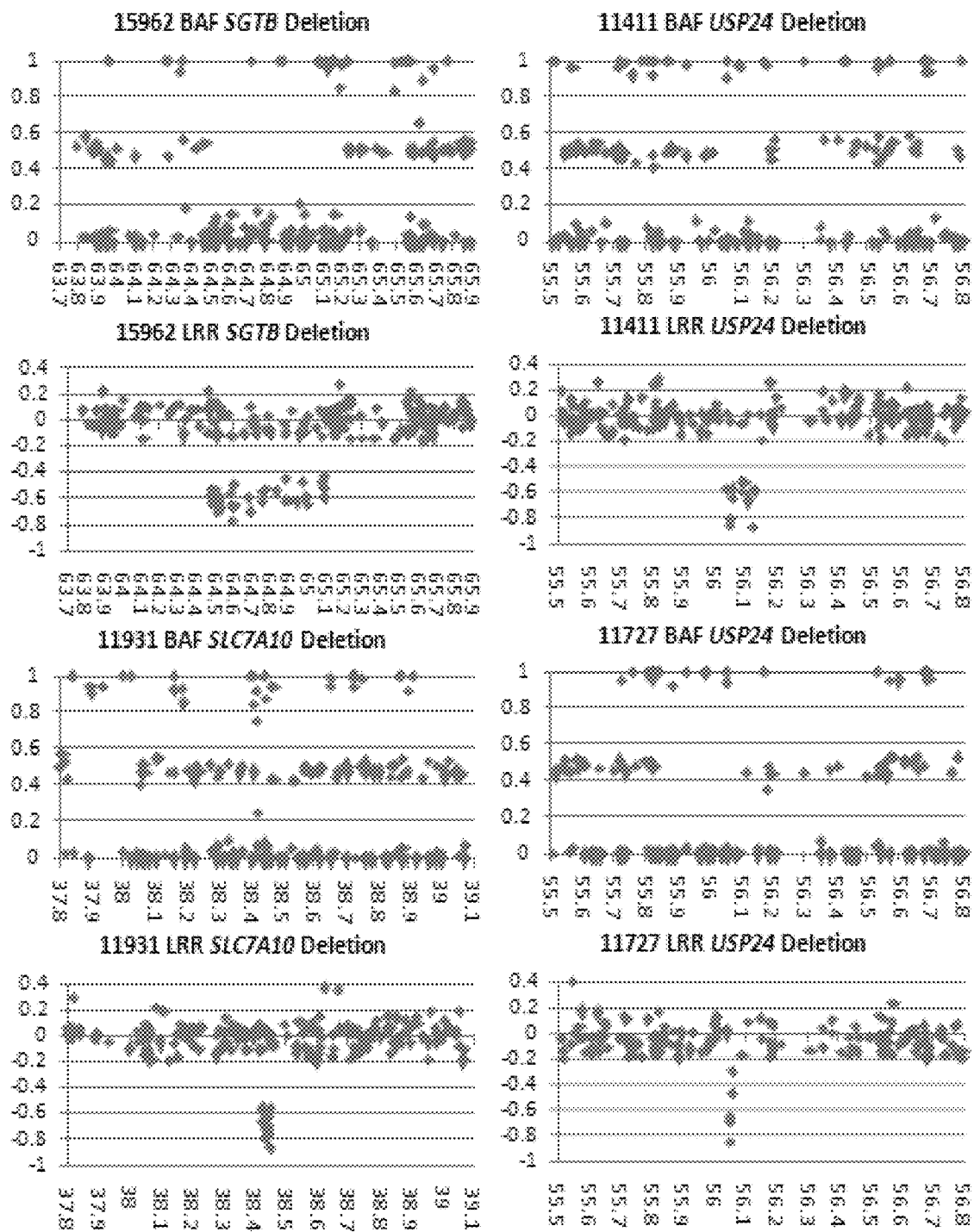
FIGS. 3A-F. Graphs of the full SNP-Level data: 3A-C) Normalized Perlegen 600K data, 3D-E) Normalized Illumina 1M PUWMa data, and 3F) Normalized Affymetrix 5.0 IMAGE II data.
Figure 3B:
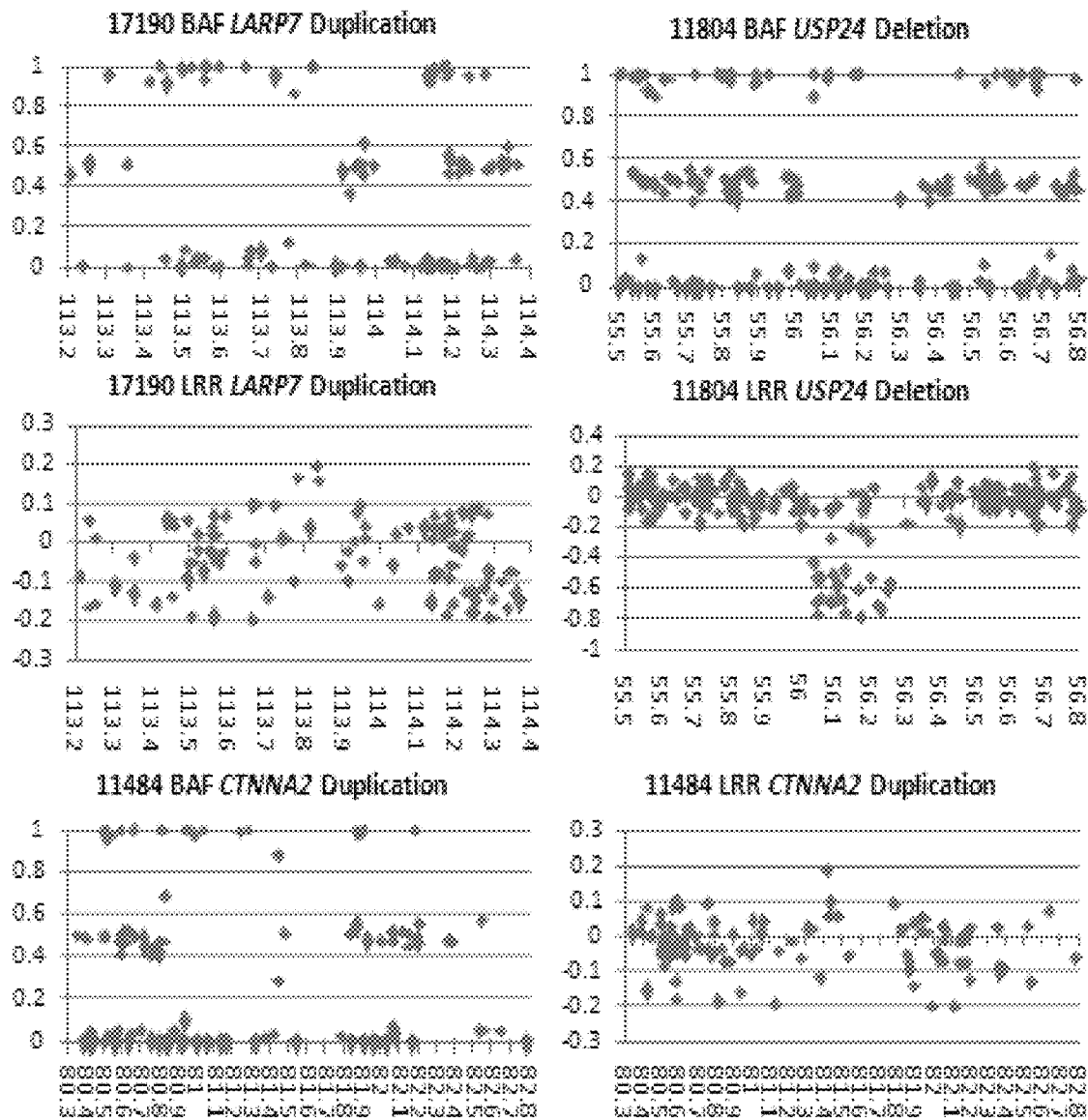
Figure 3C:
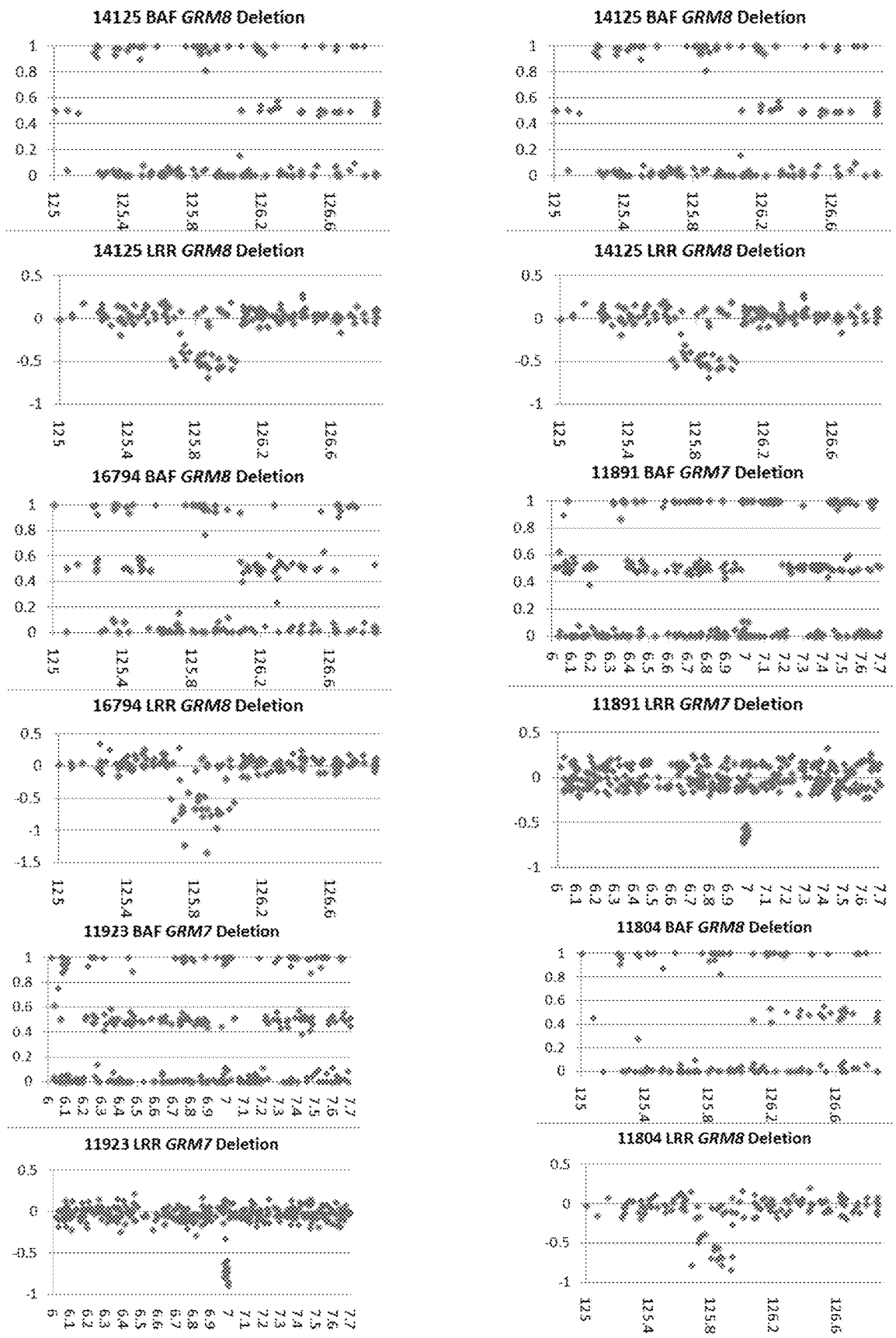
Figure 3D:
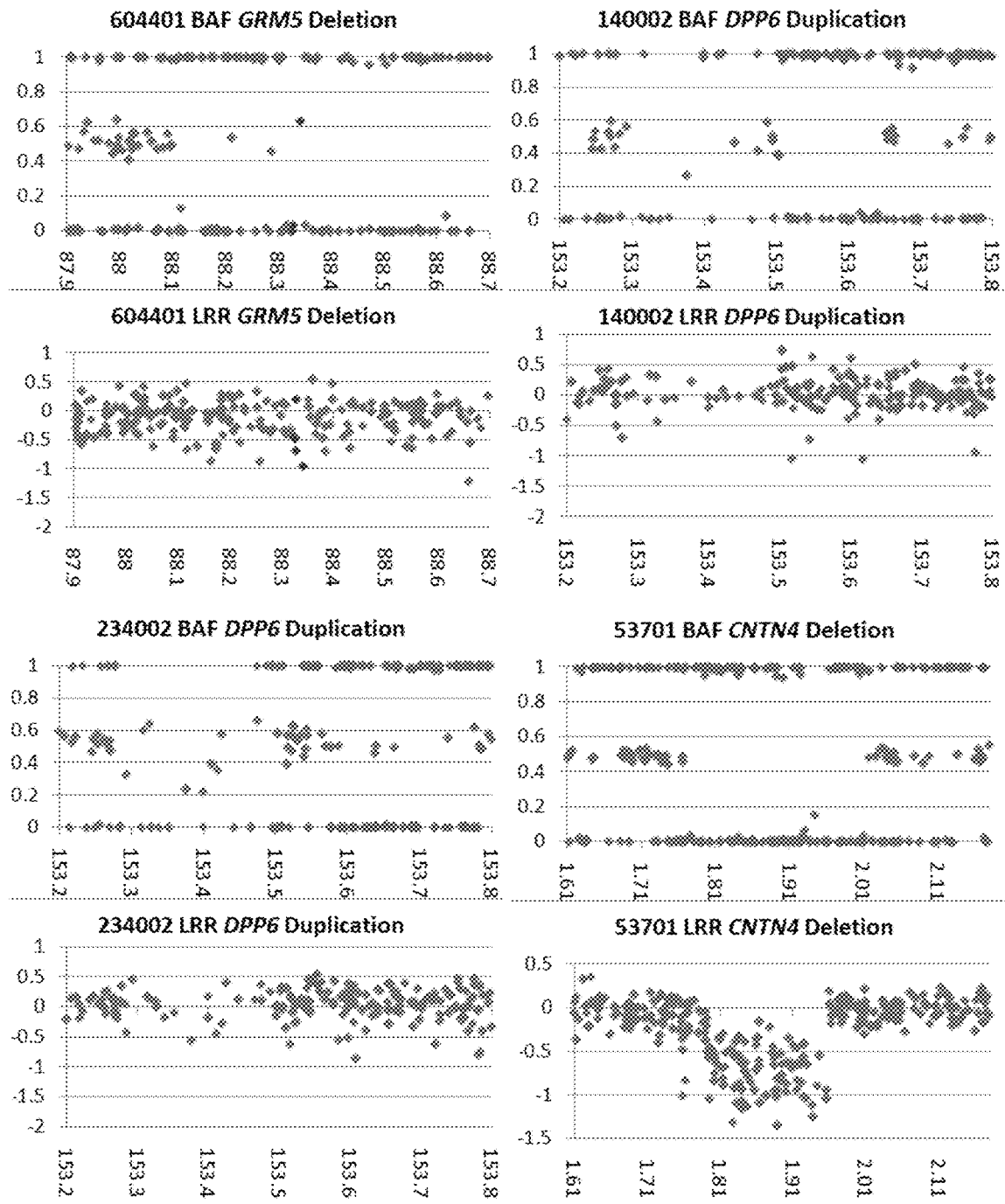
Figure 3E:
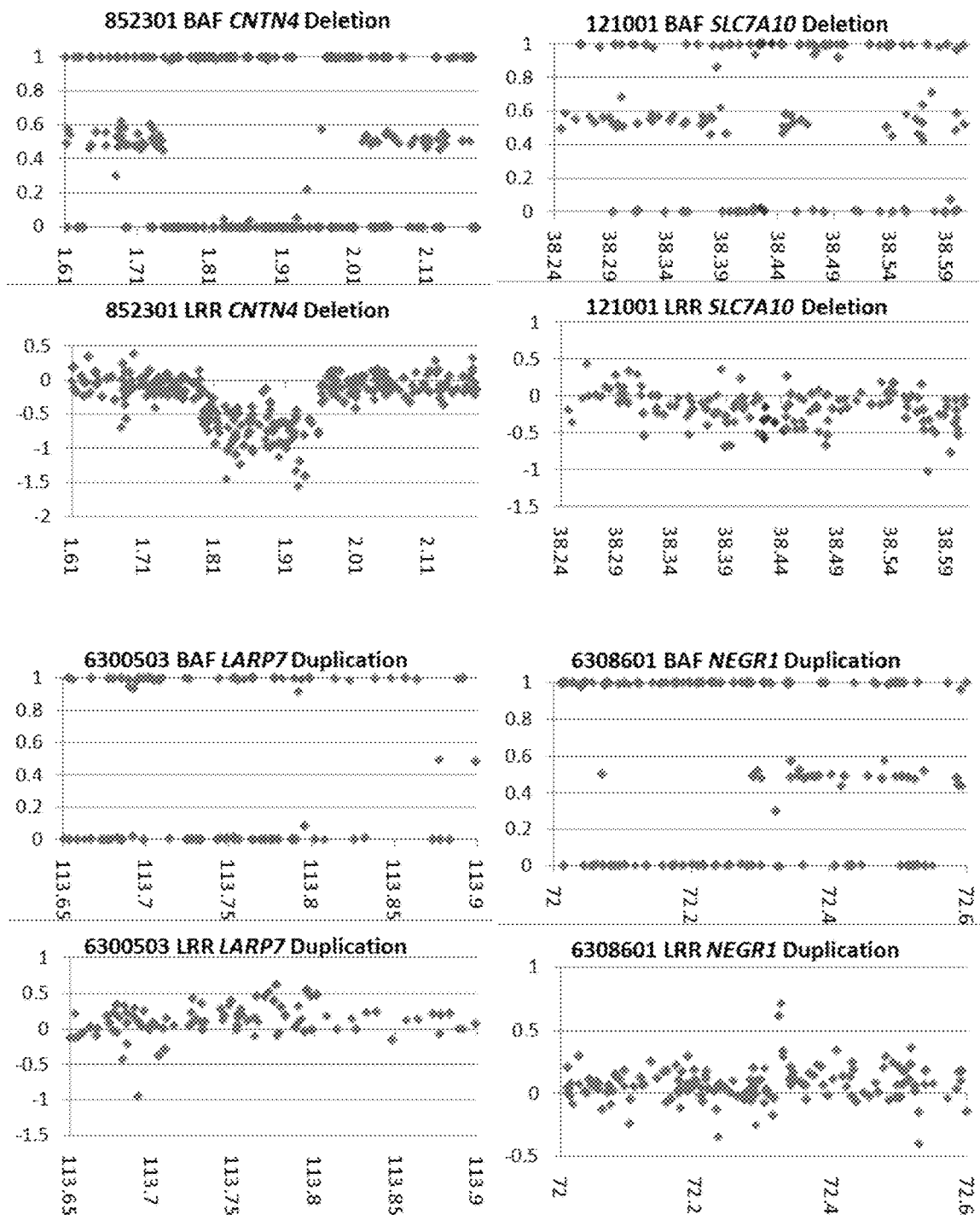
Figure 3F:
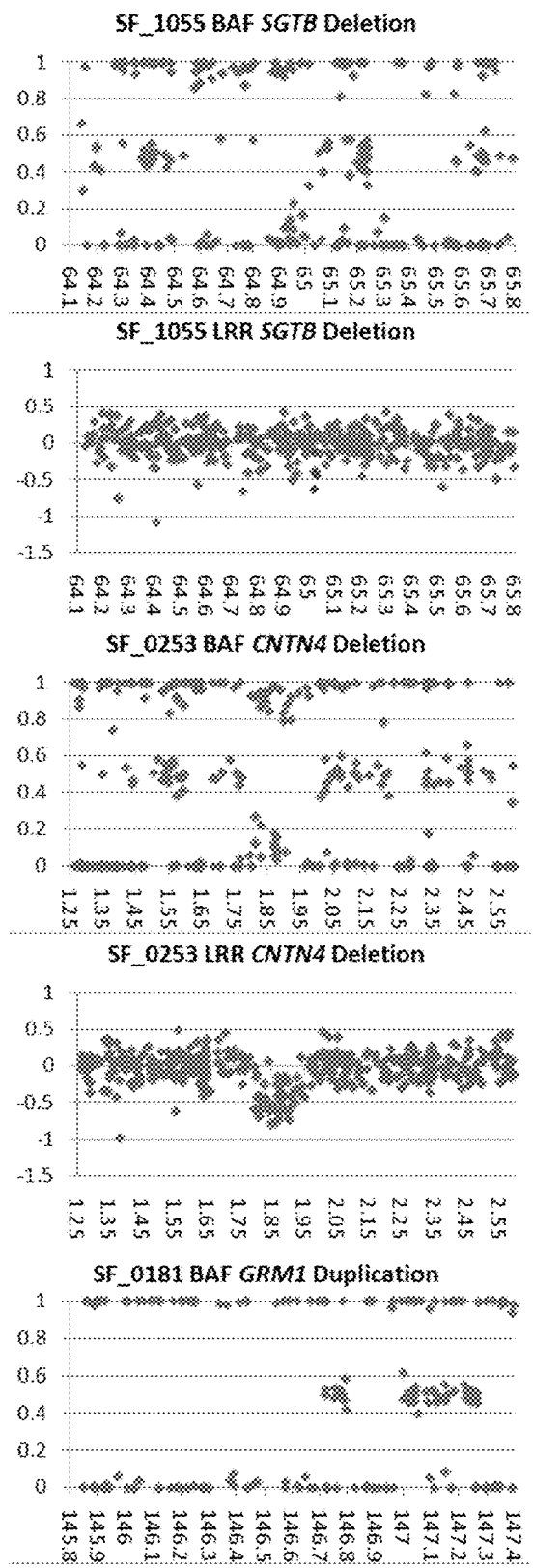
Figure 3F:
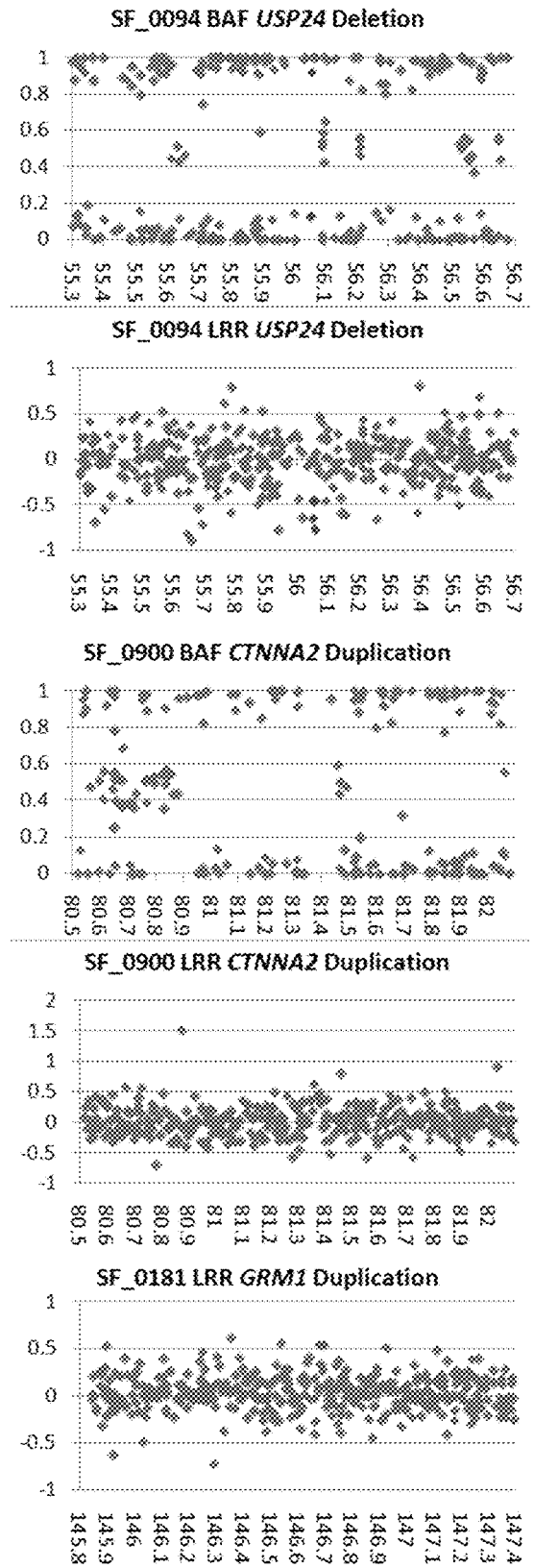

Attention-Deficit, Hyperactivity Disorder (ADHD) is a common, heritable neuropsychiatric disorder of unknown etiology. Recently, we reported an enrichment of rare variants in genes involved in learning, behavior, synaptic transmission and central nervous system development in autism[1], suggesting that rare inherited structural variants could also play a role in the etiology of ADHD, a related neuropsychiatric disorder.

To follow up on those studies, we performed a whole-genome CNV study in a cohort of 1,013 ADHD cases and 4,105 healthy children of European ancestry who were genotyped with 550,000 SNP markers. Positive findings were evaluated in multiple independent cohorts, totaling 2,493 ADHD cases and 9,222 controls of European ancestry, with respective case-control cohorts genotyped on matched platforms.

Our results identified several CNVs impacting metabotropic glutamate receptor genes which were significantly enriched across all independent cohorts ($P=2.1\times10^{-9}$). Among them, deletions in GRM5 (glutamate receptor, metabotropic 5) occurred in ten cases across three independent cohorts and in only one control subject ($P=1.36\times10^{-6}$). In addition, deletions in GRM7 occurred in six cases and GRM8 in eight cases, both with a control frequency of zero. GRM1 was duplicated in eight cases, a frequency notably enriched above controls. Observed variants were experimentally validated using quantitative PCR. Subsequent gene network analysis demonstrated that genes interacting with GRM receptors are significantly enriched for CNVs in cases compared to controls ($P=4.38\times10^{-10}$), collectively impacting ~10% of ADHD cases in this study. Furthermore, we found that GRMs serve as critical hubs that coordinate highly connected modules of interacting genes, many of which harbor CNVs and are enriched for synaptic and neuronal biological functions.

The following definitions are provided to facilitate an understanding of the present invention.

I. DEFINITIONS

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

A "single nucleotide polymorphism (SNP)" refers to a change in which a single base in the DNA differs from the usual base at that position. These single base changes are called SNPs or "snips." Millions of SNP's have been cataloged in the human genome. Some SNPs such as that which causes sickle cell are responsible for disease. Other SNPs are normal variations in the genome.

A "copy number variation (CNV)" refers to the number of copies of a particular gene or segment thereof in the genome of an individual. CNVs represent a major genetic component of human phenotypic diversity. Susceptibility to genetic disorders is known to be associated not only with single nucleotide polymorphisms (SNP), but also with structural and other genetic variations, including CNVs. A CNV represents a copy number change involving a DNA fragment that is ~1 kilobases (kb) or larger (Feuk et al. 2006a). CNVs described herein do not include those variants that arise from the insertion/deletion of transposable elements (e.g., ~6-kb KpnI repeats) to minimize the complexity of future CNV analyses. The term CNV therefore encompasses previously introduced terms such as large-scale copy number variants (LCVs; Iafrate et al. 2004), copy number polymorphisms (CNPs; Sebat et al. 2004), and intermediate-sized variants (ISVs; Tuzun et al. 2005), but not retroposon insertions. The terminology "duplication-containing CNV" is also used herein below consistent with the CNV definition provided.

"ADHD-associated SNP" or "ADHD-associated specific marker" or ADHD-associated informational sequence molecule" is a SNP or marker sequence which is associated with an increased or decreased risk of developing ADHD not found normal patients who do not have this disease. Such markers may include but are not limited to nucleic acids, proteins encoded thereby, or other small molecules. Thus, the phrase "ADHD-associated SNP containing nucleic acid" is encompassed by the above description.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the functional and novel characteristics of the sequence.

The phrase "partial informative CNV" is used herein to refer to a nucleic acid that hybridizes to sequences comprising a duplication on a chromosome however, the partial informative CNV may not be identical to the duplication, rather, the CNV may correspond to only a portion of the duplication, but yet is still informative for the same.

"Target nucleic acid" as used herein refers to a previously defined region of a nucleic acid present in a complex nucleic acid mixture wherein the defined wild-type region contains at least one known nucleotide variation which may or may not be associated with ADHD but is informative of the risk of ADHD. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated. Thus the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any ADHD specific marker gene or nucleic acid, but does not hybridize to other nucleotides. Also polynucleotide which "specifically hybridizes" may hybridize only to a neurospecific specific marker, such as an ADHD-specific marker shown in the Tables contained herein. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., Molecular Cloning, Cold Spring Harbor Laboratory (1989):

$$T_m = 81.5\text{"C} + 16.6 \text{ Log } [\text{Na}^+] + 0.41(\% \, G+C) - 0.63(\% \text{ formamide}) - 600/\# \text{ bp in duplex}$$

As an illustration of the above formula, using $[\text{Na}^+]=[0.368]$ and 50% formamide, with GC content of 42% and an average probe size of 200 bases, the $T_m$ is 57"C. The $T_m$ of a DNA duplex decreases by 1-1.5"C with every 1% decrease in homology. Thus, targets with greater than about 75% sequence identity would be observed using a hybridization temperature of 42"C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the ADHD specific marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the ADHD specific marker nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism", or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

"Sample" or "patient sample" or "biological sample" generally refers to a sample which may be tested for a particular molecule, preferably an ADHD specific marker molecule, such as a marker described hereinbelow. Samples may include but are not limited to cells, body fluids, including blood, serum, plasma, cerebral spinal fluid, urine, saliva, tears, pleural fluid and the like.

The terms "agent" and "compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule which exhibits the capacity to modulate the activity of the CNV or SNP-containing nucleic acids described herein or their encoded proteins. Agents and compounds may also be referred to as "test agents" or "test compounds" which are evaluated for potential biological activity by inclusion in screening assays described herein below.

The term "modulate" as used herein refers to increasing/promoting or decreasing/inhibiting a particular cellular, biological or signaling function associated with the normal activities of the CNV containing molecules described herein or the proteins encoded thereby. For example, the term modulate refers to the ability of a test compound or test agent to interfere with signaling or activity of a gene or protein of the present invention.

II. METHODS OF USING ADHD-ASSOCIATED CNVS AND/OR SNPS FOR DIAGNOSING A PROPENSITY FOR THE DEVELOPMENT OF ADHD

The present invention provides methods of diagnosing ADHD in a patient or methods for identifying a patient having an increased risk of developing ADHD. Diagnosis, as used herein, includes not only the initial identification of ADHD associated with the genetic alterations described herein in a patient but confirmatory testing, or screening in patients who have previously been identified as having or likely to have ADHD. The methods include the steps of providing a biological sample from the patient, measuring the amount of particular sets, or any all of the ADHD associated markers (Table 13) present in the biological sample, preferably a tissue and/or blood plasma sample, and determining if the patient has a greater likelihood of ADHD based on the amount and/or type of ADHD marker expression level determined relative to those expression levels identified in patient cohorts of known outcome. A patient has a greater likelihood of having ADHD when the sample has a CNV marker expression profile associated with patients previously diagnosed with ADHD. The compositions and methods of the invention are useful for the prognosis and diagnosis and management of ADHD In another aspect, the patient sample may have been previously genotyped and thus the genetic expression profile in the sample may be available to the clinician. Accordingly, the method may entail storing reference ADHD associated marker sequence information in a database, i.e., those CNVs statistically associated with a more favorable or less favorable prognosis as described in the tables herein, and performance of comparative genetic analysis on the computer, thereby identifying those patients having increased risk ADHD.

ADHD-related CNV or SNP-containing nucleic acids, including but not limited to those listed below may be used for a variety of purposes in accordance with the present invention. ADHD-associated CNV or SNP-containing DNA, RNA, or fragments thereof may be used as probes to detect the presence of and/or expression of ADHD specific markers. Methods in which ADHD specific marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting ADHD-associated CNVs or SNPs may be conducted on any type of biological sample, including but not limited to body fluids (including blood, urine, serum, gastric lavage, cerebral spinal fluid), any type of cell (such as brain cells, white blood cells, mononuclear cells, fetal cells in maternal circulation) or body tissue.

Clearly, ADHD-associated CNV or SNP-containing nucleic acids, vectors expressing the same, ADHD CNV or SNP-containing marker proteins and anti-ADHD specific marker antibodies of the invention can be used to detect ADHD associated CNVs or SNPs in body tissue, cells, or fluid, and alter ADHD CNV or SNP-containing marker protein expression for purposes of assessing the genetic and protein interactions involved in the development of ADHD.

In most embodiments for screening for ADHD-associated CNVs or SNPs, the ADHD-associated CNV or SNP-containing nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are important in the art.

Alternatively, new detection technologies can overcome this limitation and enable analysis of small samples containing as little as 1 µg of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Any of the aforementioned techniques may be used to detect or quantify ADHD-associated CNV or SNP marker expression and accordingly, diagnose ADHD.

III. KITS AND ARTICLES OF MANUFACTURE

Any of the aforementioned products can be incorporated into a kit which may contain a ADHD-associated CNV or SNP specific marker polynucleotide or one or more such markers immobilized on a Gene Chip, an oligonucleotide, a polypeptide, a peptide, an antibody, a label, marker, reporter, a pharmaceutically acceptable carrier, a physiologically acceptable carrier, instructions for use, a container, a vessel for administration, an assay substrate, or any combination thereof.

IV. METHODS OF USING ADHD-ASSOCIATED CNVS AND/OR SNPS FOR THE DEVELOPMENT OF THERAPEUTIC AGENTS

Since the CNVs and SNPs identified herein have been associated with the etiology of ADHD, methods for identifying agents that modulate the activity of the genes and their encoded products containing such CNVs and/or SNPs should result in the generation of efficacious therapeutic agents for the treatment of this disorder.

Several regions of the human genome provide suitable targets for the rational design of therapeutic agents. Small nucleic acid molecules or peptide molecules corresponding to these regions may be used to advantage in the design of therapeutic agents that effectively modulate the activity of the encoded proteins.

Molecular modeling should facilitate the identification of specific organic molecules with capacity to bind to the active site of the proteins encoded by the CNV or SNP-containing nucleic acids based on conformation or key amino acid residues required for function. A combinatorial chemistry approach will be used to identify molecules with greatest activity and then iterations of these molecules will be developed for further cycles of screening. Several of the molecules available in this screening assay, while not limiting the method, include metabotropic glutamate receptor (mGluR) positive allosteric modulators (PAM), negative allosteric modulators (NAM), and tachykinin-3/neurokinin-3 receptor (TACR-3/NK3R) antagonists. A specific list includes ADX63365, ADX50938, ADX71149, ADX48621, AMN082, 1-(hetero)aryl-3-amino-pyrrolidine derivatives (e.g. those provided in U.S. Patent Application Publication No. 2008/0300266), LY341495, GSK1144814, and SB223412 (Table 1).

TABLE 1

Molecules and therapeutic agents available for a combinatorial chemistry approach.

| Product Name | Company Name | Indication | Mechanism of Action |
|---|---|---|---|
| ADX63365 | Addex Pharmaceuticals | Schizophrenia | Glutamate Receptor, Metabotropic 5 (GRM5) Positive Allosteric Modulator |
| ADX63365 | Merck & Co Inc | Schizophrenia | Glutamate Receptor, Metabotropic 5 (GRM5) Positive Allosteric Modulator |
| ADX50938 | Addex Pharmaceuticals | Schizophrenia | Glutamate Receptor, Metabotropic 5 (GRM5) Positive Allosteric Modulator |
| ADX50938 | Addex Pharmaceuticals | Alzheimer Disease | Glutamate Receptor, Metabotropic 5 (GRM5) Positive Allosteric Modulator |
| ADX71149 | Addex Pharmaceuticals | Schizophrenia | Glutamate Receptor, Metabotropic 2 (GRM2) Positive Allosteric Modulator |
| AMN082 | — | Schizophrenia, Depression, Alzheimer Disease | Glutamate Receptor, Metabotropic 7 (GRM7) Positive Allosteric Modulator |
| 1-(hetero)aryl-3-amino-pyrrolidine derivatives | Eli Lilly & Co | Migraine | Glutamate Receptor, Metabotropic 3 (GRM3) Antagonist |
| LY341495 | Eli Lilly & Co | Central Nervous System Disorders | Glutamate Receptor, Metabotropic 2 (GRM2) Antagonist; Glutamate Receptor, Metabotropic 3 (GRM3) Antagonist |
| ADX48621 | Addex Pharmaceuticals | Parkinson's Disease | Glutamate Receptor, Metabotropic 5 (GRM5) Negative Allosteric Modulator |

TABLE 1-continued

Molecules and therapeutic agents available for a combinatorial chemistry approach.

| Product Name | Company Name | Indication | Mechanism of Action |
| --- | --- | --- | --- |
| GSK1144814 | Glaxo Smith Kline | Schizophrenia | Antagonist for Neurokinin-3 receptors |
| SB223412 (Talnetant) | Glaxo Smith Kline | Schizophrenia | Antagonist for Neurokinin-3 receptors |

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as described above) which have a nonfunctional or altered ADHD associated gene. These host cell lines or cells are defective at the polypeptide level. The host cell lines or cells are grown in the presence of drug compound. Altered glutaminergic function of the host cells is measured to determine if the compound is capable of regulating this function in the defective cells. Host cells contemplated for use in the present invention include but are not limited to bacterial cells, fungal cells, insect cells, mammalian cells, and plant cells. However, mammalian cells, particularly neuronal cells are preferred. The ADHD-associated CNV or SNP encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

A wide variety of expression vectors are available that can be modified to express the novel DNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/V5&His (Invitrogen); baculovirus vectors such as pVL1392, pVL1393, or pAC360 (Invitrogen); and yeast vectors such as YRP17, YIPS, and YEP24 (New England Biolabs, Beverly, Mass.), as well as pRS403 and pRS413 Stratagene Inc.); Picchia vectors such as pHIL-D1 (Phillips Petroleum Co., Bartlesville, Okla. 74004); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and *Saccharomyces* promoters such as the gal4 inducible promoter and the PGK constitutive promoter, as well as neuronal-specific platelet-derived growth factor promoter (PDGF), the Thy-1 promoter, the hamster and mouse Prion promoter (MoPrP), and the Glial fibrillar acidic protein (GFAP) for the expression of transgenes in glial cells.

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the ADHD-associated CNVs and/or SNPs of the present invention or functional fragments thereof provide a system in which to screen potential compounds or agents for the ability to modulate the development of ADHD. Thus, in one embodiment, the nucleic acid molecules of the invention may be used to create recombinant cell lines for use in assays to identify agents which modulate aspects of cellular metabolism associated with ADHD and aberrant glutaminergic function. Also provided herein are methods to screen for compounds capable of modulating the function of proteins encoded by CNV and SNP-containing nucleic acids.

Another approach entails the use of phage display libraries engineered to express fragment of the polypeptides encoded by the CNV or SNP-containing nucleic acids on the phage surface. Such libraries are then contacted with a combinatorial chemical library under conditions wherein binding affinity between the expressed peptide and the components of the chemical library may be detected. U.S.

Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved polypeptide activity or stability or which act as inhibitors, agonists, antagonists, etc. of polypeptide activity. By virtue of the availability of CNV or SNP-containing nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of ADHD-associated CNV or SNP-containing nucleic acids enables the production of strains of laboratory mice carrying the ADHD-associated SNPs or CNVs of the invention. Transgenic mice expressing the ADHD-associated CNV or SNP of the invention provide a model system in which to examine the role of the protein encoded by the CNV or SNP-containing nucleic acid in the development and progression towards ADHD. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role that a target protein plays in various cellular metabolic processes, including: aberrant glutaminergic function, altered neuroactive ligand receptor signaling and aberrant neurotransmission, or altered neuronal morphology and neurite outgrowth. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of ADHD-associated CNV or SNP-containing nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated ADHD-associated CNV or SNP genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodou-racil, (FIAU). By this counter selection, the number of homologous recombinants in the surviving transformants can be increased. Utilizing ADHD-associated CNV or SNP-containing nucleic acid as a targeted insertional cassette provides means to detect a successful insertion as visualized, for example, by acquisition of immunoreactivity to an antibody immunologically specific for the polypeptide encoded by ADHD-associated CNV or SNP nucleic acid and, therefore, facilitates screening/selection of ES cells with the desired genotype.

As used herein, a knock-in animal is one in which the endogenous murine gene, for example, has been replaced with human ADHD-associated CNV or informative fragment thereof or SNP-containing gene of the invention. Such knock-in animals provide an ideal model system for studying the development of ADHD.

As used herein, the expression of a ADHD-associated CNV or SNP-containing nucleic acid, partial informative CNV fragment thereof, or an ADHD-associated fusion protein in which the CNV or SNP is encoded can be targeted in a "tissue specific manner" or "cell type specific manner" using a vector in which nucleic acid sequences encoding all or a portion of an ADHD-associated CNV or SNP are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific proteins are well known in the art and described herein.

The nucleic acid sequence encoding the ADHD-associated CNV or SNP of the invention may be operably linked to a variety of different promoter sequences for expression in transgenic animals. Such promoters include, but are not limited to a prion gene promoter such as hamster and mouse Prion promoter (MoPrP), described in U.S. Pat. No. 5,877,399 and in Borchelt et al., Genet. Anal. 13(6) (1996) pages 159-163; a rat neuronal specific enolase promoter, described in U.S. Pat. Nos. 5,612,486, and 5,387,742; a platelet-derived growth factor B gene promoter, described in U.S. Pat. No. 5,811,633; a brain specific dystrophin promoter, described in U.S. Pat. No. 5,849,999; a Thy-1 promoter; a PGK promoter; a CMV promoter; a neuronal-specific platelet-derived growth factor B gene promoter; a NEGR1 promoter, a GRM5 promoter, a promotor of any gene listed in the tables below, and Glial fibrillar acidic protein (GFAP) promoter for the expression of transgenes in glial cells.

Methods of use for the transgenic mice of the invention are also provided herein. Transgenic mice into which a nucleic acid containing the ADHD-associated CNV or SNP or its encoded protein have been introduced are useful, for example, to develop screening methods to screen therapeutic agents to identify those capable of modulating the development of ADHD.

V. PHARMACEUTICAL AND PEPTIDE THERAPIES

The elucidation of the role played by the ADHD associated CNVs and SNPs described herein in neuroactive ligand receptor signaling facilitates the development of pharmaceutical compositions useful for treatment and diagnosis of ADHD. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

The materials and methods set forth below are provided to facilitate the practice of the following examples.

Illumina Infinium Assay for CNV Discovery

We performed high-throughput, genome-wide SNP genotyping, using the InfiniumII HumanHap550 BeadChip technology (Illumina San Diego Calif.), at the Center for Applied Genomics at CHOP. The genotype data content together with the intensity data provided by the genotyping array provides high confidence for CNV calls. Importantly, the simultaneous analysis of intensity data and genotype data in the same experimental setting establishes a highly accurate definition for normal diploid states and any deviation thereof. To call CNVs, we used the PennCNV algorithm, which combines multiple sources of information, including Log R Ratio (LRR) and B Allele Frequency (BAF) at each SNP marker, along with SNP spacing and population frequency of the B allele to generate CNV calls. The replication case and control cohorts utilized genome-wide SNP genotyping using the Perlegen 600K, Illumina 1M, and Affymetrix 5.0 arrays. Raw X and Y values were normalized with log(10) and clustered to establish BAF and LRR with PennCNV-Affy protocol (Table 2). Rare recurrent CNVs were the focus of our study.

TABLE 2

Perlegen Data Reformatted File Samples to match Affymetrix Power Tools output format.

| probeset_id | 10009 | 10010 | 10021 | 10022 |
|---|---|---|---|---|
| A) Genotype Calls File (0 = AA, 1 = AB, 2 = BB, −1 = NoCall). | | | | |
| SNP_rs10000023 | 1 | 1 | 2 | 1 |
| SNP_rs10000030 | 1 | 0 | 0 | 1 |
| SNP_rs10000037 | 0 | 0 | 1 | 1 |
| SNP_rs10000068 | 2 | 2 | 2 | 2 |
| B) Genotype Calls Confidence Scores (All set to 1). | | | | |
| SNP_rs10000023 | 1 | 1 | 1 | 1 |
| SNP_rs10000030 | 1 | 1 | 1 | 1 |
| SNP_rs10000037 | 1 | 1 | 1 | 1 |
| SNP_rs10000068 | 1 | 1 | 1 | 1 |
| C) Intensity Summary (-A = log10(X), -B = log10(Y) (X and Y value from dbGaP Single Sample Final Report files). | | | | |
| SNP_rs10000023-A | 2.85 | 2.78 | 2.07 | 2.89 |
| SNP_rs10000023-B | 2.86 | 2.84 | 2.98 | 2.96 |
| SNP_rs10000030-A | 2.9 | 2.99 | 2.95 | 3.02 |
| SNP_rs10000030-B | 2.91 | 2.4 | 2.38 | 3.05 |

CNV Calls and Review of Significant Loci

No additional "CNV burden" was observed in cases vs. controls, rather the distribution of calls made was highly comparable (FIG. 1). We established CNV call reliability in Illumina and Perlegen data by observing Mendelian patterns of inheritance. Trios were first verified by genotype inheritance and analyzed to establish the quality of CNV calls from both Illumina and Perlegen platforms based on observed inheritance. Based on all CNV calls called in trios from the Illumina CHOP data, 8,647 CNVs observed in offspring were inherited from a parent while 437 CNVs were putatively de novo which is a de novo rate of 4.811%. Based on all CNV calls called in trios from the Perlegen IMAGE data, 1,862 CNVs observed in offspring were inherited from a parent while 505 CNVs were putatively de novo which is a de novo rate of 21.335%. 51 IMAGE cases, 22 deletion loci, and 5 duplication loci had multiple de novo events due to low data quality and were excluded as outliers; once excluded, 785 CNVs were inherited and 63 were denovo which lowered the observed denovo rate to an acceptable level of 7.429%. Based on CNVs observed in parents from Illumina CHOP data, 9,305 CNVs were passed to the child while 7,432 CNVs were not inherited resulting in a 55.595% inheritance rate. Based on all CNVs observed in parents from Perlegen IMAGE data, 2,114 CNVs were passed to the child while 3,789 CNVs were not inherited resulting in a 35.812% inheritance rate. We excluded 65 parent samples that were outliers with 20 or greater CNVs not inherited to offspring and filtering these samples out resulted in 1,204 CNVs were passed to the child while 1,221 were not inherited resulting in a 49.650% inheritance rate which established confidence in this CNV call set.

It is intractable to review all PennCNV calls and wasteful to exclude CNVs smaller than a size threshold. Instead, we statistically score the loci based on all CNVs detected and review these nominally associated CNVR loci for appropriate overlap, signal quality, and Mendelian inheritance. As shown in Table 3, all reported loci show at least one case with the CNV inherited from a parent, in cases where both parents were available.

TABLE 3

Novel CNVRs Over-represented in ADHD Patients

| CNVR | CHOP Cases n = 1013 | CHOP Controls n = 4105 | Replication Cases n = 2493 | Replication Controls n = 9222 | Inh | Combined P-value | OR CI (95%) | Type | Gene | Exon Distance |
|---|---|---|---|---|---|---|---|---|---|---|
| A) Loci Significantly Associated with ADHD | | | | | | | | | | |
| chr11: 88269449-88351661 | 4‡(3*) | 0 | 6 | 1 | 4:1:3 62.5% | $1.36 \times 10^{-6}$ | 38.12 (5-298) | Del | GRM5 | 5,858 |
| chr7: 126525124-126536202 | 3 | 0 | 5 | 0 | 0:1:0 100% | $3.52 \times 10^{-6}$ | infinity | Del | GRM8 | 0 |
| chr3: 7183953-7197236 | 4†(1*) | 0 | 2 | 0 | 0:2:0 100% | $8.14 \times 10^{-5}$ | infinity | Del | GRM7 | 20,598 |
| chr6: 146657076-146694047 | 5 | 2 | 3 | 0 | 2:0:0 100% | $1.05 \times 10^{-4}$ | 15.24 (3-72) | Dup | GRM1 | 0 |
| B) ADHD Loci with Nominal Significance | | | | | | | | | | |
| chr1: 72317292-72328395 | 4‡ | 0 | 1 | 0 | 0:3:0 100% | $3.91 \times 10^{-4}$ | infinity | Dup | NEGR1 | 10,621 |
| chr7: 153495598-153564827 | 5(1*) | 0 | 3 | 2 | 1:2:0 100% | $4.08 \times 10^{-4}$ | 15.24 (3-72) | Dup | DPP6 | 68,453 |
| chr5: 65027976-65046520 | 4 | 0 | 2 | 1 | 2:0:2 50% | $4.68 \times 10^{-4}$ | 22.85 (3-190) | Del | SGTB/NLN | 0 |
| chr1: 56053497-56064495 | 2 | 0 | 4 | 2 | 1:0:3 25% | $1.54 \times 10^{-3}$ | 11.42 (2-57) | Del | USP24* | 80,234 |
| chr19: 38427720-38444834 | 5 | 2 | 2 | 3 | 2:2:1 80% | $4.95 \times 10^{-3}$ | 5.33 (2-17) | Del | SLC7A10* | 19,172 |
| chr3: 1844168-1859889 | 4† | 0 | 3 | 6 | 1:3:0 100% | $8.81 \times 10^{-3}$ | 4.44 (1-13) | Del | CNTN4* | 255,661 |
| chr2: 81419297-81446082 | 2 | 0 | 2 | 3 | 1:0:1 50% | $3.83 \times 10^{-2}$ | 5.07 (1-23) | Dup | CTNNA2* | 152,417 |

TABLE 3-continued

Novel CNVRs Over-represented in ADHD Patients

| CNVR | CHOP Cases n = 1013 | CHOP Controls n = 4105 | Replication Cases n = 2493 | Replication Controls n = 9222 | Inh | Combined P-value | OR CI (95%) | Type | Gene | Exon Distance |
|---|---|---|---|---|---|---|---|---|---|---|
| chr4: 113772340-113788584 | 2 | 0 | 2 | 3 | 0:0:0 NA | $3.83 \times 10^{-2}$ | 5.07 (1-23) | Dup | LARP7 | 0 |

*Cases presented in (13);
‡3 Cases are present in the same family;
†2 Cases are present in the same family;
The "Inh" column lists the inheritance pattern of each CNV from parents to cases in the format <inherited from mother>:<inherited from father>:<denovo>. The percentage of Inheritance is listed below. Note that parents were not available for all cases. Rare variants that were recurrent and observed to be enriched among ADHD cases relative to control frequencies and detected in multiple independent cohorts are reported. All GRM genes are directly impacted by the CNVR. Regions listed represent the optimal overlap of cases and significance with respect to controls as described in the Methods. The closest gene is listed for each CNVR locus since it is most likely to be impacted. For detailed counts from each contributing project see Table 16.
*No gene directly impacted so closest proximal gene listed. Individual CNV boundaries are provided in Table 17.
OR: Odds Ratio
CI: Confidence Interval.
Replication represents combined IMAGE, PUWMa, IMAGEII, NIMH, and Utah.

In total, there are 3,506 cases and 13,327 controls, representing greater than a three-fold abundance of control samples to robustly define CNVs to be absent or at a lower frequency than case samples. Although the number of CNVs detected per sample was as high as 70, there are actually inferred normal diploid (CN=2) calls which make every sample equivalent. These CNVs are very rare and thus the number of observed CNV calls will vary between samples.

CNV Validation by Quantitative PCR (QPCR)

Universal Probe Library (UPL; Roche, Indianapolis, Ind.) probes were selected using the ProbeFinder v2.41 software (Roche, Indianapolis, Ind.). Quantitative PCR was performed on an ABI 7500 Real Time PCR Instrument or on an ABI Prism™ 7900HT Sequence Detection System (Applied Biosystems, Foster City, Calif.). Each sample was analyzed in quadruplicate either in 25 µl reaction mixture (250 nM probe, 900 nM each primer, Fast Start TaqMan Probe Master from Roche, and 10 ng genomic DNA) or in 10 µl reaction mixture (100 nM probe, 200 nM each primer, lx Platinum Quantitative PCR SuperMix-Uracil-DNA-Glycosylase (UDG) with ROX from Invitrogen, and 25 ng genomic DNA). The values were evaluated using Sequence Detection Software v2.2.1 (Applied Biosystems, CA). Data analysis was further performed using the $\Delta\Delta C_T$ method. Reference genes, chosen from COBL, GUSB, and SNCA, were included based on the minimal coefficient of variation and then data was normalized by setting a normal control to a value of 1.

The CNV calling on Perlegen platform used a highly similar algorithm to those used on the Illumina arrays, but the signal pre-processing steps differ. Unlike the Illumina platform, where normalized signal intensities (Log R Ratio and B Allele Frequency) can be exported directly from the BeadStudio software, these signal intensity measures in the Perlegen 600K platform need to be calculated from the collection of genotyped samples based on raw X and Y values. To perform data normalization and signal extraction from raw final report files generated in genotyping experiments, we first reformatted data from dbGaP into the format produced by Affymetrix Power Tools: birdseed.calls.txt, birdseed.confidences.txt, and quant-norm.pm-only.med-polish.expr.summary.txt (see Table 2). The X and Y values provided in the sample based report files from dbGaP were reduced to a more finite range by taking the logarithm base 10. For each SNP marker, we then relied on the allele-specific signal intensity for the AA, AB and BB genotypes on all genotyped samples to construct three canonical genotype clusters in polar coordinates theta and R, similar to the Illumina clustering generation approach. The "-conf 2" option was included in running generate_affy_geno_cluster.pl since 1 was coded as the best score. Once the canonical genotype clusters were constructed, we then transformed the signal intensity values for each SNP to Log R Ratio (LRR) and B Allele Frequency (BAF) values using normalize affy_geno_cluster.pl. For more technical details, see www.openbioinformatics.org/penncnv/penncnv_tutorial_affy_gw6.html.

To optimize the Hidden Markov Model (HMM), we used the baseline reference file hh550.hmm and ran "-train" in PennCNV in three successive batches of thirty. The first training used the samples with the lowest standard deviation of LRR while the other two runs, using the file created as a new reference, included more random representative samples. We also created definition files providing inter-SNP distance and population b-allele frequency to further inform CNV calling specifically adapted to the observed Perlegen data. This allowed for CNV calls to be made in 1,887 (642 cases and 1,245 parents) out of 2,789 Perlegen 600K samples available. Although the global standard deviation of LRR was below 0.2 for the majority (84%) of samples, the intensity data was notably noisier in regions of called CNV and often showed a subpopulation of SNPs unable to differentiate a deletion signal, perhaps due to PCR saturation during the lab processing. Nevertheless, the deletion and duplication features were still detected with confirmation of homozygote and AAB/ABB genotypes respectively shown for the same SNPs (see FIGS. 2 and 3).

Lastly, Perlegen CNV calls were screened for overlap with the 11 loci associated based on the CHOP Illumina data. The SNP level data underlying each CNV call was reviewed to ensure clean signal quality. To ensure that each detected CNV was a true DNA feature and not in any way an artifact of the Perlegen 600K array used or our bioinformatics manipulations of the data, we validated each CNV with qPCR at an independent lab (see FIG. 4).

CNV Quality Control

Figure 5:
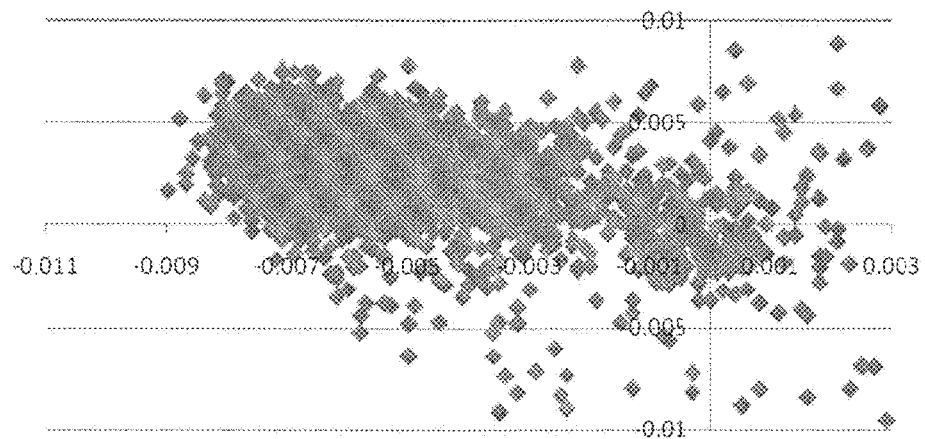
FIG. 5. An illustration of the Eigenstrat Principle Components Analysis. Cases and Controls were simultaneously analyzed to minimize population substructure in case control CNV association. Samples deviating from the Caucasian cluster shown were removed. The genomic inflation factor (GIF) within Plink was at an acceptable level (GIF=1.02409). We also checked pairwise population concordance to check for and filter out cryptic relatedness which could give rise to rare CNVs specific to ultra-stratified subpopulations of Europe.
Figure 5:
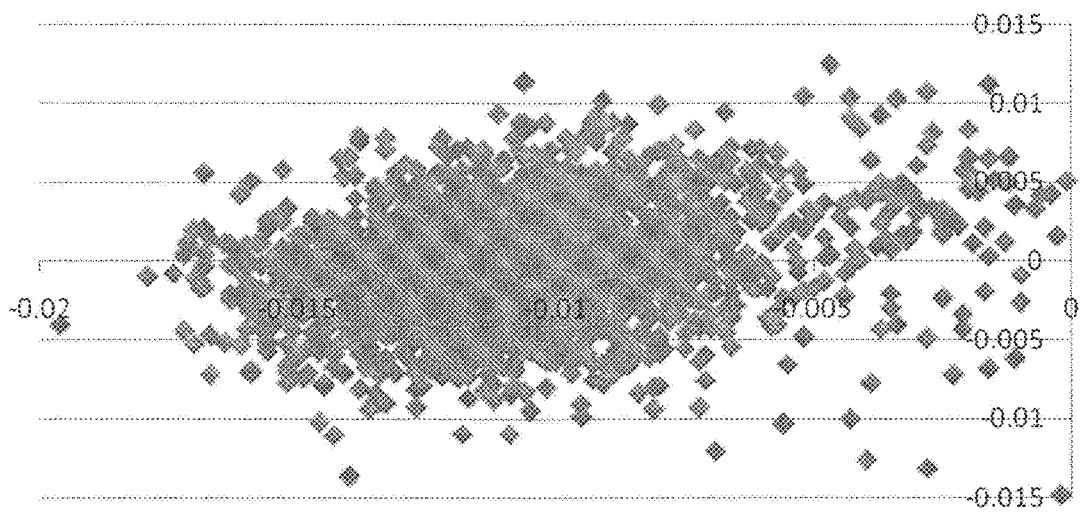
Figure 6A:
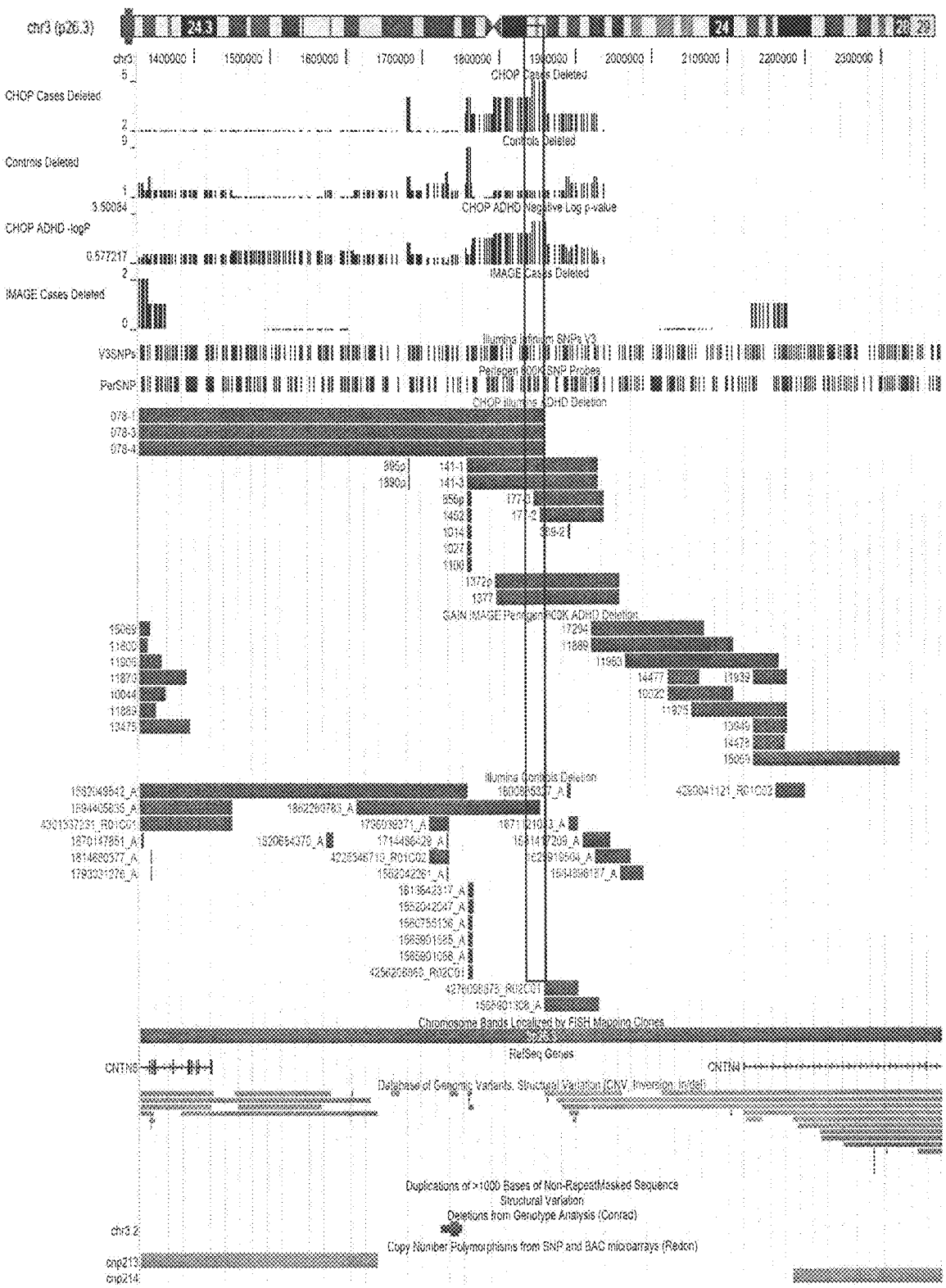
FIGS. 6A-B. An example of the SNP-based statistics applied and the resulting highest significance region Called. Examples from chr 3 are shown: 6A) 1,327,963-2,376,095 and 6B) 1,847,000-1,862,261. Complex CNV overlap is simplified by producing SNP-based statistics. As seen in plots for cases deleted and controls deleted, each SNP has a specific number of CNVs. The cases and controls are compared with a Fisher's exact test and the negative log p value is shown in the third plot. Regions of significance ranging within a power of ten are reported and the region of highest significance (local minimum p-value) within 1 MB is reported. The IMAGE cases deleted plot shows only one case sample #11939 since the remaining regions 3' are parents.
Figure 6B:
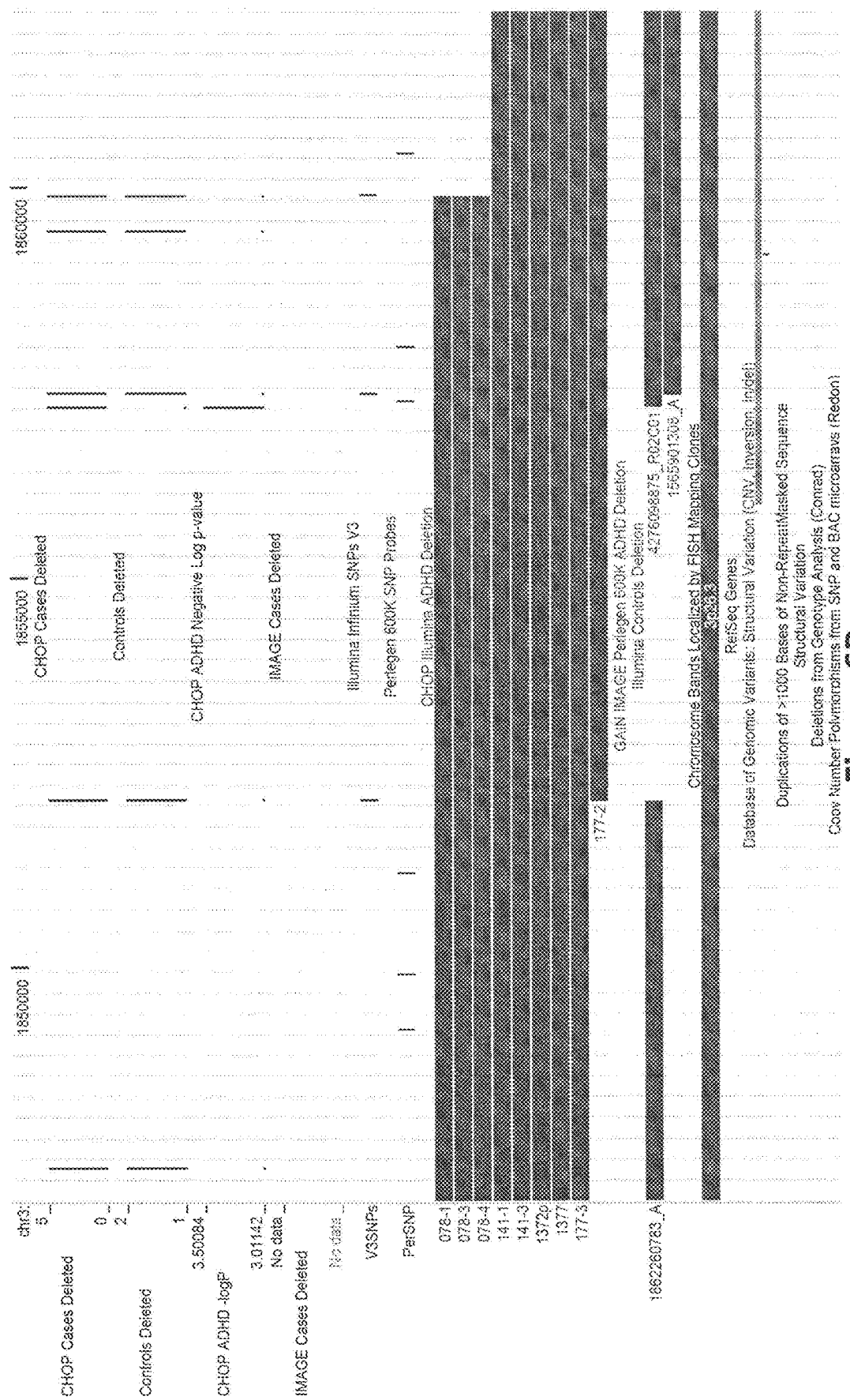

We calculated Quality Control (QC) measures on our HumanHap550 GWAS data based on statistical distributions to exclude poor quality DNA samples and false positive CNVs. The first threshold is the percentage of attempted SNPs which were successfully genotyped. Only samples with call rate >98% were included. The genome wide intensity signal must have as little noise as possible. Only samples with the standard deviation (SD) of normalized intensity (LRR)<0.35 were included. All samples must have Caucasian ethnicity based on principle components analysis (FIG. 5) and all other samples were excluded. Furthermore, case and control matching was insured by calculating a genomic inflation factor (GIF=1.024) between groups. Wave artifacts roughly correlating with GC content resulting from hybridization bias of low full length DNA quantity are known to interfere with accurate inference of copy number variations[43]. Only samples where the wave factor of LRR to wave model ranged between −0.5<x<0.6 were accepted. If the count of CNV calls made by PennCNV exceeds 70 (FIG. 1), the DNA quality is usually poor. Thus, only samples with CNV call count <70 were included. Any duplicate samples (such as monozygotic twins) had one sample excluded. Table 4 provides the number of samples excluded for each quality control measure.

TABLE 4

Sample exclusion based on quality control measures.

| Exclusion Criteria | CHOP | Control |
|---|---|---|
| Call Rate <98% | 170 | 271 |
| SD LRR >0.35 | 73 | 124 |
| Ethnicity non-Caucasian | 71 | 48 |
| Wave Factor −0.5 > X > 0.6 | 251 | 1040 |
| Count CNVs >70 | 197 | 237 |
| Monozygotic Twin | 31 | 38 |

Samples excluded based on Quality Control (QC) measures on our HumanHap550 GWAS data based on statistical distributions to exclude poor quality DNA samples and false positive CNVs.

Statistical Analysis of CNVs

Figure 4:
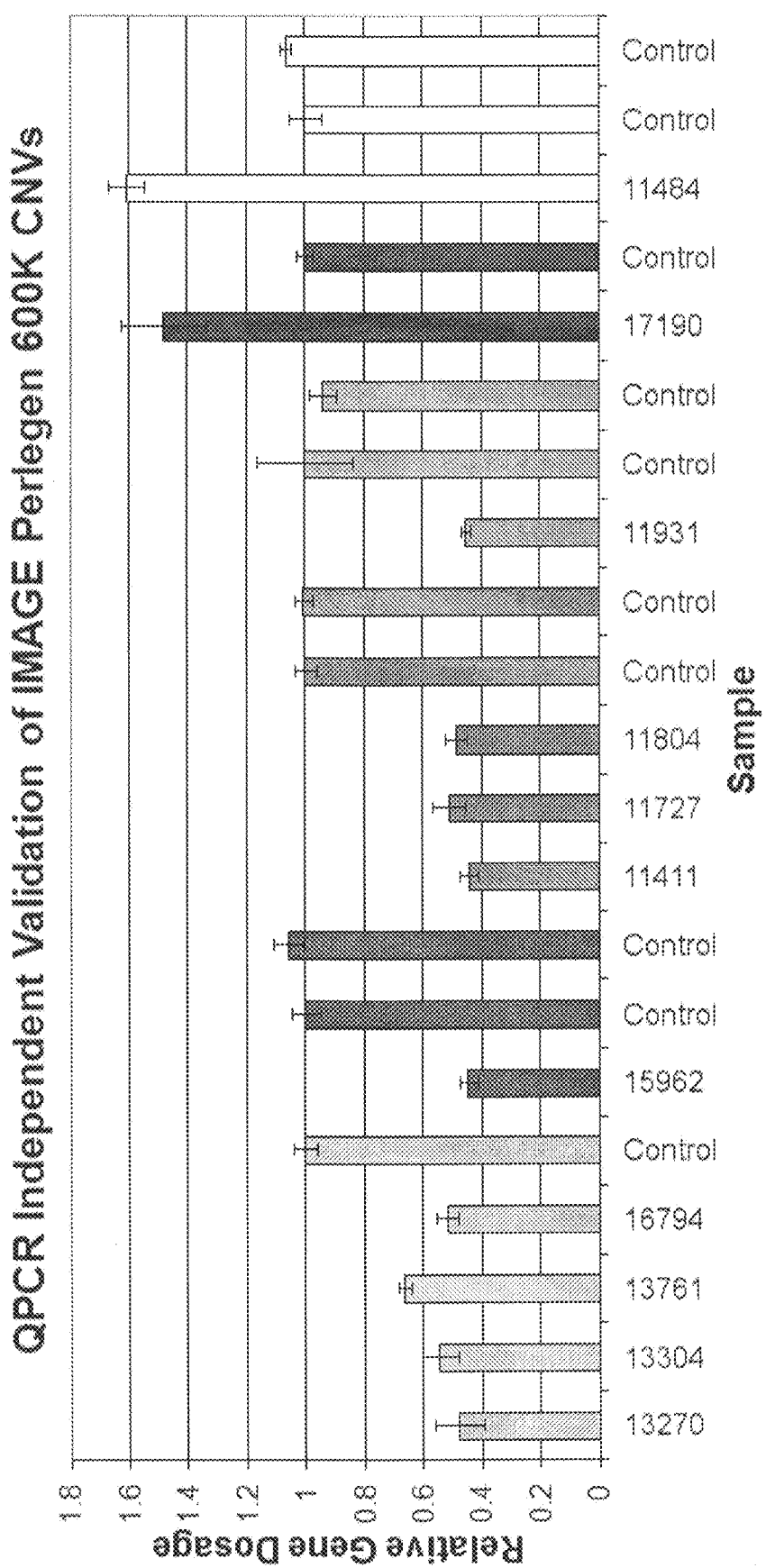
FIG. 4. A graphical display of the IMAGE Perlegen 600K Independent Validation data. Fluorescent probe-based qPCR assays using Roche Universal probe were designed to validate every candidate CNV with a completely independent test (11 of the 14 IMAGE samples with replicating CNV calls for the loci reported were available for validation and all validated in comparison with control pairs; the other 3 loci were visually validated). Error bars denote the standard deviation of quadruplicate runs. Del, deletion; Dup, duplication.

CNV frequency between cases and controls was evaluated at each SNP using Fisher's exact test. We only considered loci that were nominally significant between cases and controls (p<0.05) where cases in the CHOP discovery cohort had the same variation, replicated in IMAGE, PUWMa, or IMAGE II or were not observed in any of the control subjects, and validated with an independent method. We report statistical local minimums to narrow the association in reference to a region of nominal significance including SNPs residing within 1 Mb of each other (FIG. 4). Resulting nominally significant CNVRs were excluded if they met any of the following criteria: i) residing on telomere or centromere proximal cytobands; ii) arising in a "peninsula" of common CNV arising from variation in boundary truncation of CNV calling (FIG. 7); iii) genomic regions with extremes in GC content which produces hybridization bias; or iv) samples contributing to multiple CNVRs. We statistically adjusted for relatedness of cases with permutation (1000×). Three lines of evidence establish statistical significance: independent replication p<0.05, permutation of observations, and no loci observed with control enriched significance. We used DAVID (Database for Annotation, Visualization, and Integrated Discovery)[44] to assess the significance of functional annotation clustering of independently associated CNV results into InterPro categories.

Permutation to Adjust Significance for Relatedness

For initial Fisher's exact test, related individuals are not controlled for since our primary objective is to detect CNVs in multiple samples regardless of relatedness. CNVRs passing this initial screen are scored for statistical significance based on a permuted P-value which permutes case and control labels randomly of all samples with the condition that related individuals must have the same label. Each unrelated individual is assigned a case or control label and their related sibling is assigned the same label. Based on the number of samples with the CNVR being calculated in randomly assigned "cases" and "controls" a Fisher's exact test P-value is assigned. The number of hypothetical scenarios with significance equal or greater (lower P-value) provides the permuted P-value which corrects for relatedness. The Fisher's exact test P-value and counts of cases and controls with each CNVR are provided for transparency.

Analysis of Genotype Call Genome-Wide Association

Full scale genotype genome-wide association was performed and the genomic inflation factor (GIF) was at an acceptable level (GIF=1.02409). We also checked pairwise population concordance to check for and filter out cryptic relatedness which could give rise to rare CNVs specific to ultra-stratified subpopulations of Europe. We performed Transmission Disequilibrium Test (TDT) statistic using Plink on 397 ADHD cases with both parents on the CHOP Illumina HumanHap550 genotype data (Table 5). The top result with more than one significant SNP in a region was chr4p12 P(rs1018199)=$2.71 \times 10^{-5}$ and P(rs11724347)=$6.19 \times 10^{-5}$ which impacts TEC. We also performed a case:control genotype genome-wide association on 735 cases and 2,298 controls using the same Illumina data set (Table 6). The strongest signal was chr19p12 P(rs2081051)=$4.60 \times 10^{-6}$ and P(rs399686)=$4.72 \times 10^{-6}$ residing between ZNF66 and ZNF85. Lastly, 623 ADHD cases with both parents on the IMAGE Perlegen 600K data were analyzed with TDT statistic (Table 7). The most significant signal was chr5q23.1 P(rs17144308)=$9.70 \times 10^{-6}$ and P(rs2043053)=$3.36 \times 10^{-5}$ which is 237 kb from the closest proximal gene DTWD2. Taken together, SNPs residing around exon 4 of contactin 3 (CNTN3) appear to replicate most consistently between Illumina and Perlegen ADHD TDT statistics. SNP rs12488030 is common to both platforms P=$2.51 \times 10^{-3}$ Illumina and P=$4.97 \times 10^{-3}$ Perlegen. There are two supporting SNPs in close proximity also showing significance Illumina: P(rs4073942)=$2.78 \times 10^{-3}$ and P(rs9869828)=$8.61 \times 10^{-3}$ in addition Perlegen: P(rs11915713)=$1.86 \times 10^{-5}$ and P(rs7372975)=$7.59 \times 10^{-5}$

TABLE 5

TDT Analysis of 397 ADHD Cases and Parents from CHOP genotyped on the Illumina HH550 chip.

| CHR | SNP | BP | A1 | A2 | T | U | OR | CHISQ | P |
|---|---|---|---|---|---|---|---|---|---|
| 18 | rs8095193 | 58834095 | 1 | 2 | 167 | 92 | 1.815 | 21.72 | 3.16E−06 |
| 17 | rs4357980 | 13498634 | 1 | 2 | 99 | 174 | 0.569 | 20.6 | 5.65E−06 |
| 18 | rs8091710 | 72897492 | 1 | 2 | 29 | 73 | 0.3973 | 18.98 | 1.32E−05 |
| 14 | rs899116 | 97495185 | 1 | 2 | 101 | 172 | 0.5872 | 18.47 | 1.73E−05 |
| 13 | rs9595945 | 48099556 | 1 | 2 | 245 | 160 | 1.531 | 17.84 | 2.40E−05 |
| 4 | rs1018199 | 47927632 | 1 | 2 | 35 | 80 | 0.4375 | 17.61 | 2.71E−05 |
| 1 | rs3795324 | 157456184 | 2 | 1 | 91 | 157 | 0.5796 | 17.56 | 2.78E−05 |

TABLE 5-continued

TDT Analysis of 397 ADHD Cases and Parents from CHOP genotyped on the Illumina HH550 chip.

| CHR | SNP | BP | A1 | A2 | T | U | OR | CHISQ | P |
|---|---|---|---|---|---|---|---|---|---|
| 3 | rs6444186 | 188156541 | 1 | 2 | 81 | 36 | 2.25 | 17.31 | 3.18E−05 |
| 9 | rs11144627 | 75654927 | 2 | 1 | 46 | 14 | 3.286 | 17.07 | 3.61E−05 |
| 8 | rs1462011 | 108104653 | 1 | 2 | 199 | 125 | 1.592 | 16.9 | 3.94E−05 |
| X | rs5991935 | 100480088 | 1 | 2 | 22 | 59 | 0.3729 | 16.9 | 3.94E−05 |
| 7 | rs1013572 | 78350227 | 1 | 2 | 63 | 118 | 0.5339 | 16.71 | 4.35E−05 |
| 11 | rs952619 | 20316347 | 1 | 2 | 108 | 177 | 0.6102 | 16.71 | 4.37E−05 |
| 4 | rs7689018 | 85116479 | 1 | 2 | 41 | 87 | 0.4713 | 16.53 | 4.79E−05 |
| 18 | rs1943825 | 69128567 | 2 | 1 | 97 | 162 | 0.5988 | 16.31 | 5.37E−05 |
| 4 | rs4696821 | 8473961 | 1 | 2 | 210 | 135 | 1.556 | 16.3 | 5.39E−05 |
| 18 | rs1943823 | 69131624 | 2 | 1 | 157 | 237 | 0.6624 | 16.24 | 5.57E−05 |
| 4 | rs11724347 | 47923023 | 1 | 2 | 26 | 64 | 0.4062 | 16.04 | 6.19E−05 |
| 1 | rs7530899 | 76950752 | 2 | 1 | 89 | 151 | 0.5894 | 16.02 | 6.28E−05 |
| 18 | rs4890560 | 41457783 | 1 | 2 | 93 | 156 | 0.5962 | 15.94 | 6.54E−05 |
| 6 | rs2677099 | 45527900 | 1 | 2 | 220 | 144 | 1.528 | 15.87 | 6.79E−05 |
| 12 | rs11067228 | 113556980 | 2 | 1 | 231 | 153 | 1.51 | 15.84 | 6.88E−05 |
| 6 | rs2790102 | 45540192 | 1 | 2 | 222 | 146 | 1.521 | 15.7 | 7.44E−05 |
| 1 | rs4926757 | 48961624 | 1 | 2 | 192 | 122 | 1.574 | 15.61 | 7.80E−05 |
| 11 | rs17147479 | 84055504 | 1 | 2 | 137 | 79 | 1.734 | 15.57 | 7.93E−05 |
| 17 | rs9913261 | 12026365 | 2 | 1 | 89 | 150 | 0.5933 | 15.57 | 7.96E−05 |
| 9 | rs7041883 | 135352660 | 1 | 2 | 17 | 49 | 0.3469 | 15.52 | 8.19E−05 |
| 12 | rs7309946 | 103478293 | 2 | 1 | 119 | 188 | 0.633 | 15.51 | 8.22E−05 |
| 7 | rs10226468 | 42907176 | 2 | 1 | 144 | 219 | 0.6575 | 15.5 | 8.27E−05 |
| 5 | rs438418 | 2902436 | 2 | 1 | 78 | 36 | 2.167 | 15.47 | 8.37E−05 |
| 8 | rs12682232 | 108078371 | 1 | 2 | 199 | 128 | 1.555 | 15.42 | 8.63E−05 |
| X | rs5956634 | 123092612 | 2 | 1 | 59 | 110 | 0.5364 | 15.39 | 8.74E−05 |
| 7 | rs7786719 | 42850356 | 1 | 2 | 133 | 205 | 0.6488 | 15.34 | 8.99E−05 |
| 6 | rs910586 | 45518290 | 1 | 2 | 221 | 146 | 1.514 | 15.33 | 9.04E−05 |
| 6 | rs9395010 | 44453984 | 1 | 2 | 152 | 91 | 1.67 | 15.31 | 9.11E−05 |
| 14 | rs11844273 | 97489409 | 1 | 2 | 100 | 163 | 0.6135 | 15.09 | 1.02E−04 |
| 2 | rs11904235 | 36288350 | 1 | 2 | 64 | 27 | 2.37 | 15.04 | 1.05E−04 |
| 11 | rs487518 | 131283728 | 1 | 2 | 150 | 225 | 0.6667 | 15 | 1.08E−04 |
| 6 | rs6920606 | 33105652 | 2 | 1 | 164 | 242 | 0.6777 | 14.99 | 1.08E−04 |
| 14 | rs2014525 | 97491178 | 1 | 2 | 109 | 174 | 0.6264 | 14.93 | 1.12E−04 |
| 11 | rs7948111 | 23403649 | 1 | 2 | 65 | 117 | 0.5556 | 14.86 | 1.16E−04 |
| 16 | rs12598067 | 60940038 | 2 | 1 | 65 | 117 | 0.5556 | 14.86 | 1.16E−04 |
| 6 | rs9472494 | 45559814 | 1 | 2 | 223 | 149 | 1.497 | 14.72 | 1.25E−04 |
| 7 | rs533486 | 99085345 | 2 | 1 | 163 | 240 | 0.6792 | 14.71 | 1.25E−04 |
| 8 | rs7835921 | 96345468 | 1 | 2 | 157 | 96 | 1.635 | 14.71 | 1.26E−04 |
| 4 | rs827019 | 8460842 | 2 | 1 | 69 | 122 | 0.5656 | 14.71 | 1.26E−04 |

CHR: Chromosome number,
SNP: SNP identifier,
A1: Minor allele code,
A2: Major allele code,
T: Transmitted minor allele count,
U: Untransmitted allele count,
OR: TDT odds ratio,
CHISQ: TDT chi-square statistic,
P: TDT asymptotic p-value

TABLE 6

Case: Control Analysis of 735 ADHD Cases and 2,298 Unrelated Controls from CHOP genotyped on the Illumina HH550 chip.

| CHR | SNP | BP | A1 | A2 | F_A | F_U | OR | CHISQ | P |
|---|---|---|---|---|---|---|---|---|---|
| 18 | rs16943400 | 23086102 | 1 | 2 | 0.02778 | 0.08875 | 0.2934 | 57.53 | 3.33E−14 |
| 3 | rs7649108 | 166136126 | 1 | 2 | 0.3156 | 0.2497 | 1.386 | 24.88 | 6.11E−07 |
| 6 | rs9390261 | 145283744 | 1 | 2 | 0.02585 | 0.009072 | 2.899 | 24.54 | 7.29E−07 |
| X | rs4609327 | 37790223 | 2 | 1 | 0.1441 | 0.08032 | 1.928 | 24.48 | 7.50E−07 |
| X | rs5917547 | 37803525 | 2 | 1 | 0.1578 | 0.09074 | 1.878 | 24.22 | 8.59E−07 |
| 16 | rs2278656 | 54885245 | 1 | 2 | 0.01443 | 0.04091 | 0.3432 | 22.04 | 2.67E−06 |
| 8 | rs17834541 | 2674349 | 2 | 1 | 0.1083 | 0.1565 | 0.6545 | 21.01 | 4.56E−06 |
| 19 | rs2081051 | 20866811 | 1 | 2 | 0.1382 | 0.1911 | 0.6786 | 21 | 4.60E−06 |
| 19 | rs399686 | 20772798 | 1 | 2 | 0.143 | 0.1962 | 0.6833 | 20.95 | 4.72E−06 |
| X | rs5917937 | 39750534 | 2 | 1 | 0.1195 | 0.06572 | 1.929 | 20.93 | 4.76E−06 |
| 19 | rs10419820 | 20943636 | 2 | 1 | 0.1789 | 0.2357 | 0.7067 | 20.9 | 4.84E−06 |
| X | rs10522011 | 32517409 | 1 | 2 | 0.05924 | 0.02509 | 2.447 | 19.48 | 1.02E−05 |
| 8 | rs11203872 | 17531028 | 2 | 1 | 0.4342 | 0.37 | 1.306 | 19.34 | 1.09E−05 |
| X | rs9633179 | 3535471 | 2 | 1 | 0.1089 | 0.05969 | 1.925 | 19.24 | 1.15E−05 |
| 4 | rs10519629 | 143040375 | 2 | 1 | 0.1864 | 0.1398 | 1.409 | 18.81 | 1.44E−05 |

TABLE 6-continued

Case: Control Analysis of 735 ADHD Cases and 2,298 Unrelated Controls from CHOP genotyped on the Illumina HH550 chip.

| CHR | SNP | BP | A1 | A2 | F_A | F_U | OR | CHISQ | P |
|---|---|---|---|---|---|---|---|---|---|
| 19 | rs7253306 | 20951939 | 2 | 1 | 0.219 | 0.2759 | 0.736 | 18.77 | 1.48E−05 |
| 13 | rs9569383 | 55299477 | 1 | 2 | 0.1415 | 0.1909 | 0.6984 | 18.64 | 1.58E−05 |
| 12 | rs12229174 | 62532933 | 1 | 2 | 0.06054 | 0.03502 | 1.776 | 18.56 | 1.64E−05 |
| 19 | rs6511169 | 20893589 | 1 | 2 | 0.1461 | 0.1961 | 0.7014 | 18.51 | 1.69E−05 |
| 11 | rs10833476 | 21190445 | 1 | 2 | 0.1224 | 0.08502 | 1.502 | 18.48 | 1.72E−05 |
| 2 | rs1821659 | 212064488 | 2 | 1 | 0.3109 | 0.2527 | 1.334 | 18.15 | 2.05E−05 |
| X | rs2480443 | 53212284 | 2 | 1 | 0.06525 | 0.02994 | 2.262 | 18.1 | 2.09E−05 |
| 7 | rs1486173 | 45965025 | 1 | 2 | 0.1131 | 0.07764 | 1.515 | 17.91 | 2.32E−05 |
| 15 | rs4381545 | 93039961 | 2 | 1 | 0.2296 | 0.18 | 1.358 | 17.8 | 2.45E−05 |
| 7 | rs10265665 | 96175055 | 1 | 2 | 0.0619 | 0.0365 | 1.742 | 17.79 | 2.46E−05 |
| 10 | rs11593585 | 44391199 | 1 | 2 | 0.1286 | 0.09093 | 1.475 | 17.69 | 2.60E−05 |
| X | rs4134188 | 17474194 | 1 | 2 | 0.1016 | 0.05571 | 1.917 | 17.62 | 2.69E−05 |
| 4 | rs11131363 | 63013616 | 2 | 1 | 0.2643 | 0.212 | 1.335 | 17.6 | 2.72E−05 |
| 19 | rs1469402 | 20738115 | 2 | 1 | 0.145 | 0.1934 | 0.7075 | 17.52 | 2.85E−05 |
| 11 | rs12279152 | 133861485 | 1 | 2 | 0.02653 | 0.01139 | 2.365 | 17.43 | 2.98E−05 |
| X | rs5957334 | 119125665 | 2 | 1 | 0.06667 | 0.03136 | 2.206 | 17.13 | 3.49E−05 |
| X | rs6632558 | 36075450 | 2 | 1 | 0.0812 | 0.04176 | 2.028 | 16.94 | 3.85E−05 |
| 1 | rs2057594 | 117348535 | 1 | 2 | 0.2483 | 0.1983 | 1.335 | 16.89 | 3.96E−05 |
| 8 | rs17834523 | 2672777 | 1 | 2 | 0.09592 | 0.1367 | 0.6699 | 16.84 | 4.06E−05 |
| 7 | rs10485959 | 78702412 | 2 | 1 | 0.3007 | 0.3595 | 0.7659 | 16.83 | 4.09E−05 |
| X | rs5945330 | 152438289 | 2 | 1 | 0.08807 | 0.04698 | 1.959 | 16.63 | 4.55E−05 |
| 3 | rs16854851 | 145238402 | 1 | 2 | 0.02381 | 0.009916 | 2.435 | 16.62 | 4.56E−05 |
| 8 | rs2237826 | 17519195 | 2 | 1 | 0.4355 | 0.376 | 1.28 | 16.59 | 4.65E−05 |
| X | rs16987407 | 35968032 | 2 | 1 | 0.1041 | 0.05857 | 1.868 | 16.5 | 4.87E−05 |
| X | rs4089885 | 22878045 | 2 | 1 | 0.1193 | 0.07027 | 1.792 | 16.47 | 4.94E−05 |
| 1 | rs2024766 | 181385290 | 2 | 1 | 0.5027 | 0.4424 | 1.274 | 16.45 | 4.99E−05 |
| 4 | rs9312518 | 173526549 | 1 | 2 | 0.4639 | 0.4042 | 1.276 | 16.45 | 5.00E−05 |
| 4 | rs9997484 | 173517324 | 1 | 2 | 0.4639 | 0.4042 | 1.276 | 16.45 | 5.00E−05 |
| 17 | rs4338847 | 7870502 | 1 | 2 | 0.3102 | 0.3679 | 0.7725 | 16.35 | 5.28E−05 |
| 12 | rs17497206 | 113000660 | 2 | 1 | 0.1537 | 0.2011 | 0.7219 | 16.33 | 5.32E−05 |

CHR: Chromosome,
SNP: SNP ID,
BP: Physical position (base-pair),
A1: Minor allele name (based on whole sample),
F_A: Frequency of this allele in cases,
F_U: Frequency of this allele in controls,
A2: Major allele name,
OR: Estimated odds ratio (for A1, i.e. A2 is reference),
CHISQ: Basic allelic test chi-square (1df),
P: Asymptotic p-value for this test.

TABLE 7

TDT Analysis of 623 ADHD Cases and Parents from IMAGE genotyped on the Perlegen platform.

| CHR | SNP | BP | A1 | A2 | T | U | OR | CHISQ | P |
|---|---|---|---|---|---|---|---|---|---|
| 12 | rs3782309 | 26750663 | 1 | 2 | 172 | 99 | 1.737 | 19.66 | 9.23E−06 |
| 5 | rs17144308 | 117965870 | 2 | 1 | 244 | 352 | 0.6932 | 19.57 | 9.70E−06 |
| 2 | rs7609261 | 80530821 | 2 | 1 | 199 | 297 | 0.67 | 19.36 | 1.08E−05 |
| 3 | rs1344870 | 21282405 | 2 | 1 | 16 | 52 | 0.3077 | 19.06 | 1.27E−05 |
| 18 | rs7244637 | 17876224 | 1 | 2 | 134 | 215 | 0.6233 | 18.8 | 1.45E−05 |
| 1 | rs3850879 | 48004718 | 1 | 2 | 226 | 143 | 1.58 | 18.67 | 1.56E−05 |
| 14 | rs2295426 | 58446208 | 2 | 1 | 209 | 307 | 0.6808 | 18.61 | 1.60E−05 |
| 16 | rs7204253 | 5576184 | 2 | 1 | 114 | 189 | 0.6032 | 18.56 | 1.64E−05 |
| 4 | rs1378945 | 25382295 | 2 | 1 | 212 | 310 | 0.6839 | 18.4 | 1.79E−05 |
| 3 | rs11915713 | 74568983 | 1 | 2 | 176 | 266 | 0.6617 | 18.33 | 1.86E−05 |
| 12 | rs11830382 | 41718893 | 2 | 1 | 198 | 122 | 1.623 | 18.05 | 2.15E−05 |
| 12 | rs4761641 | 93525817 | 2 | 1 | 137 | 215 | 0.6372 | 17.28 | 3.22E−05 |
| 5 | rs2043053 | 117958083 | 2 | 1 | 126 | 201 | 0.6269 | 17.2 | 3.36E−05 |
| 18 | rs12965880 | 22313077 | 2 | 1 | 235 | 333 | 0.7057 | 16.91 | 3.92E−05 |
| 9 | rs17306197 | 97862011 | 1 | 2 | 162 | 96 | 1.688 | 16.88 | 3.97E−05 |
| 8 | rs17668689 | 96254526 | 1 | 2 | 216 | 310 | 0.6968 | 16.8 | 4.16E−05 |
| 2 | rs4852567 | 80556890 | 2 | 1 | 206 | 298 | 0.6913 | 16.79 | 4.17E−05 |
| 13 | rs1002468 | 93085569 | 1 | 2 | 287 | 197 | 1.457 | 16.74 | 4.30E−05 |
| 1 | rs10873925 | 77234323 | 2 | 1 | 305 | 212 | 1.439 | 16.73 | 4.31E−05 |
| 16 | rs12596741 | 17345435 | 1 | 2 | 228 | 324 | 0.7037 | 16.7 | 4.39E−05 |
| 9 | rs2991298 | 3284851 | 2 | 1 | 81 | 142 | 0.5704 | 16.69 | 4.41E−05 |
| 14 | rs1427324 | 58434446 | 1 | 2 | 206 | 297 | 0.6936 | 16.46 | 4.96E−05 |
| 10 | rs11258682 | 13951273 | 1 | 2 | 204 | 130 | 1.569 | 16.4 | 5.14E−05 |

TABLE 7-continued

TDT Analysis of 623 ADHD Cases and Parents from IMAGE genotyped on the Perlegen platform.

| CHR | SNP | BP | A1 | A2 | T | U | OR | CHISQ | P |
|---|---|---|---|---|---|---|---|---|---|
| 4 | rs10520276 | 175420068 | 2 | 1 | 216 | 140 | 1.543 | 16.22 | 5.63E−05 |
| 1 | rs17375519 | 179499648 | 1 | 2 | 75 | 133 | 0.5639 | 16.17 | 5.78E−05 |
| 1 | rs10800069 | 163296159 | 1 | 2 | 232 | 327 | 0.7095 | 16.14 | 5.87E−05 |
| 7 | rs13340504 | 75277632 | 1 | 2 | 142 | 82 | 1.732 | 16.07 | 6.10E−05 |
| 2 | rs6543239 | 104056246 | 2 | 1 | 251 | 349 | 0.7192 | 16.01 | 6.31E−05 |
| 2 | rs4664452 | 162762970 | 1 | 2 | 30 | 6 | 5 | 16 | 6.33E−05 |
| 4 | rs16889099 | 13341184 | 2 | 1 | 48 | 96 | 0.5 | 16 | 6.33E−05 |
| 5 | rs12520147 | 2000122 | 1 | 2 | 158 | 237 | 0.6667 | 15.8 | 7.04E−05 |
| 11 | rs10400283 | 23523711 | 1 | 2 | 222 | 314 | 0.707 | 15.79 | 7.07E−05 |
| 4 | rs1378946 | 25382548 | 1 | 2 | 197 | 284 | 0.6937 | 15.74 | 7.28E−05 |
| 3 | rs7372975 | 74602140 | 2 | 1 | 169 | 250 | 0.676 | 15.66 | 7.59E−05 |
| 17 | rs11654470 | 74388926 | 2 | 1 | 82 | 141 | 0.5816 | 15.61 | 7.79E−05 |
| 3 | rs9878591 | 121464488 | 1 | 2 | 107 | 173 | 0.6185 | 15.56 | 8.01E−05 |
| 12 | rs1553953 | 28724544 | 1 | 2 | 76 | 133 | 0.5714 | 15.55 | 8.06E−05 |
| 11 | rs7121790 | 45021541 | 1 | 2 | 171 | 252 | 0.6786 | 15.51 | 8.20E−05 |
| 12 | rs1452231 | 83750252 | 2 | 1 | 223 | 314 | 0.7102 | 15.42 | 8.60E−05 |
| 7 | rs194847 | 103560404 | 1 | 2 | 347 | 251 | 1.382 | 15.41 | 8.65E−05 |
| 2 | rs11902138 | 80565100 | 1 | 2 | 173 | 254 | 0.6811 | 15.37 | 8.86E−05 |
| 16 | rs12932714 | 80320240 | 1 | 2 | 150 | 226 | 0.6637 | 15.36 | 8.88E−05 |
| 1 | rs1015144 | 200004976 | 2 | 1 | 204 | 291 | 0.701 | 15.29 | 9.22E−05 |
| 22 | rs6009441 | 47873456 | 1 | 2 | 107 | 172 | 0.6221 | 15.14 | 9.97E−05 |
| 8 | rs4734069 | 104169047 | 1 | 2 | 275 | 191 | 1.44 | 15.14 | 9.97E−05 |
| 20 | rs2024946 | 61678306 | 2 | 1 | 112 | 61 | 1.836 | 15.03 | 1.06E−04 |

CHR: Chromosome number,
SNP: SNP identifier,
A1: Minor allele code,
A2: Major allele code,
T: Transmitted minor allele count,
U: Untransmitte allele count,
OR: TDT odds ratio,
CHISQ: TDT chi-square statistic,
P: TDT asymptotic p-value Study Criteria for Inclusion in IMAGE
Proband diagnosis: combined subtype ADHD.
Children aged 6-17 years (inclusive).
One or more sibling(s) in the same age range.
Both parents available to provide DNA sample or one parent available plus two or more siblings.
IQ above 70.
Free of single-gene disorders known to be associated with ADHD (e.g. fragile-X, phenylketonuria, hypercalcaemia, thyroid hormone resistance).
Free of neurological disease and damage (e.g. hemiplegia and other cerebral palsies, epilepsy, hydrocephalus, post-encephalitic syndromes, psychosis, sensorimotor handicaps).
Living at home with at least one biological parent and one full sibling.
Not meeting criteria for autism or Asperger's syndrome.
Study Criteria for Inclusion in IMAGE II
Proband diagnosis: ADHD according to DSM-IV-TR
Semi-structured diagnostic interview: KSADS-PL or Kinder-DIPS
Child Behavior Checklist, Conners parent and teacher Scales or German Teachers Report on ADHD symptoms according to DSM-IV
Children aged 6-18 years (index patients older than 8 years).
IQ above 70; birth weight >2000 g; no major medical events during pregnancy; no drug abuse in mother during pregnancy
Free of single-gene disorders known to be associated with ADHD (e.g. fragile-X, phenylketonuria, hypercalcaemia, thyroid hormone resistance).
Free of neurological disease and damage (e.g. hemiplegia and other cerebral palsies, epilepsy, hydrocephalus, post-encephalitic syndromes, motor neuron disorder etc.).
Not meeting criteria for autism or Asperger's syndrome, schizophrenia, bipolar disorder, primary major depressive episode, and anxiety disorder, Tourette's Syndrome.
Controls for IMAGE II
The control subjects used were drawn from Affymetrix 6.0 genotyped subjects from the NIMH genetics repository. They had been collected through a US Nationally representative survey panel (of approximately 60,000 adult individuals at any one time, with constant turnover) ascertained via random digit dialing. Participants were screened for psychosis and bipolar disorder. Control participants were not screened for ADHD. A blood sample was collected via a US national phlebotomy service. Control participants gave written consent for their biological materials to be used for medical research at the discretion of NIMH. Controls were genotyped using the Affymetrix 6.0 array, at the Broad Institute National Center for Genotyping and Analysis. Genotype calls were made with the BIRDSEED program, a module of the BIRDSUITE package.
Network Analysis
We used Cytoscape Software[47] to identified 228 genes within 2 degrees of relation to 8 GRM genes based on the merged human interactome. We clustered this network of genes into 17 distinct modular clusters based solely on network topology using the ClusterViz plug in for the software using the FAG-EC algorithm with default parameters. Component genes of each of the 17 modules were submitted to DAVID[44] to assess the significance of functional enrichment using *Homo sapiens* GO annotations.
The following examples are provided to illustrate certain embodiments of the invention. They are not intended to limit the invention in any way.

Example I

Metabotropic Glutamate Receptor Gene Alterations Associated with ADHD

Several rare recurrent CNVs have been identified that are overrepresented in multiple independent ADHD cohorts that impact genes involved in glutamatergic neurotransmission, an important mediator for the developing brain and normal brain function. These results implicate variations involving glutamatergic gene networks of the brain as contributors to the genetic susceptibility of ADHD.

Study Participants

The discovery cohort included a total of 1,013 ADHD cases of Northern European descent genotyped at Children's Hospital of Philadelphia (CHOP). This consisted of 664 cases without parents and 349 cases from complete trios recruited at CHOP (See Tables 8 and 9).

TABLE 8

Clinical Demographics of Study Participants.

| ADHD Cohort | N | ADHD subjects Age range | Ancestry | ADHD ascertainment |
|---|---|---|---|---|
| CHOP ADHD trios | 349 | 6-18 | European | K-SADS-IVR |
| CHOP ADHD cases | 664 | 6-18 | European | Clinical ADHD diagnosis & treatment with ADHD meds; K-SADS-IVR on majority |
| NIMH ADHD trios | 128 | 6-12 | European | DICA; Conners Scales |
| UTAH cases | 90 | 19-60 | European | WRAADDS, WURS, PRS, strict DSM-IV criteria, including age of onset before 7 |
| IMAGE ADHD trios | 642 | 6-17 | European | PACS, Conners, SDQ, WISC |
| IMAGE II ADHD trios | 787 | 5-14 | European | K-SADS German version, Kinder-DIPS, Conners parent and teacher scales, WISC, K-ABC |
| PUWMa trios | 864 | 6-18 | European | K-SADS |

PACS: Parental Account of Child Symptoms;
Conners: Behavioral rating scales;
SDQ: Strength and Difficulties Questionnaire;
WISC: Wechsler Intelligence Scale for Children (WISC-IV);
KSADS-IVR: Schedule for Affective Disorders and Schizophrenia for School-Age Children-IVR;
DICA: Diagnostic Interview for Children and Adolescents;
Kinder-DIPS: Diagnostic Interview for Psychiatric Disorders in Children,
K-ABC: Kaufman-ABC intelligence scale.
WRAADDS = Wender-Reimherr Adult Attention Deficit Disorder Scale;
WURS = Wender Utah Rating Scale;
PRS = Parent Rating Scale.

TABLE 9

K-SADS ADHD Severity of of CHOP Study Participants in Inattentive, Impulsive, and Hyperactive Domains.

| Diagnostic Criteria | Score 1 | Score 2 | Score 3 | Score 4 |
|---|---|---|---|---|
| Often Careless | 7 | 40 | 372 | 81 |
| Loses Things | 18 | 126 | 277 | 79 |
| Difficulty Finishing | 16 | 90 | 311 | 83 |
| Listening | 10 | 22 | 320 | 148 |
| Concentration* | 2 | 25 | 337 | 135 |
| Distracted | 1 | 10 | 307 | 182 |
| Organizing | 19 | 79 | 304 | 98 |
| Avoiding | 19 | 55 | 278 | 148 |
| Forgetful | 19 | 75 | 290 | 116 |
| Interrupts | 28 | 73 | 305 | 94 |
| Acts Before Thinking | 28 | 112 | 283 | 77 |
| Shifts Activities | 72 | 134 | 247 | 47 |
| Blurts† | 135 | 82 | 232 | 48 |
| Difficulty Waiting Turn | 80 | 172 | 200 | 48 |
| Hyperactive | 53 | 127 | 227 | 93 |
| Fidgeting | 15 | 47 | 301 | 137 |
| Difficulty Staying Seated | 45 | 80 | 287 | 88 |
| On the Go | 49 | 89 | 255 | 107 |
| Talks Excess | 37 | 77 | 255 | 131 |
| Difficulty Playing Quietly | 98 | 120 | 233 | 49 |

*Concentration 1 record missing
†Blurts 3 records missing.
Scores 1 and 2 means that symptoms are within the normal range while scores 3 and 4 are excessive.

To address replication, we accessed the IMAGE cohorts which are a part of the Genetic Association Information Network (GAIN). There were 624 IMAGE samples that met quality control criteria for the study. Access to these genotypes and intensity data for IMAGE was provided through the database of Genotypes and Phenotypes (dbGaP). The PUWMa consortium from University of California at Los Angeles, Massachusetts General Hospital, and Washington University St. Louis contributed 864 ADHD cases and 1,258 parents. The IMAGE II consortium contributed 787 ADHD cases and 898 unrelated controls. Furthermore, 128 cases recruited at the NIMH and 90 cases recruited at The University of Utah also served for replication. The DNA samples from CHOP, NIMH, and Utah cohorts were genotyped using the Illumina Infinium HumanHap550K BeadChip at CHOP. The IMAGE cohort was genotyped using the Perlegen 600K platform. The PUWMa cohort was genotyped on the Illumina 1M BeadChip. The IMAGE II cohort was genotyped on the Affymetrix 5.0 array. To manage differences in CNV detection between arrays we used controls genotyped on platforms matching the case platforms, including: 4,105 Illumina 550k from CHOP, 3,297 Perlegen 600k from GAIN psoriasis and depression projects, 3,469 Illumina 1M from PUWMa parents and SAGE, and 2,456 Affymetrix 5.0 and 6.0 controls from the NIMH genetics repository and AGRE parents.

CNV Size and Number in Cases and Controls

To search for novel CNVs we analyzed the 1,013 CHOP cases as a discovery cohort in comparison with 4,105 control children, all of whom were of European ancestry. Data from the IMAGE, PUWMa, IMAGE II, NIMH, and Utah cohorts were used for replication, together with an independent control cohort of 9,222 genotyped on the same platforms. Thus, the control CNV frequency is robustly characterized in multiple large independent cohorts, based on the Illumina, Perlegen, and Affymetrix platforms. We note that of the 2,713 (934 cases) IMAGE samples available in dbGaP, 1,886 (624 cases) met strictly established data quality thresholds for CNVs.

Figure 8:
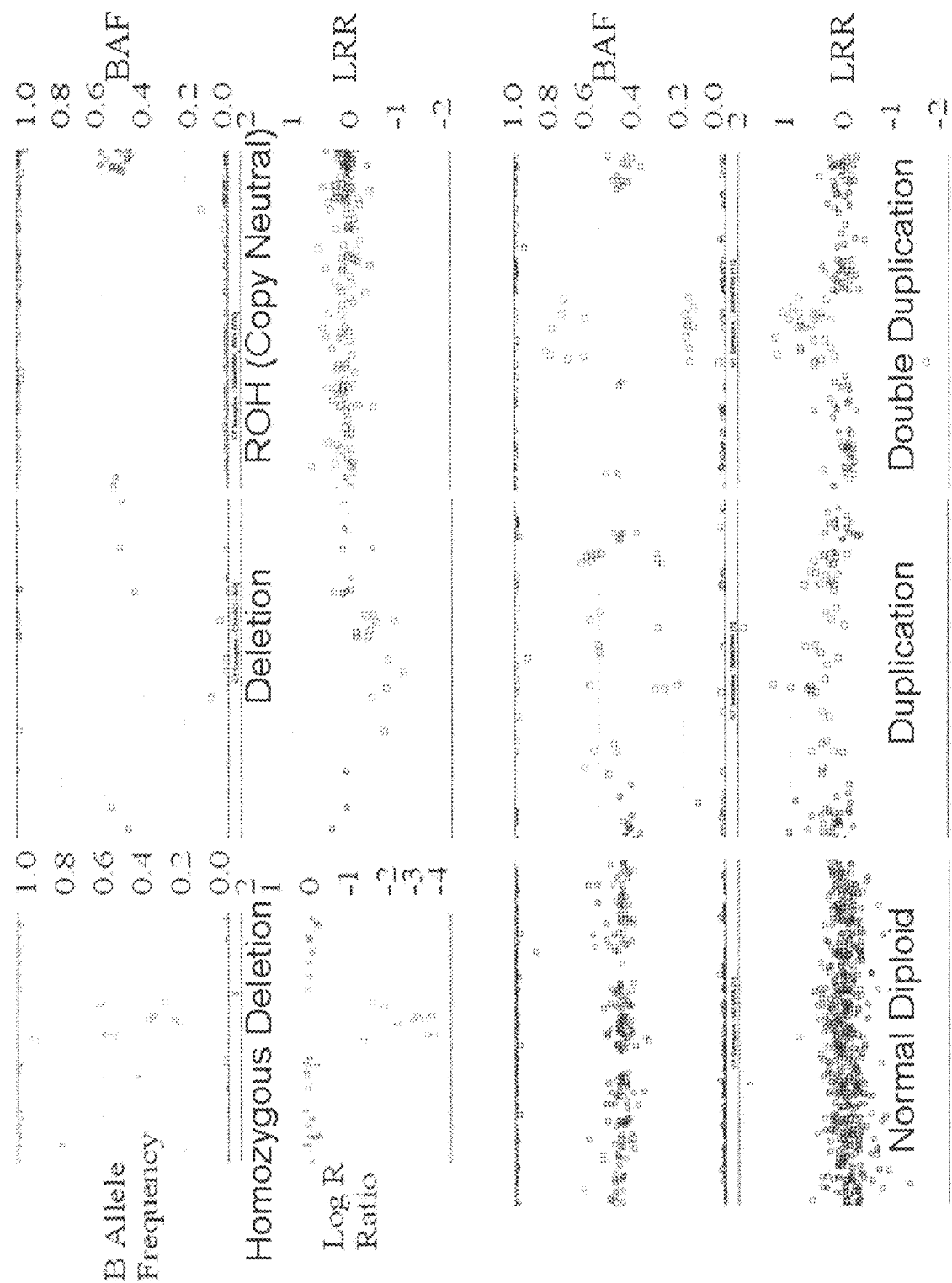
FIG. 8. Examples of CNV observance based on B-allele frequency (BAF) and Log R Ratio (LRR).

The PennCNV software was used to produce CNV calls for cases and controls as previously described[10]. The CNV frequency of the subjects who met quality standards, which included removing substantial outliers in the count CNV call quality metric that deviated exponentially from the distribution of the majority of the cohort, resulted in 93% of subjects having 8-45 CNV calls (FIG. 1). We called four different copy number states, including 3,172 homozygous deletions (copy number, or CN=0), 27,810 hemizygous deletions (CN=1), 14,806 one copy duplications (CN=3), and 581 two copy duplications (CN=4). FIG. 8 shows an example of raw Illumina data as viewed in the BeadStudio software and the resulting CNV call. The CNV calls spanned from 3 to 598 SNPs, with an average of 14 SNPs per CNV call, with the largest CNV of 2.2 Mb and an average CNV size of 62 kb. Variable probe coverage allows for detection of CNVs down to a small physical size, provided at least 3 SNPs are present, and the CNVs were experimentally validated using qPCR.

Control individuals examined also had 93% of subjects with 8-45 CNV calls (FIG. 1). Among the CNV calls, we identified 4,471 homozygous deletions (CN=0), 49,726 hemizygous deletions (CN=1), 27,032 one copy duplications (CN=3), and 1,480 two copy duplications (CN=4). The CNV calls spanned from 3 to 708 SNPs, with an average of 12.8 SNPs per CNV call, with the largest CNV of 2.9 Mb and an average CNV size of 53.6 kb.

SNP Association Testing

We performed GWA analysis on the discovery cohort, however, we did not detect any single SNP genotype association signals that met statistical criteria for genome-wide significance ($p<5\times10^{-8}$) (see Tables 5, 6, and 7). However, we did observe evidence of replication of several terminal exon SNPs within the GFOD1 gene in the CHOP families, using TDT (P-value range=$8\times10^{-4}$-$1\times10^{-2}$, for rs1866863, rs9370020, rs2254292, and rs2439565). We additionally report observed significance for other SNPs reported previously (Lesch, et al. 2008; Zhou, et al. 2008) with converging evidence in Table 10.

TABLE 10

SNP GWAS Significance of Top Ranked ADHD Associated SNPs Reported by Lesch and Zhou. A) ADHD TDT CHOP Illumina 550k data; B) ADHD Case: Control CHOP Illumina 550k data; C) ADHD IMAGE Perlegen 600k data.

A)

| CHR | SNP | BP | A1 | A2 | T | U | OR | CHISQ | P |
|---|---|---|---|---|---|---|---|---|---|
| 2 | rs2241685 | 1896290 | 1 | 2 | 72 | 62 | 1.161 | 0.7463 | 0.3877 |
| 2 | rs13395022 | 79793915 | 2 | 1 | 136 | 136 | 1 | 0 | 1 |
| 2 | rs2587695 | 120038047 | 1 | 2 | 183 | 197 | 0.9289 | 0.5158 | 0.4726 |
| 2 | rs2242073 | 208819551 | 2 | 1 | 108 | 106 | 1.019 | 0.01869 | 0.8913 |
| 2 | rs1110998 | 217169458 | 1 | 2 | 175 | 159 | 1.101 | 0.7665 | 0.3813 |
| 3 | rs10510238 | 2876647 | 2 | 1 | 84 | 93 | 0.9032 | 0.4576 | 0.4987 |
| 3 | rs9879164 | 54040611 | 2 | 1 | 185 | 198 | 0.9343 | 0.4413 | 0.5065 |
| 3 | rs2084358 | 57457928 | 2 | 1 | 182 | 198 | 0.9192 | 0.6737 | 0.4118 |
| 3 | rs10490808 | 59939739 | 2 | 1 | 175 | 204 | 0.8578 | 2.219 | 0.1363 |
| 3 | rs10510850 | 60542142 | 1 | 2 | 90 | 83 | 1.084 | 0.2832 | 0.5946 |
| 4 | rs755403 | 6507714 | 2 | 1 | 195 | 180 | 1.083 | 0.6 | 0.4386 |
| 4 | rs10516182 | 7143981 | 2 | 1 | 155 | 169 | 0.9172 | 0.6049 | 0.4367 |
| 4 | rs7697323 | 7801488 | 1 | 2 | 180 | 222 | 0.8108 | 4.388 | 0.03619 |
| 5 | rs173754 | 65102081 | 1 | 2 | 218 | 202 | 1.079 | 0.6095 | 0.435 |
| 5 | rs258082 | 66166352 | 1 | 2 | 199 | 205 | 0.9707 | 0.08911 | 0.7653 |
| 6 | rs160666 | 2719051 | 2 | 1 | 179 | 181 | 0.989 | 0.01111 | 0.9161 |
| 6 | rs2842643 | 41758714 | 2 | 1 | 180 | 149 | 1.208 | 2.921 | 0.08744 |
| 6 | rs3799977 | 44945334 | 2 | 1 | 209 | 183 | 1.142 | 1.724 | 0.1891 |
| 6 | rs8180608 | 89064414 | 2 | 1 | 178 | 218 | 0.8165 | 4.04 | 0.04442 |
| 6 | rs1358601 | 91532294 | 1 | 2 | 180 | 181 | 0.9945 | 0.00277 | 0.958 |
| 6 | rs6921403 | 154156020 | 2 | 1 | 86 | 90 | 0.9556 | 0.09091 | 0.763 |
| 7 | rs2237349 | 28536203 | 2 | 1 | 176 | 191 | 0.9215 | 0.6131 | 0.4336 |
| 7 | rs2002865 | 154132035 | 2 | 1 | 134 | 157 | 0.8535 | 1.818 | 0.1776 |
| 8 | rs6991017 | 5508780 | 2 | 1 | 127 | 126 | 1.008 | 0.003953 | 0.9499 |
| 8 | rs2248529 | 14657354 | 1 | 2 | 188 | 190 | 0.9895 | 0.01058 | 0.9181 |
| 8 | rs4961315 | 142110882 | 2 | 1 | 186 | 152 | 1.224 | 3.42 | 0.06441 |
| 9 | rs2418326 | 114759028 | 1 | 2 | 141 | 142 | 0.993 | 0.003534 | 0.9526 |
| 9 | rs2502731 | 128056111 | 2 | 1 | 170 | 178 | 0.9551 | 0.1839 | 0.668 |
| 14 | rs10483393 | 31530235 | 1 | 2 | 146 | 137 | 1.066 | 0.2862 | 0.5927 |
| 15 | rs2556560 | 42609135 | 2 | 1 | 169 | 171 | 0.9883 | 0.01176 | 0.9136 |
| 16 | rs8060494 | 78808972 | 2 | 1 | 190 | 174 | 1.092 | 0.7033 | 0.4017 |
| 17 | rs4790372 | 2701606 | 2 | 1 | 163 | 169 | 0.9645 | 0.1084 | 0.7419 |
| 17 | rs12453316 | 69027654 | 1 | 2 | 177 | 179 | 0.9888 | 0.01124 | 0.9156 |
| 19 | rs997669 | 34996323 | 2 | 1 | 201 | 183 | 1.098 | 0.8438 | 0.3583 |
| 20 | rs1555322 | 33312595 | 1 | 2 | 94 | 79 | 1.19 | 1.301 | 0.2541 |

B)

| CHR | SNP | BP | A1 | F_A | F_U | A2 | OR | CHISQ | P |
|---|---|---|---|---|---|---|---|---|---|
| 2 | rs2241685 | 1896290 | 1 | 0.09116 | 0.09283 | 2 | 0.9802 | 0.03733 | 0.8468 |
| 2 | rs13395022 | 79793915 | 2 | 0.2088 | 0.2095 | 1 | 0.9961 | 0.002865 | 0.9573 |
| 2 | rs2587695 | 120038047 | 1 | 0.4973 | 0.4922 | 2 | 1.021 | 0.1161 | 0.7333 |
| 2 | rs2242073 | 208819551 | 2 | 0.1605 | 0.1568 | 1 | 1.029 | 0.1216 | 0.7273 |
| 2 | rs1110998 | 217169458 | 1 | 0.3116 | 0.2928 | 2 | 1.093 | 1.886 | 0.1697 |
| 3 | rs10510238 | 2876647 | 2 | 0.1293 | 0.1376 | 1 | 0.9304 | 0.6621 | 0.4158 |
| 3 | rs9879164 | 54040611 | 2 | 0.4218 | 0.4359 | 1 | 0.9441 | 0.9084 | 0.3406 |
| 3 | rs2084358 | 57457928 | 1 | 0.5184 | 0.4722 | 2 | 1.203 | 9.597 | 0.001949 |
| 3 | rs10490808 | 59939739 | 2 | 0.4068 | 0.4266 | 1 | 0.9218 | 1.8 | 0.1797 |

TABLE 10-continued

SNP GWAS Significance of Top Ranked ADHD Associated SNPs Reported by
Lesch and Zhou. A) ADHD TDT CHOP Illumina 550k data; B) ADHD Case:
Control CHOP Illumina 550k data; C) ADHD IMAGE Perlegen 600k data.

| 3 | rs10510850 | 60542142 | 1 | 0.1211 | 0.1116 | 2 | 1.097 | 1.001 | 0.3172 |
|---|---|---|---|---|---|---|---|---|---|
| 4 | rs755403 | 6507714 | 2 | 0.3985 | 0.3973 | 1 | 1.005 | 0.007242 | 0.9322 |
| 4 | rs10516182 | 7143981 | 2 | 0.2801 | 0.2954 | 1 | 0.9279 | 1.274 | 0.259 |
| 4 | rs7697323 | 7801488 | 1 | 0.3782 | 0.38 | 2 | 0.9927 | 0.0142 | 0.9051 |
| 5 | rs173754 | 65102081 | 1 | 0.4925 | 0.4915 | 2 | 1.004 | 0.004285 | 0.9478 |
| 5 | rs258082 | 66166352 | 1 | 0.4619 | 0.4521 | 2 | 1.04 | 0.4342 | 0.5099 |
| 6 | rs160666 | 2719051 | 2 | 0.2857 | 0.3025 | 1 | 0.9222 | 1.515 | 0.2183 |
| 6 | rs2842643 | 41758714 | 2 | 0.2932 | 0.2909 | 1 | 1.011 | 0.02797 | 0.8672 |
| 6 | rs3799977 | 44945334 | 2 | 0.4306 | 0.4076 | 1 | 1.099 | 2.452 | 0.1174 |
| 6 | rs8180608 | 89064414 | 2 | 0.4101 | 0.4441 | 1 | 0.8703 | 5.265 | 0.02176 |
| 6 | rs1358601 | 91532294 | 1 | 0.3852 | 0.3846 | 2 | 1.003 | 0.002076 | 0.9637 |
| 6 | rs6921403 | 154156020 | 2 | 0.1373 | 0.1405 | 1 | 0.9736 | 0.09408 | 0.7591 |
| 7 | rs2237349 | 28536203 | 2 | 0.4109 | 0.4082 | 1 | 1.011 | 0.03276 | 0.8564 |
| 7 | rs2002865 | 154132035 | 2 | 0.2075 | 0.217 | 1 | 0.9445 | 0.6065 | 0.4361 |
| 8 | rs6991017 | 5508780 | 2 | 0.1891 | 0.1873 | 1 | 1.012 | 0.02315 | 0.8791 |
| 8 | rs2248529 | 14657354 | 1 | 0.3604 | 0.363 | 2 | 0.9888 | 0.03305 | 0.8557 |
| 8 | rs4961315 | 142110882 | 2 | 0.2959 | 0.2995 | 1 | 0.983 | 0.06846 | 0.7936 |
| 9 | rs2418326 | 114759028 | 1 | 0.2534 | 0.252 | 2 | 1.007 | 0.01179 | 0.9135 |
| 9 | rs2502731 | 128056111 | 2 | 0.3626 | 0.3508 | 1 | 1.053 | 0.6767 | 0.4107 |
| 14 | rs10483393 | 31530235 | 1 | 0.2272 | 0.2203 | 2 | 1.041 | 0.3146 | 0.5749 |
| 15 | rs2556560 | 42609135 | 2 | 0.419 | 0.4215 | 1 | 0.9899 | 0.02811 | 0.8668 |
| 16 | rs8060494 | 78808972 | 2 | 0.3215 | 0.3228 | 1 | 0.9943 | 0.008131 | 0.9282 |
| 17 | rs4790372 | 2701606 | 2 | 0.3014 | 0.3112 | 1 | 0.9546 | 0.5122 | 0.4742 |
| 17 | rs12453316 | 69027654 | 1 | 0.3612 | 0.3662 | 2 | 0.9788 | 0.1193 | 0.7298 |
| 19 | rs997669 | 34996323 | 2 | 0.4023 | 0.3876 | 1 | 1.064 | 1.025 | 0.3114 |
| 20 | rs1555322 | 33312595 | 1 | 0.1279 | 0.1277 | 2 | 1.002 | 0.0004034 | 0.984 |

C)

| CHR | SNP | BP | A1 | A2 | T | U | OR | CHISQ | P |
|---|---|---|---|---|---|---|---|---|---|
| 1 | rs2281597 | 34132445 | 0 | 2 | 0 | 0 | NA | NA | NA |
| 1 | rs642969 | 197590139 | 0 | 2 | 0 | 0 | NA | NA | NA |
| 2 | rs2587695 | 120038287 | 1 | 2 | 320 | 294 | 1.088 | 1.101 | 0.2941 |
| 2 | rs2242073 | 208702290 | 2 | 1 | 185 | 182 | 1.016 | 0.02452 | 0.8756 |
| 3 | rs10510850 | 60542142 | 1 | 2 | 109 | 115 | 0.9478 | 0.1607 | 0.6885 |
| 3 | rs17233461 | 125807474 | 2 | 1 | 305 | 322 | 0.9472 | 0.4609 | 0.4972 |
| 4 | rs755403 | 6440543 | 2 | 1 | 296 | 278 | 1.065 | 0.5645 | 0.4525 |
| 4 | rs3857174 | 7089831 | 2 | 1 | 202 | 217 | 0.9309 | 0.537 | 0.4637 |
| 4 | rs7697323 | 7734317 | 1 | 2 | 269 | 278 | 0.9676 | 0.1481 | 0.7004 |
| 5 | rs1457720 | 110998762 | 2 | 1 | 247 | 260 | 0.95 | 0.3333 | 0.5637 |
| 6 | rs160666 | 2719051 | 2 | 1 | 248 | 262 | 0.9466 | 0.3843 | 0.5353 |
| 6 | rs3799977 | 44945334 | 2 | 1 | 302 | 282 | 1.071 | 0.6849 | 0.4079 |
| 6 | rs6921403 | 154105599 | 2 | 1 | 149 | 150 | 0.9933 | 0.003344 | 0.9539 |
| 8 | rs6991017 | 5508780 | 2 | 1 | 193 | 191 | 1.01 | 0.01042 | 0.9187 |
| 9 | rs2418326 | 116719295 | 1 | 2 | 236 | 210 | 1.124 | 1.516 | 0.2183 |
| 9 | rs2416606 | 119862757 | 2 | 1 | 264 | 262 | 1.008 | 0.007605 | 0.9305 |
| 10 | rs16928529 | 72652991 | 2 | 1 | 277 | 312 | 0.8878 | 2.08 | 0.1493 |
| 10 | rs11594082 | 72969259 | 1 | 2 | 126 | 138 | 0.913 | 0.5455 | 0.4602 |
| 10 | rs10786284 | 98125495 | 0 | 1 | 0 | 0 | NA | NA | NA |
| 10 | rs515910 | 105956394 | 2 | 1 | 300 | 272 | 1.103 | 1.371 | 0.2417 |
| 11 | rs3893215 | 17721406 | 0 | 2 | 0 | 0 | NA | NA | NA |
| 11 | rs10830468 | 87604834 | 0 | 2 | 0 | 0 | NA | NA | NA |
| 12 | rs4964805 | 102716954 | 0 | 2 | 0 | 0 | NA | NA | NA |
| 13 | rs7995215 | 93206507 | 1 | 2 | 279 | 317 | 0.8801 | 2.423 | 0.1196 |
| 14 | rs2239627 | 22705999 | 0 | 2 | 0 | 0 | NA | NA | NA |
| 14 | rs10483286 | 24273582 | 0 | 2 | 0 | 0 | NA | NA | NA |
| 16 | rs10514604 | 83003885 | 0 | 2 | 0 | 0 | NA | NA | NA |
| 17 | rs2440129 | 6847295 | 0 | 2 | 0 | 0 | NA | NA | NA |

Segment-Based Comparative Analysis of CNVs

Figure 7:
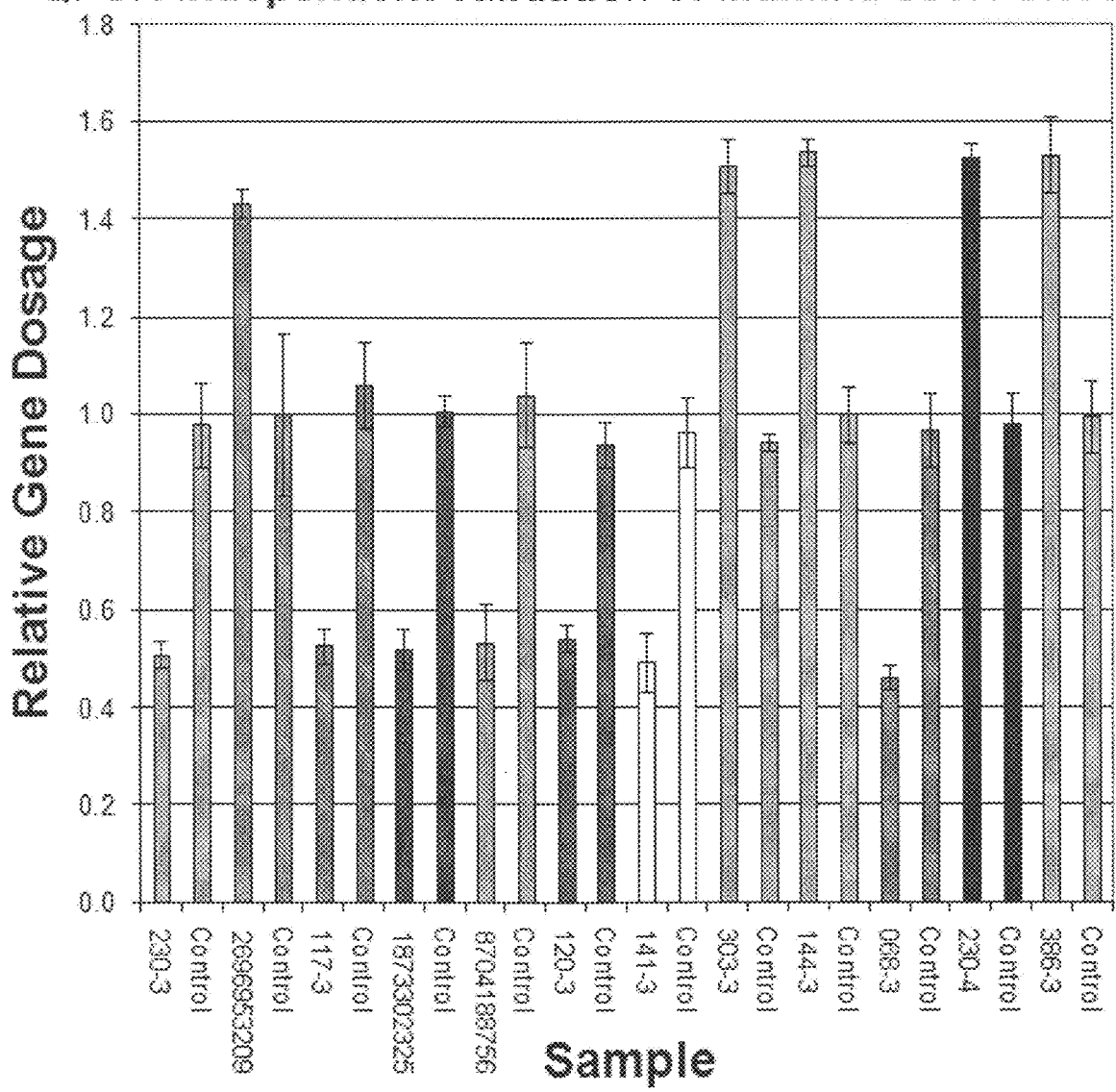
FIG. 7. CHOP Illumina Human Hap550 Independent Validation using qPCR. Fluorescent probe-based qPCR assays using Roche Universal probe were designed to validate every candidate CNV with a completely independent test (representative series shown for each locus in case and control pairs). Error bars denote the standard deviation of quadruplicate runs. Del, deletion; Dup, duplication.

To identify novel genomic loci harboring CNVs potentially contributing to ADHD, we applied a segment-based scoring approach that scans the genome for consecutive SNPs with more frequent copy number changes in cases compared to controls as we have previously described (Glessner, et al. 2009; Wang, et al. 2007). The genomic span for these consecutive SNPs delineates common copy number variation regions, or CNVRs. In the CHOP cohort, we identified 10 CNVRs that were observed in multiple cases but not in controls, as well as 2 CNVRs that had higher frequency in cases compared to controls. To ensure reliability of our CNV detection method, we experimentally validated all CNVRs using quantitative PCR (qPCR), a method commonly used for independent validation of CNVs (FIG. 7). Thus, we have applied a separate validation technique on all the CNVs reported to ensure positive confirmation. Using this approach, we have identified and experimentally validated a total of 12 CNV loci that were either observed in ADHD cases only or overrepresented in the ADHD cases that we subsequently took forward for replication in independent study cohorts.

Replication analysis was performed in five independent cohorts, including ADHD subjects from IMAGE, PUWMa, IMAGE II, NIMH, and Utah. Based on the 10 case-specific CNVs from the discovery cohort, 3 were also exclusive to replication cohort cases, notably GRM7, GRM8 and NEGR1, with resulting combined P-values of $3.52\times10^{-6}$ and $8.14\times10^{-5}$, for GRM8 and GRM7, respectively (Table 3A). A third GRM gene, GRM5, was observed in 10 ADHD cases (10/3,506) and one control (1/13,327) with resulting $P=1.36\times10^{-6}$ (Table 3A). GRM1 was observed in 8 cases and 2 controls $P=1.05\times10^{-4}$. While odds ratios (ORs) could not be estimated for GRM7 and GRM8, since these CNVs were absent in the control subject, the ORs of GRM5 and GRM1 amounted to 38.12 and 15.24, respectively (Table 3), suggesting that the contribution of these CNVs to the ADHD phenotype is potentially high. Thus, these 4 GRM genes were impacted by CNVs that associated with ADHD and replicated successfully in the independent ADHD cohorts (Table 3 and Table 11), whereas the other CNV loci were also observed to be enriched in the ADHD cases, albeit at nominally significant P values (Table 3b and Table 11).

(12) with Build 36 of the human genome. Experimental validation of IMAGE, PUWMa, IMAGE II, NIMH, and Utah CNVs, using qPCR, together with Raw BAF and LRR plots are shown in FIGS. 2-4.

Taken together, we have uncovered four genes directly impacted by CNVRs in multiple independent cohorts that belong to the metabotropic glutamate receptor gene family (InterPro category "GPCR, family 3, metabotropic glutamate receptor"; $P=2.1\times10^{-9}$). It is also noteworthy that both GRM2 and GRM6 were found to be impacted by deletions in single ADHD cases in the IMAGE II cohort and were absent in the control subjects. We additionally evaluated the significance of the GRM genes, using TDT in the same cohort, and the best support was observed for GRM7, $P=8.35\times10^{-5}$ (Table 12). Furthermore, analysis was also performed to address family based CNV statistics based on transmission disequilibrium and de novo events in the

TABLE 11

Discovery, Replication, and Combined Significance of CNV Regions.

| CNVR | Discovery P-value | Replication P-value | Combined P-value | Permuted Discovery P-value | Permuted Replication P-value | Permuted Combined P-value | Type | Gene |
|---|---|---|---|---|---|---|---|---|
| chr11: 88269449-88351661 | $1.53\times10^{-3}$ | $5.29\times10^{-4}$ | $1.36\times10^{-6}$ | 0.025 | 0.001 | 0.002 | Del | GRM5 |
| chr7: 126441593-126621501 | $7.74\times10^{-3}$ | $4.35\times10^{-4}$ | $3.52\times10^{-6}$ | 0.013 | <0.001 | <0.001 | Del | GRM8 |
| chr3: 7183953-7197236 | $1.53\times10^{-3}$ | $4.53\times10^{-2}$ | $8.14\times10^{-5}$ | 0.011 | 0.039 | <0.001 | Del | GRM7 |
| chr6: 146657076-146694047 | $4.42\times10^{-3}$ | $9.63\times10^{-3}$ | $1.05\times10^{-4}$ | 0.006 | <0.001 | <0.001 | Dup | GRM1 |
| chr1: 72317292-72328395 | $1.53\times10^{-3}$ | $2.13\times10^{-1}$ | $3.91\times10^{-4}$ | 0.036 | 0.213 | 0.011 | Dup | NEGR1 |
| chr7: 153495598-153564827 | $1.53\times10^{-3}$ | $6.82\times10^{-2}$ | $4.08\times10^{-4}$ | <0.001 | 0.058 | <0.001 | Dup | DPP6 |
| chr5: 65027976-65046520 | $1.53\times10^{-3}$ | $1.17\times10^{-1}$ | $4.68\times10^{-4}$ | 0.003 | 0.108 | 0.001 | Del | SGTB/NLN |
| chr1: 56053497-56064495 | $3.91\times10^{-2}$ | $2.12\times10^{-2}$ | $1.54\times10^{-3}$ | 0.035 | 0.024 | <0.001 | Del | USP24 |
| chr19: 38427720-38444834 | $4.42\times10^{-3}$ | $2.89\times10^{-1}$ | $4.95\times10^{-3}$ | 0.002 | 0.262 | 0.007 | Del | SLC7A10 |
| chr3: 1844168-1859889 | $1.53\times10^{-3}$ | $4.12\times10^{-1}$ | $8.81\times10^{-3}$ | 0.008 | 0.416 | 0.015 | Del | CNTN4 |
| chr2: 81419297-81446082 | $3.91\times10^{-2}$ | $2.89\times10^{-1}$ | $3.83\times10^{-2}$ | 0.046 | 0.294 | 0.032 | Dup | CTNNA2 |
| chr4: 113772340-113788584 | $3.91\times10^{-2}$ | $2.89\times10^{-1}$ | $3.83\times10^{-2}$ | 0.033 | 0.288 | 0.042 | Dup | LARP7 |

The top 4 most significant loci are shown in bold.

Figure 9:
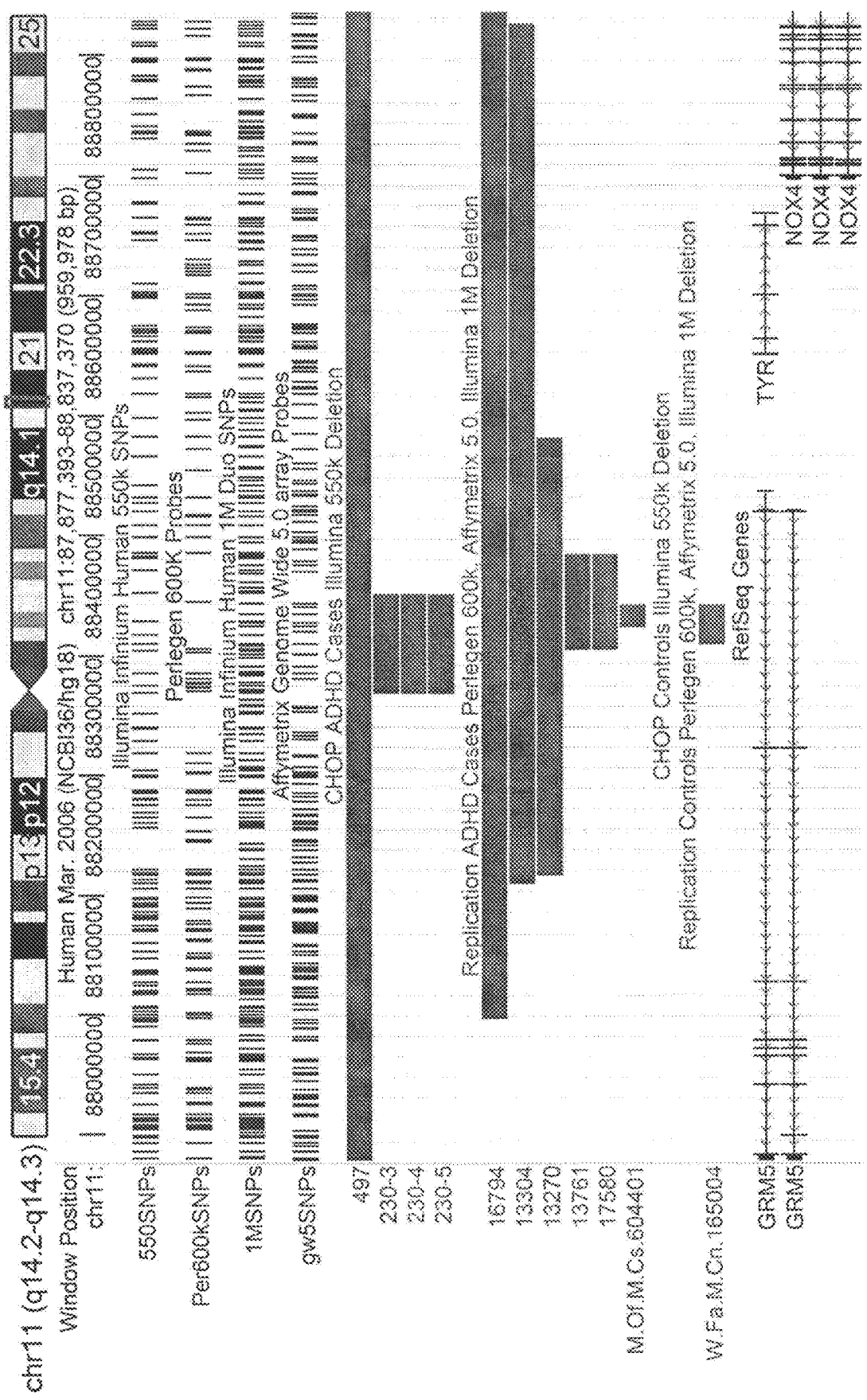
FIG. 9. An illustration of the deletion directly impacting GRM5, exclusive to ADHD cases and replicated in IMAGE and PUWMa. Four CHOP ADHD case hemizygous deletions in GRM5 replicated by 2 deletions and 3 larger deletions found in IMAGE and 1 PUWMa deletion. SNP coverage of the Illumina 550k, Perlegen 600k, Illumina 1M, and Affymetrix 5.0 arrays are shown as vertical lines.

FIG. 9 shows the CNV deletions observed at the GRM5 locus (10 cases vs 1 control), using UCSC Genome Browser family-based subset of 311 CHOP families and 422 IMAGE families (Tables 12 and 14).

TABLE 12

ADHD Genotype GWAS of Glutamatergic Genes. The most significant SNP genotype association in each of the eight GRM gene regions. A) ADHD TDT CHOP Illumina 550k B) ADHD Case: Control CHOP Illumina 550k C) ADHD IMAGE Perlegen 600k.

A)

| CHR | SNP | BP | A1 | A2 | T | U | OR | CHISQ | P | Gene |
|---|---|---|---|---|---|---|---|---|---|---|
| 11 | rs4237549 | 88407924 | 2 | 1 | 31 | 61 | 0.5082 | 9.783 | 0.001762 | GRM5 |
| 7 | rs17864159 | 126444172 | 1 | 2 | 22 | 46 | 0.4783 | 8.471 | 0.003609 | GRM8 |
| 6 | rs3887555 | 34177040 | 1 | 2 | 208 | 161 | 1.292 | 5.986 | 0.01442 | GRM4 |
| 7 | rs6943762 | 86047914 | 2 | 1 | 69 | 99 | 0.697 | 5.357 | 0.02064 | GRM3 |
| 3 | rs7623055 | 7485891 | 1 | 2 | 151 | 193 | 0.7824 | 5.128 | 0.02354 | GRM7 |
| 6 | rs362839 | 146721428 | 2 | 1 | 125 | 161 | 0.7764 | 4.531 | 0.03328 | GRM1 |
| 3 | rs4687770 | 51730105 | 2 | 1 | 114 | 94 | 1.213 | 1.923 | 0.1655 | GRM2 |
| 5 | rs2078183 | 178357150 | 2 | 1 | 190 | 210 | 0.9048 | 1 | 0.3173 | GRM6 |

B)

| CHR | SNP | BP | A1 | F_A | F_U | A2 | OR | CHISQ | P | Gene |
|---|---|---|---|---|---|---|---|---|---|---|
| 3 | rs7623055 | 7485891 | 1 | 0.3582 | 0.4129 | 2 | 0.7936 | 15.48 | 8.35E-05 | GRM7 |
| 11 | rs1354411 | 88016449 | 2 | 0.03643 | 0.0566 | 1 | 0.6302 | 10.21 | 0.001396 | GRM5 |
| 7 | rs2283100 | 126643293 | 2 | 0.2281 | 0.193 | 1 | 1.235 | 9.527 | 0.002024 | GRM8 |
| 6 | rs1873250 | 34130718 | 2 | 0.2134 | 0.2455 | 1 | 0.8338 | 7.062 | 0.007873 | GRM4 |
| 7 | rs10952890 | 86193151 | 1 | 0.02753 | 0.03917 | 2 | 0.6945 | 4.782 | 0.02877 | GRM3 |
| 5 | rs2078183 | 178357150 | 2 | 0.4593 | 0.4897 | 1 | 0.8852 | 4.605 | 0.03189 | GRM6 |

TABLE 12-continued

ADHD Genotype GWAS of Glutamatergic Genes. The most significant SNP genotype association in each of the eight GRM gene regions. A) ADHD TDT CHOP Illumina 550k B) ADHD Case: Control CHOP Illumina 550k C) ADHD IMAGE Perlegen 600k.

| | | | | | | | | | | |
|---|---|---|---|---|---|---|---|---|---|---|
| 6 | rs1983635 | 146707365 | 2 | 0.316 | 0.2917 | 1 | 1.122 | 3.515 | 0.06081 | GRM1 |
| 3 | rs4687592 | 51630896 | 1 | 0.03442 | 0.04041 | 2 | 0.8464 | 1.191 | 0.2752 | GRM2 |

C)

| CHR | SNP | BP | A1 | A2 | T | U | OR | CHISQ | P | Gene |
|---|---|---|---|---|---|---|---|---|---|---|
| 6 | rs12206652 | 34173960 | 2 | 1 | 265 | 216 | 1.227 | 4.992 | 0.02547 | GRM4 |
| 11 | rs160195 | 87932621 | 2 | 1 | 302 | 253 | 1.194 | 4.326 | 0.03753 | GRM5 |
| 7 | rs11563486 | 126621501 | 1 | 2 | 130 | 162 | 0.8025 | 3.507 | 0.06112 | GRM8 |
| 3 | rs11717471 | 7599469 | 2 | 1 | 238 | 280 | 0.85 | 3.405 | 0.06498 | GRM7 |
| 6 | rs2300620 | 146745874 | 2 | 1 | 160 | 133 | 1.203 | 2.488 | 0.1147 | GRM1 |
| 7 | rs1468413 | 86271589 | 1 | 2 | 190 | 162 | 1.173 | 2.227 | 0.1356 | GRM3 |
| 5 | rs7725272 | 178338994 | 2 | 1 | 289 | 261 | 1.107 | 1.425 | 0.2325 | GRM6 |
| 3 | rs6445959 | 51747387 | 2 | 1 | 169 | 153 | 1.105 | 0.795 | 0.3726 | GRM2 |

Figure 10:
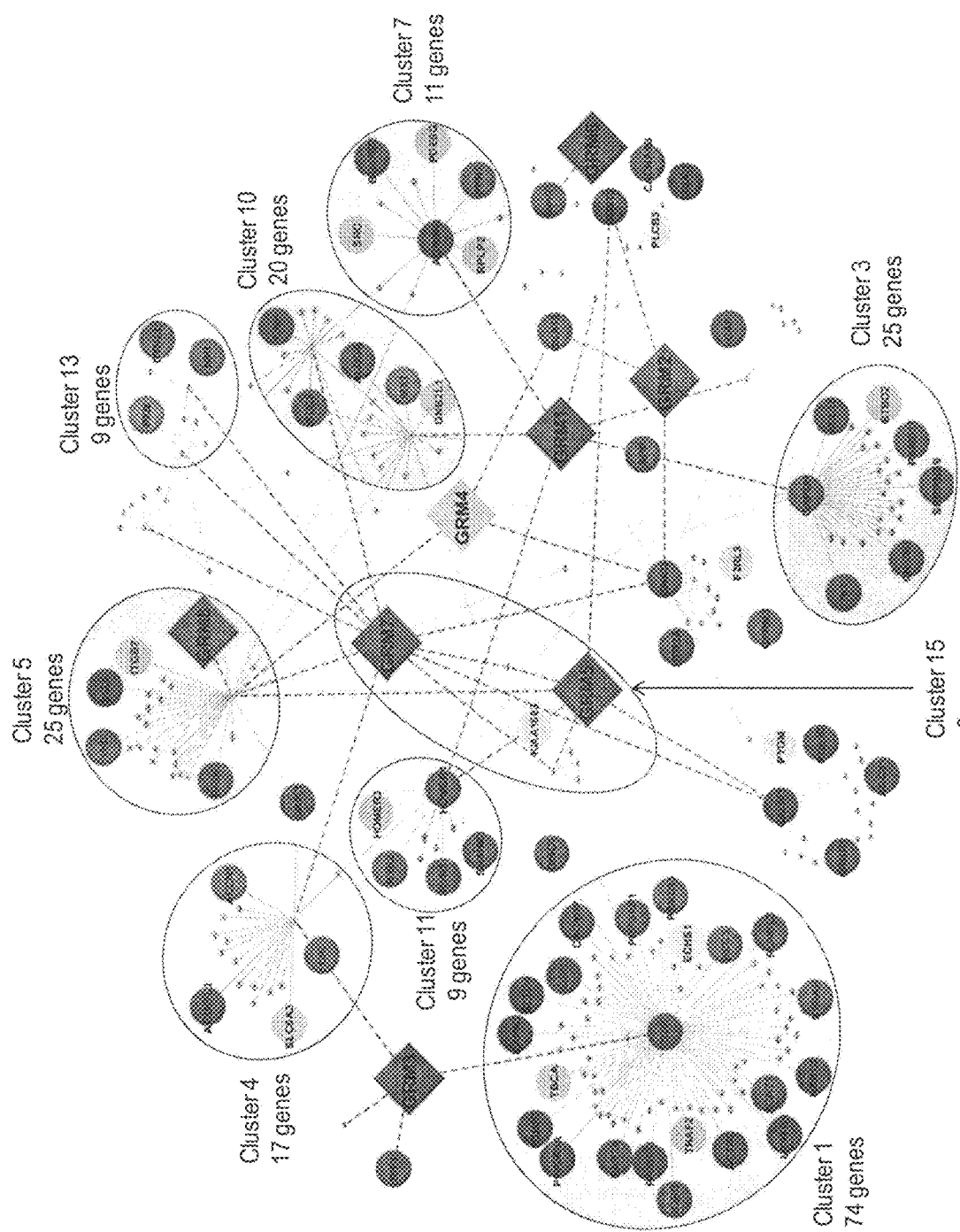
FIG. 10. A display of GRM receptor gene interaction networks impacted in ADHD. GRM receptor genes are shown as large diamond-shaped nodes while other interacting genes within 2 degrees if interaction are shown as smaller circular nodes. Nodes are shaded to represent enrichment of CNVs: dark shading are deletions enriched in cases, light shading are deletions enriched in controls, dark shading are duplications enriched in cases, light shading are duplications enriched in controls, and grey are diploid and devoid of CNVs. Thick dashed lines highlight edges connected to at least one GRM gene while grey thin dotted lines represent all other gene interactions. Highly connected modules enriched for significant functional annotations are highlighted by shaded ellipses.

In view of the above finding, we hypothesized that genes interacting with GRM receptor genes would collectively have more cases enriched with CNVs in comparison with healthy controls. We identified 228 genes within 2 degrees of relation to GRM genes based on the merged human interactome provided by the Cytoscape Software (Shannon, et al. 2003). We evaluated these genes in 1,231 ADHD case samples and 4,105 control samples, all of which were genotyped on the same platform at CHOP, for evidence of enrichment in the ADHD case samples (P<0.05). We detected 67 GRM receptor interacting genes that were enriched for CNVs in cases, in comparison with 16 genes in the controls, confirming over 3-fold enrichment in CNVs in this gene network in the ADHD cases (P=$4.38 \times 10^{-10}$, FIG. 10).

Figure 11:
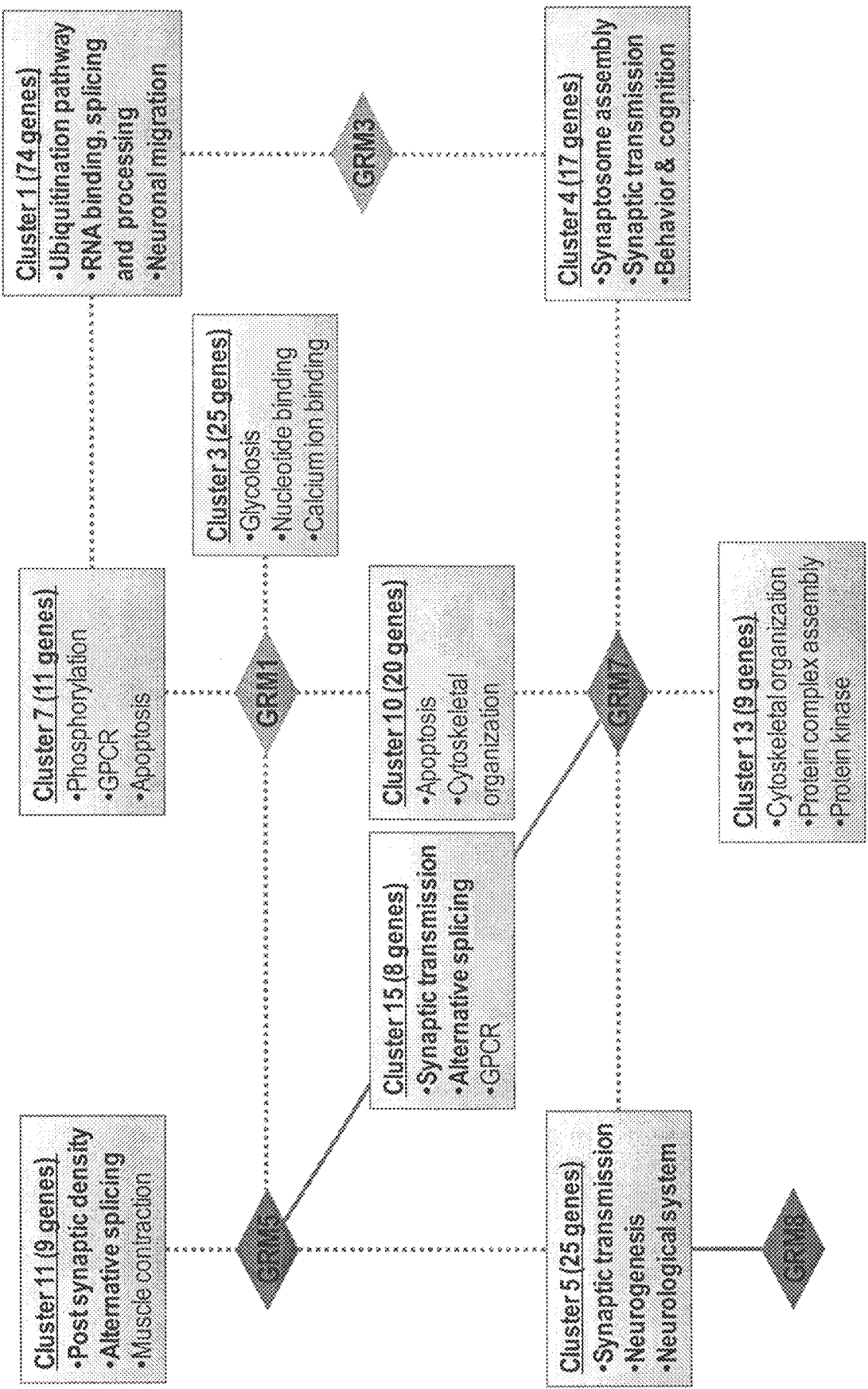
FIG. 11. A schematic overview showing the interaction of GRM receptors impacted in ADHD with modules of genes enriched for functional significance. GRM receptor genes are shown as diamonds with different shading to represent duplications and deletions respectively enriched in cases. Boxes highlight functional modules defined by the network of interacting genes that are significantly enriched for GO annotations. Functional modules describe significant functional annotations and are labeled with the cluster name and the number of component genes in parenthesis. Functional annotations that may be particularly pertinent to ADHD underlying pathophysiology are bolded. Edges of the network connect GRM receptor genes to functional modules: solid lines indicate membership of the GRM interacting gene in the functional module, and dotted lines indicate a first-degree relationship between GRM receptor genes and at least one component gene of a functional module.
Figure 12:
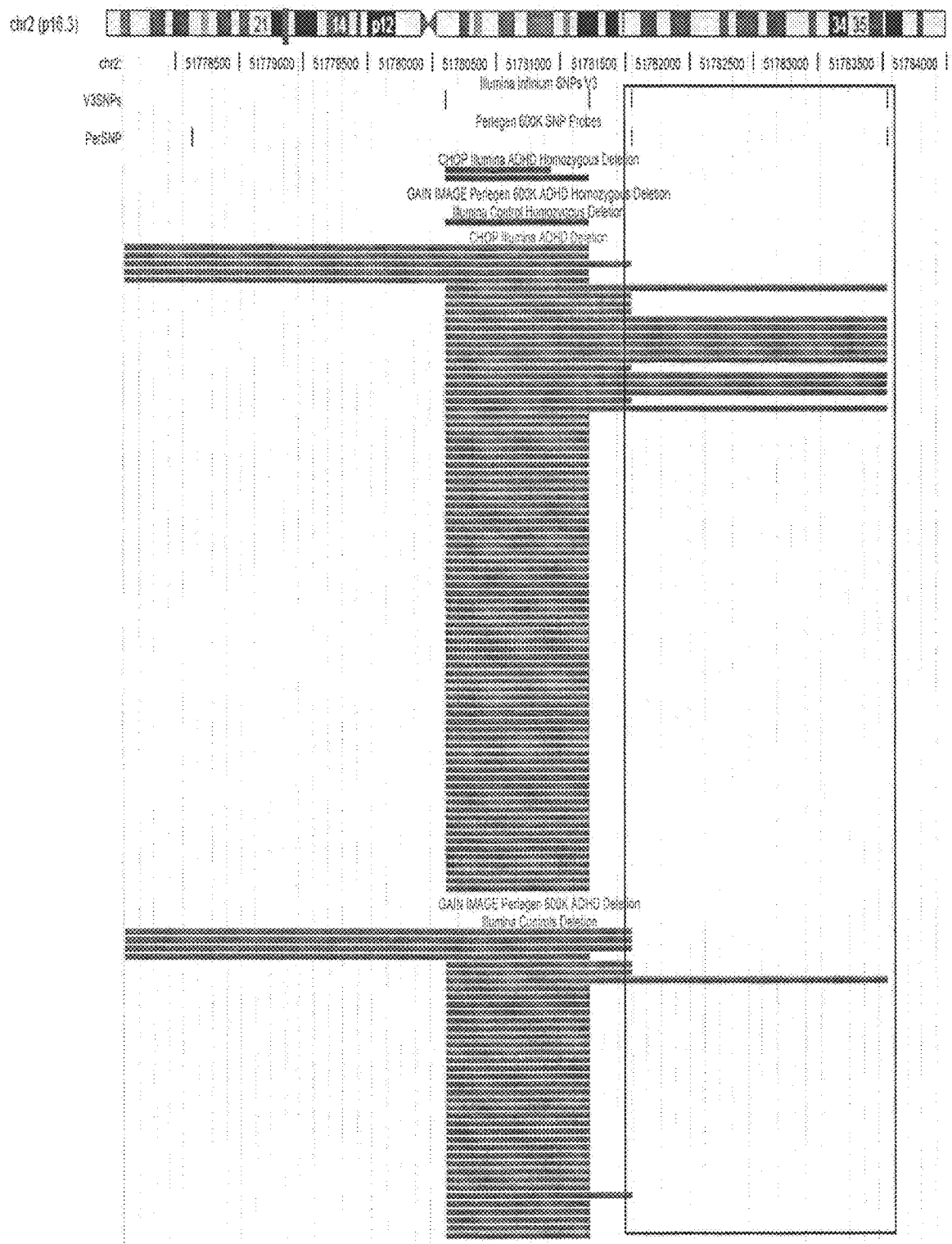
FIG. 12. A CNV peninsula false positive association example. An example from chr 2 is shown (location 51,777,616-51,784,033). All significant CNVRs are reviewed for CNV peninsulas indicating uncertainty in boundary truncation.

We subsequently clustered the above second degree GRM receptor gene interaction network to define highly interconnected modules of genes based on network topography, and looked for enrichment of gene ontology (GO) annotations within these modules. As shown in FIG. 11, GRMs do not form a large number of interactions, but importantly serve to coordinate functional modules of other sets of genes. For instance, GRM1 harbors duplications significantly enriched in ADHD cases and serves to coordinate functional modules involved in housekeeping functions such as carbohydrate metabolism, phosphorylation, apoptosis and ion binding. GRM5 and GRM7 both harbor deletions significantly enriched in cases and cluster within a functional module involved in synaptic transmission and alternative splicing. Specifically, GRM5 serves to coordinate alternative spicing with synaptic transmission and other neuronal processes at the post-synaptic density, while GRM7 coordinates functional modules integrating neurological processes and synaptic activity with housekeeping functions such as cytoskeletal organization and apoptosis. GRM8 also harbors deletions significantly enriched in cases and is itself contained within a functional module that is involved in synaptic transmission and neurogenesis. Although not significantly enriched in cases, GRM3 has duplications that are more frequently observed in cases and serves to coordinate ubiquitination pathways, RNA binding, splicing, and processing, and neuronal migration, with neurological processes including synaptic transmission with effects of behavior and cognition.

Example II

Multiplex SNP Panel for Diagnosis of ADHD

As described above in Example I, several genetic alterations have been found to be associated with the ADHD phenotype. The information herein above can be applied clinically to patients for diagnosing an increased susceptibility for developing ADHD, and therapeutic intervention. A preferred embodiment of the invention comprises clinical application of the information described herein to a patient. Diagnostic compositions, including microarrays, and methods can be designed to identify the genetic alterations described herein in nucleic acids from a patient to assess susceptibility for developing ADHD. This can occur after a patient arrives in the clinic; the patient has blood drawn, and using the diagnostic methods described herein, a clinician can detect a SNP in the genetic regions listed in Tables 13A and 13B below. The typical age range for a patient to be screened is between 1 and 12 years of age. The information obtained from the patient sample (e.g., nucleic acids), which can optionally be amplified prior to assessment, will be used to diagnose a patient with an increased or decreased susceptibility for developing ADHD. Kits for performing the diagnostic method of the invention are also provided herein. Such kits comprise a microarray comprising at least one of the SNPs provided herein in and the necessary reagents for assessing the patient samples as described above. In an alternative embodiment, a multiplex SNP panel is employed and the patient sample is assessed for the presence or absence of all the SNPs listed in the Tables below.

Table 13A provides all the genes, physical genome ranges, and SNP ranges of the ADHD markers disclosed. Table 13B provides a "SNPList" which is a minimal set for a "diagnostic array" such as veracode which is technlology approved by FDA. Optimally, the flanking SNPs to these CNVs are included as well as intervening SNPs as they could all be used to capture the CNV.

When we perform the testing, the clustering algorithm GenCall will be run on the sample set and SNPs poorly clustered or significantly deviating from Hardy Weinberg equilibrium will be reviewed. Copy number variations (CNVs) will be detected using our PennCNV hidden Markov model (HMM) copy number variation algorithm. Median normalization which is default is turned off since the data of targeted regions instead of distributed genome-wide does not provide enough information for median normalization. For optimization, the HMM can be trained with good quality data suited to the specific array observed values (call rate >98% and standard deviation of log r ratio <0.3). PennCNV will detect regions of contiguous SNPs with intensity (log R Ratio) trending below 0 indicating deletion or trending above 0 indicating duplication. If no such trend is observed, no CNV call will be made indicating a normal diploid state. In tandem, the genotype data is evaluated in a continuous physical position for homozygous genotypes indicating deletion or AAB and ABB genotypes indicating duplication weighted with positive correlation for control minor allele frequency.

The identity of ADHD-involved genes and the patient results will indicate which variants are present, and will identify those that possess an altered risk for developing ADHD. The information provided herein allows for therapeutic intervention at earlier times in disease progression that previously possible. Also as described herein above, the GRM receptor family provides novel targets for the development of new therapeutic agents efficacious for the treatment of ADHD. In particular, it would be desirable to modulate expression of such genes in those patients that are more prone to develop the disease.

TABLE 13A

Multiplex SNP Panel.

| Gene | Range (B36/hg18) | StartSNP | EndSNP | Del Counts (cases:controls) | Dup Counts (cases:controls) |
|---|---|---|---|---|---|
| GRM5 | chr11: 88269449-88351661 | rs604179 | rs669724 | 10:1 | 0:0 |
| GRM8 | chr7: 126525124-126536202 | rs7794734 | rs2237790 | 8:0 | 0:0 |
| GRM7 | chr3: 7183953-7197236 | rs1516302 | rs6784317 | 6:0 | 0:0 |
| GRM1 | chr6: 146657076-146694047 | rs12200797 | rs362949 | 0:0 | 8:2 |
| NEGR1 | chr1: 72317292-72328395 | rs12033161 | rs2821257 | 0:0 | 5:0 |
| DPP6 | chr7: 153495598-153564827 | rs4389846 | rs12703329 | 0:0 | 8:2 |
| SGTB/NLN | chr5: 65027976-65046520 | rs10073281 | rs972501 | 6:1 | 0:0 |
| USP24 | chr1: 56053497-56064495 | rs7527177 | rs4333889 | 6:2 | 0:0 |
| SLC7A10 | chr19: 38427720-38444834 | rs748680 | rs4530278 | 7:5 | 0:0 |
| CNTN4 | chr3: 1844168-1859889 | rs10510218 | rs7625240 | 7:6 | 0:0 |
| CTNNA2 | chr2: 81419297-81446082 | rs4430978 | rs1595071 | 4:3 | 0:0 |
| LARP7 | chr4: 113772340-113788584 | rs12054518 | rs7690429 | 4:3 | 0:0 |
| ACAT1 | chr11: 107497467-107523485 | rs3741049 | rs11212525 | 0:0 | 1:0 |
| ACCN1 | chr17: 28364218-29507938 | rs28933 | rs11080254 | 0:0 | 3:1 |
| ACTR2 | chr2: 65308405-65351891 | rs268859 | rs4671124 | 1:0 | 0:1 |
| ADCY1 | chr7: 45580645-45729237 | rs4724420 | rs3735666 | 0:0 | 1:1 |
| ADRBK1 | chr11: 66790668-66810933 | rs12274774 | rs12274774 | 1:0 | 0:0 |
| ALDOA | chr16: 29971972-29989236 | rs9928448 | rs2071390 | 3:8 | 2:6 |
| APP | chr21: 26174731-26465003 | rs3787620 | rs462281 | 0:0 | 8:2 |
| ARL15 | chr5: 53216370-53642160 | rs271246 | rs35947 | 1:1 | 2:0 |
| ATXN7L3 | chr17: 39624698-39631055 | rs11652516 | rs11652516 | 1:1 | 0:0 |
| BDKRB2 | chr14: 95740949-95780538 | rs1959053 | rs2069591 | 1:1 | 0:0 |
| CA8 | chr8: 61263976-61356508 | rs7460476 | rs6998745 | 0:0 | 1:0 |
| CACNA1B | chr9: 139892061-140136452 | rs10867084 | rs2606358 | 0:0 | 2:2 |
| CACYBP | chr1: 173235193-173247786 | rs6425310 | rs11590474 | 1:0 | 0:0 |
| CALM1 | chr14: 89933125-89944363 | rs2300497 | rs1058903 | 1:2 | 0:0 |
| CHRM3 | chr1: 237616487-238116519 | rs4130463 | rs536477 | 0:0 | 2:1 |
| CIC | chr19: 47480656-47491789 | rs3826706 | rs3826706 | 1:1 | 0:0 |
| CNP | chr17: 37372284-37383280 | rs8078650 | rs11079028 | 1:2 | 0:0 |
| CRHR1 | chr17: 41217448-41268973 | rs4792886 | rs17763104 | 1:0 | 0:0 |
| DISC1 | chr1: 229829183-230243641 | rs2082552 | rs980989 | 0:0 | 4:7 |
| DYNLL1 | chr12: 119392042-119420681 | rs606443 | rs580016 | 0:0 | 1:0 |
| FPR1 | chr19: 56940837-56946962 | rs867228 | rs4801891 | 0:0 | 1:1 |
| GAPDH | chr12: 6513917-6517797 | rs1060619 | rs1060619 | 0:2 | 1:1 |
| GNA15 | chr19: 3087229-3114741 | rs1465245 | rs1637656 | 1:1 | 1:0 |
| GNAI2 | chr3: 50238727-50271790 | rs11716295 | rs2236944 | 2:4 | 0:0 |
| GNAO1 | chr16: 54783648-54948650 | rs16956168 | rs3790116 | 0:0 | 1:1 |
| GNAQ | chr9: 79525010-79836012 | rs6560613 | rs1930543 | 1:0 | 0:0 |
| GRIK1 | chr21: 29831124-30234153 | rs2832390 | rs2255821 | 0:0 | 8:2 |
| GRIK3 | chr1: 37039200-37272431 | rs528137 | rs563293 | 1:0 | 0:0 |
| GRM1 | chr6: 146390610-146800427 | rs12196298 | rs2942 | 0:0 | 7:2 |
| GRM3 | chr7: 86111165-86332128 | rs701332 | rs6967992 | 0:0 | 1:0 |
| GRM5 | chr11: 87880625-88420888 | rs308884 | rs7931721 | 4:0 | 3:2 |
| GRM7 | chr3: 6877926-7758217 | rs6443074 | rs17047886 | 4:0 | 0:0 |
| GRM8 | chr7: 125865892-126670546 | rs13240504 | rs13246388 | 3:0 | 1:1 |
| GSN | chr9: 123003581-123134941 | rs1590345 | rs306772 | 1:0 | 1:0 |
| HOMER1 | chr5: 78705541-78845456 | rs3822568 | rs11948804 | 0:0 | 1:0 |
| HTR2A | chr13: 46305513-46368995 | rs3803189 | rs6312 | 0:0 | 1:0 |
| MAPK1 | chr22: 20443946-20551970 | rs2298432 | rs2876981 | 1:0 | 0:0 |
| MTHFD1 | chr14: 63924845-63996474 | rs8011839 | rs2281603 | 1:1 | 0:0 |
| MX1 | chr21: 41714311-41753008 | rs457920 | rs468811 | 0:0 | 7:2 |
| NARG1 | chr4: 140442125-140531385 | rs13147688 | rs2060685 | 1:0 | 0:0 |
| NMI | chr2: 151835230-151854620 | rs446791 | rs2113509 | 0:0 | 1:0 |
| PCBP3 | chr21: 46092504-46186795 | rs11701789 | rs8133858 | 3:2 | 6:3 |
| PDE1C | chr7: 31759156-32305466 | rs917749 | rs215605 | 1:0 | 1:1 |
| PPP2R1A | chr19: 57385045-57421483 | rs13344984 | rs7259175 | 0:0 | 1:0 |
| PRPSAP1 | chr17: 71818609-71861526 | rs407281 | rs8075628 | 1:0 | 1:1 |
| PSMD11 | chr17: 27795614-27832155 | rs9889352 | rs12162135 | 2:24 | 1:0 |
| PSMD13 | chr11: 226976-242981 | rs1045288 | rs6598055 | 0:4 | 1:2 |

TABLE 13A-continued

Multiplex SNP Panel.

| Gene | Range (B36/hg18) | StartSNP | EndSNP | Del Counts (cases:controls) | Dup Counts (cases:controls) |
|---|---|---|---|---|---|
| PXN | chr12: 119132639-119187892 | rs10128770 | rs1151836 | 0:0 | 1:0 |
| QRICH2 | chr17: 71781724-71815356 | rs347675 | rs346789 | 1:1 | 0:1 |
| RANBP1 | chr22: 18485023-18494706 | rs2238798 | rs2238798 | 2:3 | 0:9 |
| RAP2A | chr13: 96884476-96918245 | rs2389908 | rs2389908 | 0:0 | 1:1 |
| RCC1 | chr1: 28717331-28738194 | rs10915206 | rs10915206 | 0:0 | 1:0 |
| RGS12 | chr4: 3285671-3411438 | rs12643903 | rs16844364 | 2:0 | 0:0 |
| RIF1 | chr2: 151974645-152040665 | rs2444256 | rs16830067 | 0:0 | 1:0 |
| RUVBL2 | chr19: 54188967-54210994 | rs12610125 | rs7256033 | 1:0 | 0:3 |
| RYR1 | chr19: 43616179-43770044 | rs919781 | rs10408694 | 1:2 | 1:1 |
| RYR2 | chr1: 235272324-236063911 | rs1881548 | rs6429040 | 1:0 | 1:0 |
| SDC3 | chr1: 31118568-31154067 | rs2282440 | rs10158813 | 1:0 | 0:1 |
| SELE | chr1: 167958405-167969803 | rs5368 | rs5353 | 1:0 | 0:0 |
| SERPINB9 | chr6: 2832502-2848506 | rs318477 | rs9503330 | 0:0 | 1:0 |
| SETD4 | chr21: 36328708-36358576 | rs2835239 | rs2835263 | 2:0 | 8:3 |
| SHANK1 | chr19: 55856895-55912007 | rs4802724 | rs3745530 | 0:0 | 1:0 |
| SORD | chr15: 43102643-43154331 | rs11636774 | rs2854439 | 0:0 | 1:0 |
| STRAP | chr12: 15926612-15947677 | rs16911383 | rs10846246 | 0:0 | 1:1 |
| TK1 | chr17: 73681775-73694726 | rs1065769 | rs11653181 | 2:0 | 0:2 |
| TNIK | chr3: 172264363-172660546 | rs12486818 | rs10936688 | 1:0 | 0:0 |
| VHL | chr3: 10158318-10168746 | rs1642742 | rs1642742 | 0:0 | 1:0 |

TABLE 13B

A SNPList available for implementation in a diagnostic array.

| Gene | SNP | Gene | SNP | Gene | SNP |
|---|---|---|---|---|---|
| GRM5 | rs506811 | CNP | rs11079028 | HOMER1 | rs12187625 |
| GRM5 | rs604179 | GNAQ | rs11145589 | SHANK1 | rs12460584 |
| GRM5 | rs1954979 | BDKRB2 | rs11160322 | CA8 | rs12550354 |
| GRM5 | rs693008 | CACYBP | rs11590474 | PDE1C | rs12701140 |
| GRM5 | rs594561 | GRIK3 | rs1160752 | CA8 | rs12708003 |
| GRM5 | rs585423 | ATXN7L3 | rs11652516 | PCBP3 | rs13050871 |
| GRM5 | rs2047507 | TK1 | rs11653181 | ARL15 | rs13164221 |
| GRM5 | rs598758 | PCBP3 | rs11701789 | SERPINB9 | rs13196459 |
| GRM5 | rs547644 | GNAI2 | rs11716295 | PDE1C | rs13238408 |
| GRM5 | rs316090 | RYR2 | rs11810113 | PPP2R1A | rs13344984 |
| GRM5 | rs656544 | SDC3 | rs11810325 | NMI | rs13383563 |
| GRM5 | rs641052 | SDC3 | rs12085929 | RYR2 | rs1361115 |
| GRM5 | rs11021670 | MAPK1 | rs12172554 | CACNA1B | rs1378954 |
| GRM5 | cnvi0116228 | ADRBK1 | rs12274774 | RYR2 | rs1409052 |
| GRM5 | rs541046 | PCBP3 | rs12482750 | ADCY1 | rs1521470 |
| GRM5 | rs475872 | RUVBL2 | rs12610125 | PPP2R1A | rs1560092 |
| GRM5 | rs694665 | TNIK | rs12637875 | STRAP | rs1564183 |
| GRM5 | rs573912 | RGS12 | rs12641989 | GNA15 | rs1637656 |
| GRM5 | rs563371 | PDE1C | rs12701140 | VHL | rs1642742 |
| GRM5 | rs533163 | RGS12 | rs13116176 | RIF1 | rs16823297 |
| GRM5 | rs5027960 | RGS12 | rs1320763 | RIF1 | rs16830067 |
| GRM5 | rs644170 | PDE1C | rs13238408 | ARL15 | rs16882366 |
| GRM5 | rs675010 | RYR2 | rs1361115 | ARL15 | rs16882383 |
| GRM5 | cnvi0050221 | RGS12 | rs1406674 | STRAP | rs16911383 |
| GRM5 | rs518167 | RYR2 | rs1409052 | ARL15 | rs169382 |
| GRM5 | rs591849 | GNAQ | rs1436450 | APP | rs17001492 |
| GRM5 | rs655683 | GNA15 | rs1637656 | GNAO1 | rs17281761 |
| GRM5 | rs597462 | RGS12 | rs16844364 | HTR2A | rs17288723 |
| GRM5 | rs539752 | GSN | rs16910509 | ARL15 | rs17413044 |
| GRM5 | rs477399 | ARL15 | rs17267677 | DISC1 | rs17804007 |
| GRM5 | rs597303 | CRHR1 | rs173365 | DISC1 | rs17804163 |
| GRM5 | rs669724 | CRHR1 | rs17763104 | APP | rs1783016 |
| GRM5 | rs677526 | GNAQ | rs17786782 | PPP2R1A | rs17835915 |
| GRM8 | rs10954144 | PDE1C | rs1860790 | APP | rs17887438 |
| GRM8 | rs7794734 | MAPK1 | rs1892846 | ACCN1 | rs1844737 |
| GRM8 | rs12375090 | NARG1 | rs2060685 | PDE1C | rs1860790 |
| GRM8 | rs6975798 | CNP | rs2070106 | ACCN1 | rs1985858 |
| GRM8 | rs1557644 | ALDOA | rs2071390 | SETD4 | rs2018721 |
| GRM8 | rs12706778 | RANBP1 | rs2238798 | FPR1 | rs2070746 |
| GRM8 | rs2237790 | SETD4 | rs2255734 | RYR1 | rs2071085 |
| GRM8 | rs11563719 | RGS12 | rs2269497 | DISC1 | rs2082552 |
| GRM7 | rs9864350 | QRICH2 | rs2279053 | ACCN1 | rs2087633 |
| GRM7 | rs1516302 | QRICH2 | rs2279054 | NMI | rs2113509 |
| GRM7 | rs1400163 | TNIK | rs2292005 | RIF1 | rs2123465 |
| GRM7 | rs965170 | CALM1 | rs2300497 | ACCN1 | rs2130818 |

TABLE 13B-continued

A SNPList available for implementation in a diagnostic array.

| Gene | SNP | Gene | SNP | Gene | SNP |
|---|---|---|---|---|---|
| GRM7 | rs11131064 | CALM1 | rs2300502 | APP | rs214488 |
| GRM7 | rs10866078 | PDE1C | rs2302450 | PXN | rs2239206 |
| GRM7 | rs1400166 | RYR1 | rs2304150 | GRIK1 | rs2251388 |
| GRM7 | rs17235039 | CRHR1 | rs242939 | SETD4 | rs2255734 |
| GRM7 | rs10510351 | CRHR1 | rs242942 | GRIK1 | rs2268203 |
| GRM7 | rs11715681 | RYR2 | rs2485570 | PSMD13 | rs2272566 |
| GRM7 | rs6784317 | RYR2 | rs2490365 | RYR1 | rs2288888 |
| GRM7 | rs1963265 | RYR2 | rs2490371 | PDE1C | rs2302450 |
| GRM1 | rs6570746 | RYR2 | rs2490372 | RAP2A | rs2389908 |
| GRM1 | rs12200797 | RYR2 | rs2490373 | RIF1 | rs2432957 |
| GRM1 | rs1555084 | RYR2 | rs2490385 | RIF1 | rs2444256 |
| GRM1 | rs1009085 | RYR2 | rs2490389 | RIF1 | rs2444258 |
| GRM1 | rs362962 | TK1 | rs2661679 | RIF1 | rs2444263 |
| GRM1 | rs362949 | ACTR2 | rs268859 | RIF1 | rs2444273 |
| GRM1 | rs362835 | SETD4 | rs2835239 | RYR2 | rs2485570 |
| NEGR1 | rs2821267 | SETD4 | rs2835240 | RYR2 | rs2490365 |
| NEGR1 | rs12033161 | SETD4 | rs2835244 | RYR2 | rs2490371 |
| NEGR1 | rs988421 | PCBP3 | rs2839060 | RYR2 | rs2490372 |
| NEGR1 | rs2821255 | TK1 | rs2854701 | RYR2 | rs2490373 |
| NEGR1 | rs2821257 | TK1 | rs2854702 | RYR2 | rs2490385 |
| NEGR1 | rs10493493 | MAPK1 | rs2876981 | RYR2 | rs2490389 |
| DPP6 | rs3115157 | GSN | rs306759 | ARL15 | rs25860 |
| DPP6 | rs4389846 | GSN | rs306761 | GNAO1 | rs2587888 |
| DPP6 | rs4131646 | GSN | rs306784 | ARL15 | rs26775 |
| DPP6 | rs7790046 | RGS12 | rs3088231 | HTR2A | rs2770304 |
| DPP6 | rs7794112 | CALM1 | rs3213718 | ARL15 | rs277340 |
| DPP6 | rs12532924 | QRICH2 | rs346789 | ARL15 | rs28033 |
| DPP6 | rs4452722 | PRPSAP1 | rs346794 | APP | rs2829984 |
| DPP6 | rs11975478 | QRICH2 | rs347675 | APP | rs2829989 |
| DPP6 | rs11976255 | PCBP3 | rs373617 | GRIK1 | rs2832409 |
| DPP6 | rs10280963 | RUVBL2 | rs3764622 | SETD4 | rs2835239 |
| DPP6 | rs4507681 | ACTR2 | rs3771099 | SETD4 | rs2835240 |
| DPP6 | rs6955717 | CRHR1 | rs3785877 | SETD4 | rs2835244 |
| DPP6 | rs7811481 | PCBP3 | rs3788216 | SETD4 | rs2835261 |
| DPP6 | rs6945869 | PCBP3 | rs3788217 | SETD4 | rs2835263 |
| DPP6 | rs4074568 | ARL15 | rs3797251 | MX1 | rs2838037 |
| DPP6 | rs4074817 | ARL15 | rs3797252 | PCBP3 | rs2839060 |
| DPP6 | rs4726385 | ARL15 | rs3797255 | SORD | rs2854549 |
| DPP6 | rs4380850 | QRICH2 | rs3803737 | MX1 | rs2898449 |
| DPP6 | rs12703323 | PDE1C | rs3807618 | ACCN1 | rs2932925 |
| DPP6 | rs9791911 | PCBP3 | rs381083 | SERPINB9 | rs318477 |
| DPP6 | rs4397308 | CIC | rs3826706 | SERPINB9 | rs318489 |
| DPP6 | rs10224365 | PCBP3 | rs3827268 | GRIK1 | rs363426 |
| DPP6 | rs10267846 | PRPSAP1 | rs385689 | GRIK1 | rs363452 |
| DPP6 | cnvi0096121 | SELE | rs3917410 | GRIK1 | rs363456 |
| DPP6 | cnvi0096122 | SELE | rs3917419 | GRIK1 | rs363463 |
| DPP6 | cnvi0096123 | ARL15 | rs445953 | GRIK1 | rs363464 |
| DPP6 | cnvi0096124 | PRPSAP1 | rs449114 | GRIK1 | rs363472 |
| DPP6 | cnvi0096125 | RGS12 | rs4690096 | GRIK1 | rs363478 |
| DPP6 | cnvi0096126 | PDE1C | rs4723103 | PCBP3 | rs373617 |
| DPP6 | rs10952466 | QRICH2 | rs4789267 | ACAT1 | rs3741049 |
| DPP6 | cnvi0096127 | CRHR1 | rs4792886 | SHANK1 | rs3745530 |
| DPP6 | rs10952467 | RUVBL2 | rs4802533 | SHANK1 | rs3745532 |
| DPP6 | cnvi0096128 | ARL15 | rs4865809 | RYR1 | rs3745844 |
| DPP6 | cnvi0096129 | BDKRB2 | rs4905466 | NMI | rs3771886 |
| DPP6 | rs10272007 | SELE | rs5353 | APP | rs3787625 |
| DPP6 | cnvi0096130 | SELE | rs5361 | ARL15 | rs3797269 |
| DPP6 | cnvi0096131 | SELE | rs5367 | APP | rs380417 |
| DPP6 | cnvi0096132 | SELE | rs5368 | PDE1C | rs3807618 |
| DPP6 | rs4726389 | GRIK3 | rs550115 | PCBP3 | rs381083 |
| DPP6 | rs12674128 | CALM1 | rs5871 | PCBP3 | rs3827268 |
| DPP6 | rs10254647 | CACYBP | rs6425310 | APP | rs383700 |
| DPP6 | rs12703329 | QRICH2 | rs6501880 | NMI | rs3856557 |
| DPP6 | rs12668613 | ACTR2 | rs6745303 | SHANK1 | rs3893128 |
| SGTB/NLN | rs112314 | NARG1 | rs6848950 | APP | rs396969 |
| SGTB/NLN | rs10073281 | GSN | rs7046030 | PCBP3 | rs406179 |
| SGTB/NLN | rs17590975 | GNAQ | rs7048503 | PRPSAP1 | rs407281 |
| SGTB/NLN | rs972501 | RUVBL2 | rs7256033 | PRPSAP1 | rs419793 |
| SGTB/NLN | rs252646 | RYR1 | rs7258075 | PCBP3 | rs431162 |
| USP24 | rs4367814 | GRIK3 | rs7517274 | NMI | rs446791 |
| USP24 | rs7527177 | SDC3 | rs7529390 | MX1 | rs457920 |
| USP24 | rs10888939 | PCBP3 | rs760436 | MX1 | rs459498 |
| USP24 | rs4512692 | RGS12 | rs762864 | MX1 | rs466513 |
| USP24 | rs6588574 | PDE1C | rs7787057 | MX1 | rs468105 |
| USP24 | rs4333889 | MTHFD1 | rs8003379 | MX1 | rs468440 |
| USP24 | rs10493190 | MTHFD1 | rs8011839 | MX1 | rs468646 |

TABLE 13B-continued

A SNPList available for implementation in a diagnostic array.

| Gene | SNP | Gene | SNP | Gene | SNP |
|---|---|---|---|---|---|
| SLC7A10 | rs752503 | BDKRB2 | rs8013400 | MX1 | rs469083 |
| SLC7A10 | rs748680 | QRICH2 | rs8074821 | PDE1C | rs4723103 |
| SLC7A10 | rs7256230 | CNP | rs8078650 | PSMD13 | rs473151 |
| SLC7A10 | rs10500264 | MAPK1 | rs8136867 | PXN | rs4767884 |
| SLC7A10 | rs4530278 | MAPK1 | rs8141815 | PXN | rs4767886 |
| SLC7A10 | rs736289 | TNIK | rs952209 | SHANK1 | rs4801850 |
| CNTN4 | rs9825865 | MAPK1 | rs9610417 | FPR1 | rs4801891 |
| CNTN4 | rs10510218 | TK1 | rs9897269 | SHANK1 | rs4802724 |
| CNTN4 | rs12488941 | CA8 | rs10092625 | SHANK1 | rs4802731 |
| CNTN4 | rs9860556 | CA8 | rs10108007 | GSN | rs4837820 |
| CNTN4 | rs17044355 | PXN | rs10128770 | HTR2A | rs4942587 |
| CNTN4 | rs13322503 | PDE1C | rs10226190 | PSMD13 | rs505404 |
| CNTN4 | rs6781373 | GRM3 | rs1024516 | PSMD13 | rs577259 |
| CNTN4 | rs7625240 | PDE1C | rs10247918 | PSMD13 | rs577298 |
| CNTN4 | rs1387084 | PDE1C | rs1035028 | DYNLL1 | rs580016 |
| CTNNA2 | rs6547363 | PPP2R1A | rs10412613 | DYNLL1 | rs606443 |
| CTNNA2 | rs4430978 | PPP2R1A | rs10420138 | CA8 | rs6471849 |
| CTNNA2 | rs10208516 | PPP2R1A | rs10423794 | ACCN1 | rs6505377 |
| CTNNA2 | rs1595071 | PSMD13 | rs1045288 | PPP2R1A | rs6509626 |
| CTNNA2 | rs2862499 | CNR1 | rs1049353 | CA8 | rs6984526 |
| LARP7 | rs1565010 | ACCN1 | rs10512455 | CA8 | rs6986917 |
| LARP7 | rs12054518 | ACCN1 | rs10512456 | GRM3 | rs701332 |
| LARP7 | rs1129065 | SERPINB9 | rs1052886 | PSMD13 | rs7128029 |
| LARP7 | rs4834296 | GAPDH | rs1060619 | ACCN1 | rs7220709 |
| LARP7 | rs4409021 | GSN | rs10739593 | PPP2R1A | rs7251605 |
| LARP7 | cnvi0018439 | GSN | rs10760165 | FPR1 | rs7253284 |
| LARP7 | rs4488992 | GSN | rs10760167 | HTR2A | rs731779 |
| LARP7 | rs6533635 | CHRM3 | rs10802802 | CA8 | rs7465573 |
| LARP7 | rs11722959 | STRAP | rs10846246 | PDE1C | rs7787057 |
| LARP7 | rs4555714 | ACAT1 | rs10890819 | SORD | rs8043226 |
| LARP7 | rs11946967 | PSMD13 | rs10902112 | PRPSAP1 | rs8078771 |
| LARP7 | rs2352050 | RCC1 | rs10915206 | SHANK1 | rs8103945 |
| LARP7 | rs10031435 | CHRM3 | rs10925969 | PPP2R1A | rs8106271 |
| LARP7 | rs7690429 | CA8 | rs10957123 | MX1 | rs8132871 |
| LARP7 | rs4834302 | DISC1 | rs11122319 | PCBP3 | rs8133858 |
| RGS12 | rs10027926 | CACNA1B | rs11137372 | DISC1 | rs823161 |
| PCBP3 | rs1014446 | ACAT1 | rs11212525 | DISC1 | rs823162 |
| SDC3 | rs10158813 | PXN | rs1151824 | DISC1 | rs823163 |
| PDE1C | rs10226190 | PXN | rs1151832 | FPR1 | rs867228 |
| PDE1C | rs10247918 | PXN | rs1151836 | GSN | rs878691 |
| PDE1C | rs1035028 | NMI | rs11551174 | SETD4 | rs880221 |
| ARL15 | rs10513040 | CHRM3 | rs11578320 | GNAO1 | rs922445 |
| CALM1 | rs1058903 | SORD | rs11636774 | HTR2A | rs927544 |
| RUVBL2 | rs1062708 | ADCY1 | rs11766192 | CACNA1B | rs9314645 |
| TK1 | rs1065769 | CA8 | rs11784742 | SERPINB9 | rs9392442 |
| SDC3 | rs10753239 | RYR2 | rs11810113 | HTR2A | rs9534505 |
| GSN | rs10760169 | PPP2R1A | rs11881878 | HTR2A | rs9534507 |
| GSN | rs1078305 | DISC1 | rs12030517 | PSMD11 | rs9889352 |
| GNAQ | rs10869977 | DISC1 | rs12084975 | ACCN1 | rs9903823 |
| CRHR1 | rs110402 | ADCY1 | rs12112953 | PCBP3 | rs9975850 |
| | | CHRM3 | rs12124903 | | |

In additional studies, we have extended our previous GRM network analysis of CNVs to a more comprehensive network of 335 genes which show significance in ADHD. The original mGluR network was generated from 271 genes, including first and second degree interacting genes as defined by the Human Interactome. The updated analysis provides more comprehensive update of the mGluR network definition to better capture functional interactions of genes with GRMs.

To generate these additional targets, the following databases were employed:
1. The Ingenuity Knowledge Base of biological interactions and functional annotations. Each Ingenuity interaction has been manually created by expert scientists with supporting publications for specific interacting molecules.
2. Published GWAS results reported in the Human Genome Epidemiology (HuGE) Navigator, which is an integrated, searchable knowledge base of genetic associations and human genome epidemiology.
3. Our own literature review of PubMed for interactions with mGluR genes.
4. Rare variants from sequencing ADHD patients not found in public domain These updated networks were used to analyze 1292 ADHD cases compared to 7449 neurologically normal controls. Negative controls were used to validate the CNV analysis algorithms in the context of biologically relevant expectations like developmental pathways (HOX genexes), cancer (Lung cancer pathway) and neuronal signaling not implicated in ADHD (GABA). The network is highly significant with CNVs identified in 17% of cases overall and 9% of controls, with OR of 2.1 and P=$6.5 \times 10^{-17}$. Table 13C provides the names of 64 additional genes to the 271 presented (total of 335) that were identified using the Ingenuity software. The updated analysis provides functional interactions of genes with GRMs based on the Ingenuity Knowledge Base of biological interactions and functional annotations. Each Ingenuity interaction has been manually created by expert scientists with supporting publications for specific interacting molecules.

Results from the extended CNV analysis are as follows:

| Dataset | # genes | $F_{cases}$ | $F_{controls}$ | P | OR |
|---|---|---|---|---|---|
| Original + Ingenuity (ADHD GRMs) | 335 | 0.17 | 0.09 | $6.5 \times 10^{-17}$ | 2.1 |
| Hox (−ve control) | 38 | 0.003 | 0.002 | 0.43 | 1.2 |
| Lung Cancer (−ve control) | 421 | 0.17 | 0.19 | 0.99 | 0.8 |
| GABA Signaling (−ve control) | 121 | 0.03 | 0.07 | 0.99 | 0.3 |

(2002). More preferably, the treating agent is a pyroglutamide. Details regarding the preparation and formulation of pyroglutamides which may be used in the practice of this invention are provided in U.S. Pat. No. 5,102,882 to Kimura et al. A particularly preferred agent for the treatment of ADHD in patients determined to have one or more of the SNPs indicative of the presence of an ADHD-associated copy number variation, as set forth in Table 13, is (+)-5-oxo-D-prolinepiperidinamide monohydrate (NS-105).

Example III

The above-identified CNV containing mGluR genes involved in ADHD pathogenesis also provide novel targets

TABLE 13C

335 Targets are listed herein below (includes the 271 targets from Table 13A).

| | | | | | | | | |
|---|---|---|---|---|---|---|---|---|
| ACAT1 | CACNA1A | ERBB2 | GRM2 | MIR1236 | PCBP3 | PSMD11 | SET | TRPV1 |
| ACAT2 | CACNA1B | ERBB4 | GRM3 | MIR1245 | PCDHA4 | PSMD13 | SETD4 | TUBA1A |
| ACCN1 | CACYBP | ESR1 | GRM4 | MIR1246 | PCMT1 | PSMD6 | SF3B14 | TUBA1B |
| ACCN2 | CALB2 | F2R | GRM5 | MIR1252 | PDCD5 | PSME1 | SHANK1 | TUBA8 |
| ACP1 | CALM1 | F2RL2 | GRM6 | MIR1260 | PDE1B | PTK2B | SHANK3 | TUBB |
| ACTB | CALM2 | F2RL3 | GRM7 | MIR1262 | PDE1C | PXN | SHBG | TUBG1 |
| ACTN1 | CALM3 | F3 | GRM8 | MIR1272 | PDE6G | PYGL | SIAH1 | TXN |
| ACTR2 | CAMK1 | FGF2 | GSN | MIR1275 | PGM1 | PYGM | SIM1 | TYMS |
| ADA | CAMK2B | FKBP3 | HBXIP | MIR1276 | PHKB | QRICH2 | SLC1A2 | UBE2I |
| ADCY1 | CAMK4 | FLNA | HOMER1 | MIR1284 | PHKG2 | RALA | SLC2A1 | UBE2M |
| ADD1 | CASR | FOS | HOMER2 | MIR1291 | PIAS1 | RANBP1 | SLC6A3 | UBQLN4 |
| ADD2 | CAV1 | FPR1 | HOMER3 | MIR1305 | PIAS2 | RANBP9 | SLC9A3R1 | UCHL1 |
| ADORA1 | CAV3 | FSCN1 | HSP90AB1 | MIR1322 | PIAS4 | RAP2A | SLC9A3R2 | VHL |
| ADORA2A | CBX7 | FURIN | HTR2A | MIR1323 | PICK1 | RCC1 | SNCA | VIPR1 |
| ADRA1B | CCNB1 | FYN | HTT | MIR1324 | PIK3CA | RCC2 | SNRPB2 | YWHAQ |
| ADRA2A | CDC42 | GAPDH | IFNG | MIR555 | PIK3R1 | RGS11 | SOCS6 | ZAP70 |
| ADRA2C | CHGB | GLP1R | IMPDH2 | MIR559 | PLA2G7 | RGS12 | SOCS7 | |
| ADRB2 | CHP | GLP2R | IQGAP2 | MIR591 | PLCB1 | RGS2 | SORD | |
| ADRBK1 | CHRM2 | GNA15 | ITGB1 | MIR610 | PLCB3 | RGS3 | SRC | |
| ADRBK2 | CHRM3 | GNAI1 | ITGB7 | MIR637 | PLCG2 | RGS4 | STAU1 | |
| ALDOA | CIC | GNAI2 | ITPR1 | MIR641 | PLD1 | RGS9BP | STRAP | |
| ANXA2 | CNP | GNAI3 | KIAA0090 | MIR769 | POMC | RHOA | STX12 | |
| APTX | CNR1 | GNAO1 | KIAA1683 | MRPL14 | PPIH | RIF1 | SUMO1 | |
| AQP1 | COPB2 | GNAQ | KLHL17 | MRPS16 | PPM1A | ROCK2 | SYK | |
| ARHGAP24 | CRHR1 | GNB2L1 | KPNA1 | MTHFD1 | PPM1B | RPA2 | TBCA | |
| ARL15 | CYCS | GNB5 | KPNA3 | MTNR1A | PPM1D | RPLP2 | TBXA2R | |
| ARNT2 | CYTH2 | GOPC | LAMA4 | MTNR1B | PPM1G | RPN2 | TCP1 | |
| ARRB1 | CYTIP | GOT1 | LRP2BP | MX1 | PPP1CC | RPS14 | TEAD3 | |
| ARRB2 | DCN | GP1BA | LRRC59 | MYO6 | PPP2R1A | RRM1 | TFAM | |
| ATXN7L3 | DHCR7 | GPR26 | LTA | NANS | PRDX1 | RUVBL2 | TGFB1 | |
| BDKRB1 | DLST | GRASP | LYAR | NCK1 | PRKCA | RYR1 | TGM2 | |
| BDKRB2 | DNM3 | GRB7 | LYN | NFKBIA | PRKCG | RYR2 | TJP1 | |
| BDNF | DRD2 | GRIA1 | MAGI2 | NMI | PRLHR | S100A6 | TK1 | |
| BTBD2 | DRD3 | GRIK3 | MAP4 | NPY2R | PRMT1 | SACS | TLR10 | |
| BTG2 | DSTN | GRIN1 | MAPK1 | NR3C1 | PRPSAP1 | SARS | TNIK | |
| C17orf44 | DYNLL1 | GRIP1 | MAPK3 | NUDC | PSAT1 | SCTR | TPI1 | |
| C1orf116 | ECHS1 | GRK4 | MARK4 | OPRD1 | PSEN1 | SDC3 | TRAF2 | |
| C7orf25 | EFNB2 | GRK5 | MC4R | OPTN | PSMA1 | SDCBP | TRMT112 | |
| CA8 | EGFR | GRK6 | MIR1200 | PAFAH1B3 | PSMC1 | SELE | TRPC1 | |
| ACAT1 | EPHB1 | GRM1 | MIR1207 | PCBP1 | PSMD1 | SERPINB9 | TRPC3 | |

In accordance with the present invention, it has been found that 10% of patients with ADHD carry specific types of mutations of genes that encode for metabotropic glutamate receptors (mGluRs). These mutations are sensitive and specific biomarkers for selecting and treating ADHD due to defective mGluR pathways. Furthermore, the present inventors have identified drug candidates that specifically activate the mGluRs, potentially restoring normal neurophysiology in ADHD patients with mutations in the GRM family of mGluR genes. See Table 1.

For example, compounds which may be administered in implementing the test and treat paradigm described herein include the piracetam family of nootropic agents, as described in F. Gualtieri et al., Curr. Pharm. Des., 8: 125-38 for the development of new therapeutic agents efficacious for the treatment of ADHD. To that end, methods of screening of candidate drug (agent or compound) that modulates mGluR protein interactions and associated pathology can be performed based on the information provided herein. Representative candidate drugs include nucleic acids, polypeptides, small molecule compounds and peptidomimetics.

In some cases, genetic agents can be screened by contacting the yeast cell with a nucleic acid construct coding for a gene. For example, one may screen cDNA libraries expressing a variety of genes, to identify other genes that modulate such interactions. For example, the identified drugs may modulate glutamate associated neuronal signaling, subcellular protein localization and/or neuronal cell morphology or viability. Accordingly, irrespective of the exact mechanism of action, drugs identified by the screening methods described herein are expected to provide therapeutic benefit to patients suffering from ADHD.

Suitable screening methods may employ a variety of neuronal cell types obtainable from the ATCC. Candidate drugs can be screened from large libraries of synthetic or natural compounds. One example is an FDA approved library of compounds that can be used by humans. In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofme (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd. (Moscow, Russia), Princeton Biomolecular (Monmouth Junction, N.J.), Scientific Exchange (Center Ossipee, N.H.), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China). Combinatorial libraries are available and can be prepared. Libraries of natural compounds in the form of bacterial, fungal, plant and animal extracts are commercially available or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds.

For example, the neuronal cells can be incubated in the presence and absence of a test compound, such as pyroglutamides (see, e.g., U.S. Pat. No. 5,102,882) and other members of the piracetam family of nootropic agents, after which the effect of the compound on glutamate signaling is assessed. Agents so identified could then be tested in whole animal models of ADHD to assess in vivo efficacy.

Agents identified using the screening assays described herein are also encompassed by the present invention.

Discussion

At present, there is a notable paucity of genome wide association studies in ADHD, and no study has reported CNVs that are significantly associated with ADHD. As such, our study represents the first large-scale, unbiased two-stage genome-wide scanning of CNVs in ADHD. Although we have previously reported GRM5 deletion in a single ADHD family with three affected children and one family with GRM7 deletion, along with 57 other non-GRM receptor genes, most of which were single events[13], the genes from the metabotropic glutamate receptor family (GRM5, GRM7, GRM8 and GRM1) are for the first time shown to be impacted by CNVs that significantly associate with ADHD and observed to replicate in multiple independent case control data sets.

Metabotropic glutamate receptors (GRMs or mGluRs) are a class of G-protein-coupled receptors that possess a seven transmembrane region involved in the modulation of excitatory synaptic transmission in the nervous system[14]. There are three receptor groups based on sequence homology, putative signal transduction mechanisms, and pharmacologic properties[15]. GRM5 and GRM1 are members of Group I expressed particularly in the basal ganglia and cerebellum[16], relevant brain areas for ADHD. These receptors have been shown to activate phospholipase C and it has been postulated they may play a role in addiction, anxiety and behavioral disorders[17]. GRM7 and GRM8 are members of Group III which is linked to the inhibition of the cyclic AMP cascade. GRM7 has been linked with anxiety[18] and is the most highly conserved of all mGluR subtypes across different mammalian species[19].

Evidence for glutamatergic involvement in ADHD is arising from diverse fields. While association studies investigating variants in glutamatergic receptors and transporters have reported mixed results[20-23] a genome-wide association study investigating response to the methylphenidate in ADHD children detected nominal evidence for association of several SNPs including SNPs within GRM7 (rs3792452)[24]. GRIN2A was reportedly associated with ADHD in a genetic linkage study[20] and GRIN2B was associated by TDT[25]. Magnetic resonance spectroscopy studies have shown increased glutamatergic tone in frontal and striatal brain regions of ADHD subjects[26-28] which normalizes with stimulants and atomoxetine[29]. The SLC6A3 KO (DAT-KO) mouse, an ADHD animal model, remains responsive to methylphenidate in spite of the lack of a dopamine transporter[30] and hyperactivity in these mice can be increased by NMDA-receptor blockers and suppressed by drugs that increase glutamatergic transmission[31]. Increased midbrain SLC6A3 and DRD4 expression were reported in rats where glutamate transporter increases were found in the striatum[32] suggesting that decreases in dopamine may alter glutamate signaling. Also, glutamate receptor subunit gene (GRIN2A) disruption increased DA and serotonin metabolism in the frontal cortex and striatum of mice, and increased locomotor activity that was reduced by dopamine or serotonin receptor antagonists[33]. Moreover, dysregulated expression of genes in glutametergic pathways has been observed in the SHR[34-37] and in the PCB exposed rat model of ADHD[36]. Increased levels of glutamate have been reported in the neurometabolism of ADHD brains, suggesting that altered glutamate transmission may be important in ADHD[28]. Although the glutamate receptors that associated with ADHD in our study were deleted in three instances and duplicated in one instance, the resulting perturbations in glutamate signaling in the deleted cases could promote ADHD through a feedback loop releasing additional glutamate in an attempt to compensate for the disparity of sent and received neurotransmission signals.

Apart from the GRM family of genes, we have detected association of eight other loci with ADHD, four of which directly impact genes (Table 3B). Among those are genes with intriguing biology with respect to ADHD. DPP6 has been previously associated with Amyotrophic Lateral Sclerosis (ALS) in genome wide association studies[38,39], and CNVs impacting DPP6 have been reported in relation with autism[40]. DPP6 and CTNNA2 (although our association does not directly impact CTNNA2) have been implicated by earlier ADHD SNP genotype GWAS[9]. NLN is an interesting candidate responsible for metabolic inactivation of neural peptides, such as Neuropeptide Y (NPY) which has previously been implicated in ADHD[45,46]. SLC7A10 has been shown to play a role in the modulation of glutamatergic transmission through mobilization of D-serine at the glutamatergic synapse. LARP7 is important for snRNP integrity, a protein complex responsible for post transcriptional splicing. NEGR1 encodes a neural cell adhesion molecule and a trans-neural growth-promoting factor in regenerative axon sprouting and neuronal growth in the mammalian brain. Interestingly, this neuronal gene was recently associated with obesity[41].

In the CHOP discovery cohort, Family 230 is impacted with both GRM5 deletion inherited from the mother and NEGR1 duplication inherited from the father in all three ADHD cases in the family. In spite of superior IQ levels these 3 children had severe impairment. These were the only CNV regions observed in all three familial cases and not observed in controls. Assessment of the mother using an adult ADHD Self-Report Scale[42] indicated a likelihood of ADHD.

There are eight CNVRs presented that directly disrupt the respective gene in these regions (including GRM5, GRM7, GRM8, GRM1 NEGR1, DPP6, SGTB/NLN and LARP7) while the remainder are annotated with the closest (Table 3A and 3B). Furthermore, GRM8, GRM1 SGTB/NLN, and LARP7 CNVs are exonic. Further functional studies to fully characterize the function of the associated genes in relation with the ADHD phenotypes will be conducted. Thus, our unbiased approach to assess the entire genome in multiple independent cohorts has revealed CNVs in novel genes that have not previously been studied for any potential biological or physiological impact on the brain in ADHD and await further characterization.

Given the significance of the four GRM receptor genes reported in ADHD pathogenesis and the rarity of CNVs at each of the loci, we elected to evaluate GRM receptor interacting genes for their frequency of CNV observations in cases and controls. This allows for inclusion of marginally significant loci given the prior knowledge of robust association of the GRM receptor gene family. CNVs are often very rare (<1%) at a given locus but their associations provide stronger direct correlation to the disease state than common variants as evidenced by their impressive effect sizes (see ORs in Table 3). Based on individually significant loci alone, 3.66% of ADHD cases are strongly correlated with the CNVs discovered. By extending the observations from the confident GRM family to gene networks of GRM receptor interacting/signaling genes provides 9.94% of ADHD cases with genetic characterization of their disease after adjusting for control frequency (i.e., net impact in cases). Major supporting hubs of this network include TNIK[48], GNAQ[49], and CALM1[50] (FIG. 11), previously associated with schizophrenia and epilepsy. Interestingly, the GRM receptor network gene, GRIK1, has also been associated with hyperactive/impulsive symptoms of ADHD[8].

Taken together, our analysis of CNVs and functional enrichment of the GRM receptor gene interaction network suggests that GRMs do not form a large number of interactions, but serve to coordinate functional modules of other sets of genes. Encouragingly, some of these modules are important in the process of synaptic transmission, neurogenesis, and other neuronal processes thought to be defective in ADHD. Thus, through network analysis of CNVs impacting ADHD, we have identified modules that are important in processes such as RNA binding, processing, and alternative splicing, which have been shown to influence brain-specific synaptic activity[51,52]. Also, we have identified functional modules involved in ubiquitination, a process that we have previously linked to autism[1], which shares certain phenotypic features with ADHD. Furthermore, abnormal functional brain connectivity is a candidate factor in developmental brain disorders associated with cognitive dysfunction, including ADHD[53,54]. Thus, the impact CNVRs among the GRM family of receptors, and in particular GRM5 and GRM7, may be important to the underlying molecular etiology of ADHD.

In conclusion, using a two-stage genome-wide association approach for high-resolution CNV detection, we have identified 12 loci demonstrating enrichment of CNVs in ADHD cases as compared to controls, and successfully replicated 4 of them using independent data sets of ADHD cases and healthy controls genotyped on three different platforms matched for cases and controls. Four of the genes affected belong to the metabotropic glutamate receptor family. The network of over 200 genes interacting with glutamate receptors are collectively impacted with CNVs and capture the genetic diversity of approximately 10% of all ADHD cases. Furthermore, this network of genes interacting with the metabotropic glutamate receptors defines a set of functional modules with significant neuronal functions, defects of which are thought to underlie ADHD and other neurodevelopmental disorders. Therefore, the enrichment of genes within this molecular system for CNVs associated with ADHD suggests novel susceptibility mechanisms for the disease and will spur assessment of additional variations, including structural variations and single-base changes in candidate genes within these molecular networks. Our results call for expression and other functional assays to assess the biological effects of CNVs in these candidate genes.

TABLE 14

ADHD CNV Family Based Transmission Disequilibrium and de novo Statistical Tests.

A) Illumina CHOP Deletions Enriched for Inheritance

| CNVR | Count SNPs | TDTDel | InhDel | de novo Del | ParDel NotInh | Gene | Distance |
|---|---|---|---|---|---|---|---|
| chr18: 74258734-74260996 | 3 | 0.001953 | 9 | 0 | 0 | SALL3 | 580267 |
| chr7: 120092385-120099982 | 3 | 0.001953 | 9 | 0 | 0 | KCND2 | 0 |
| chr4: 92499956-92502794 | 8 | 0.001953 | 9 | 0 | 0 | KIAA1680 | 0 |
| chr11: 69755529-69759313 | 12 | 0.007813 | 7 | 0 | 0 | FADD | 24395 |
| chr4: 42400885-42403451 | 15 | 0.007813 | 7 | 0 | 0 | ATP8A1 | 47238 |
| chr5: 104463047-104518786 | 17 | 0.007813 | 7 | 0 | 0 | NR_000039 | 0 |
| chr13: 69637654-69666685 | 18 | 0.015625 | 6 | 0 | 0 | NR_002717 | 25969 |
| chr3: 195971510-195982215 | 5 | 0.03125 | 5 | 1 | 0 | FAM43A | 80455 |

TABLE 14-continued

ADHD CNV Family Based Transmission Disequilibrium and de novo Statistical Tests.

| | | | | | | |
|---|---|---|---|---|---|---|
| chr19: 44369918-44376749 | 3 | 0.03125 | 5 | 1 | 0 | LOC342897 | 2695 |
| chr1: 2349841-2356176 | 4 | 0.03125 | 5 | 1 | 0 | PEX10 | 15971 |
| chr21: 45777720-45782727 | 3 | 0.03125 | 5 | 0 | 0 | SLC19A1 | 0 |
| chr10: 67748487-67785209 | 30 | 0.03125 | 5 | 0 | 0 | CTNNA3 | 0 |

B) Illumina CHOP Duplications Enriched for Inheritance

| CNVR | Count SNPs | TDTDup | InhDup | de novo Dup | ParDup NotInh | Gene | Distance |
|---|---|---|---|---|---|---|---|
| chr20: 59015708-59022667 | 4 | 0.007813 | 7 | 0 | 0 | CDH4 | 238287 |
| chr12: 72808323-72832667 | 5 | 0.015625 | 6 | 0 | 0 | BC061638 | 0 |
| chr6: 73021641-73023171 | 3 | 0.03125 | 5 | 0 | 0 | RIMS1 | 0 |
| chr17: 74089903-74106726 | 9 | 0.03125 | 5 | 0 | 0 | DNAHL1 | 10904 |
| chr1: 9243828-9310031 | 22 | 0.03125 | 5 | 0 | 0 | H6PD, SPSB1 | 0 |

C) Illumina CHOP Deletions Enriched for de novo

| CNVR | Count SNPs | de novo TDTDel | InhDel | de novo Del | ParDel NotInh | Gene | Distance |
|---|---|---|---|---|---|---|---|
| chr16: 87694595-87778383 | 16 | 3.02E−05 | 32 | 2 | 21 | AX748415, CDH15, LOC197322 | 0 |
| chr18: 65358832-65367619 | 18 | 3.02E−05 | 33 | 2 | 21 | DOK6 | 0 |
| chr12: 55902280-55923860 | 3 | 0.000367 | 9 | 3 | 19 | NDUFA4L2, NXPH4, SHMT2, STAC3 | 0 |
| chr17: 71112486-71120734 | 4 | 0.001848 | 12 | 3 | 16 | KIAA1783 | 0 |
| chr22: 38384374-38403731 | 8 | 0.018158 | 4 | 4 | 13 | CACNA1I | 0 |
| chr19: 15992679-15997923 | 2 | 0.025875 | 15 | 6 | 15 | LOC126536 | 0 |

D) Illumina CHOP Duplications Enriched for de novo

| CNVR | Count SNPs | de novo TDTDup | InhDup | de novo Dup | ParDup NotInh | Gene | Distance |
|---|---|---|---|---|---|---|---|
| chr19: 59423491-59428132 | 12 | 4.85E−09 | 74 | 3 | 38 | LILRB3, LIR-3 | 0 |
| chr8: 145217675-145247517 | 4 | 3.05E−05 | 19 | 0 | 15 | CYC1, MAF1, SHARPIN, hSIPL1A | 0 |
| chr18: 64897188-64906488 | 48 | 0.000122 | 9 | 0 | 13 | CCDC102B | 23782 |
| chr14: 104225150-104339273 | 35 | 0.00293 | 7 | 1 | 11 | ADSS, ADSSL1, AKT1, SIVA1 | 0 |
| chr9: 138606913-138647195 | 17 | 0.005371 | 10 | 1 | 10 | AF161442 | 15688 |
| chr16: 650256-2028586 | 41 | 0.015625 | 8 | 0 | 6 | Many | 0 |
| chr20: 61642713-61668792 | 11 | 0.03125 | 4 | 1 | 7 | C20orf195, PRIC285, SRMS | 0 |
| chr16: 87399730-87430019 | 22 | 0.03125 | 7 | 1 | 7 | APRT, CDT1, FLJ00319, GALNS | 0 |
| chr16: 3553005-3590430 | 20 | 0.03125 | 8 | 0 | 5 | BTBD12, NLRC3 | 0 |
| chr22: 17257787-17355587 | 60 | 0.03125 | 3 | 0 | 5 | DGCR6, KIAA1647, PRODH | 0 |

E) Perlegen IMAGE Deletions Enriched for Inheritance

| CNVR | Count SNPs | TDTDel | InhDel | de novo Del | ParDel NotInh | Gene | Distance |
|---|---|---|---|---|---|---|---|
| chr2: 180271795-180274556 | 5 | 0.003204 | 2 | 1 | 13 | ZNF533 | 0 |
| chr14: 79919894-79924934 | 5 | 0.03125 | 1 | 0 | 7 | BC039670 | 0 |
| chr7: 19828746-19840916 | 7 | 0.041656 | 4 | 0 | 11 | MGC42090 | 49005 |

TABLE 14-continued

ADHD CNV Family Based Transmission Disequilibrium and de novo Statistical Tests.

F) Perlegen IMAGE Duplications Enriched for Inheritance

| CNVR | Count SNPs | TDTDup | InhDup | de novo Dup | ParDup NotInh | Gene | Distance |
|---|---|---|---|---|---|---|---|
| chr22: 17361563-17369020 | 3 | 0.015625 | 6 | 0 | 0 | CR623368, KIAA1647 | 0 |
| chr15: 30088094-30090949 | 3 | 0.03125 | 5 | 1 | 0 | CHRNA7 | 19069 |
| chr7: 71664963-71712086 | 5 | 0.03125 | 5 | 0 | 0 | MGC87315 | 0 |

G) Perlegen IMAGE Deletions Enriched for de novo

| CNVR | Count SNPs | Denovo TDTDel | InhDel | de novo Del | ParDel NotInh | Gene | Distance |
|---|---|---|---|---|---|---|---|
| chr2: 180271795-180274923 | 6 | 0.000854 | 2 | 1 | 13 | ZNF533 | 0 |
| chr10: 85445139-85446804 | 7 | 0.03125 | 5 | 1 | 7 | GHITM | 442361 |

H) Perlegen IMAGE Duplications Enriched for de novo

| CNVR | Count SNPs | Denovo TDTDup | InhDup | de novo Dup | ParDup NotInh | Gene | Distance |
|---|---|---|---|---|---|---|---|
| chr12: 31276361-31285014 | 9 | 6.87E-05 | 15 | 1 | 17 | OVOS2 | 26006 |
| chr10: 47089854-47154881 | 31 | 6.87E-05 | 11 | 1 | 17 | AK057316 | 0 |
| chr7: 140018-162903 | 13 | 0.005371 | 10 | 1 | 10 | AL137655 | 23529 |
| chr8: 2437197-2492653 | 23 | 0.03125 | 4 | 1 | 7 | BC045738 | 0 |
| chr6: 168234697-168295618 | 13 | 0.043945 | 5 | 2 | 8 | FLJ00181 | 9639 |

TABLE 15

ADHD CNV Family Based Transmission Disequilibrium and de novo Statistical Tests.

| CNVR (hg18/B36/March 2006) | Type | TDTDel | TDTDup | de novo TDTDel | de novo TDTDup | InhDel | de novo Del | ParDel NotInh | InhDup | de novo Dup | ParDup NotInh |
|---|---|---|---|---|---|---|---|---|---|---|---|
| chr7: 126441593-126621501 | Del | 1 | 1 | 1 | 1 | 0 | 0 | 0 | 0 | 0 | 0 |
| chr11: 88269449-88351661 | Del | 0.125 | 1 | 0 | 1 | 3 | 0 | 0 | 0 | 0 | 0 |
| chr3: 7183953-7197236 | Del | 0.25 | 1 | 1 | 1 | 2 | 0 | 0 | 0 | 0 | 0 |
| chr6: 146657076-146694047 | Dup | 1 | 1 | 1 | 1 | 0 | 0 | 0 | 0 | 0 | 0 |
| chr7: 153495598-153564827 | Dup | 0.205 | 1 | 0.016 | 1 | 4 | 0 | 6 | 0 | 0 | 0 |
| chr5: 65027976-65046520 | Del | 1 | 0.5 | 1 | 1 | 0 | 0 | 0 | 1 | 0 | 0 |
| chr1: 56053497-56064495 | Del | 1 | 1 | 1 | 1 | 0 | 0 | 0 | 0 | 0 | 0 |
| chr1: 72317292-72328395 | Dup | 1 | 1 | 1 | 1 | 0 | 0 | 0 | 0 | 0 | 0 |
| chr19: 38427720-38444834 | Del | 0.183 | 1 | 0.004 | 1 | 6 | 0 | 8 | 0 | 0 | 0 |
| chr3: 1844168-1859889 | Del | 0.063 | 1 | 0 | 1 | 4 | 0 | 0 | 0 | 0 | 0 |
| chr2: 81419297-81446082 | Dup | 1 | 0.5 | 1 | 1 | 0 | 0 | 0 | 1 | 0 | 0 |
| chr4: 113772340-113788584 | Dup | 0.375 | 1 | 0.5 | 1 | 2 | 0 | 1 | 0 | 0 | 0 |

TABLE 16

Sample Source Contributions to Impacting CNV Loci.

| CNVR | CHOP Cases | CHOP Controls | NIMH cases | Utah cases | IMAGE cases | Per Psoriasis Control | Per Depression Control | PUWMa Cases |
|---|---|---|---|---|---|---|---|---|
| chr11: 88269449-88351661 | 4 | 0 | 0 | 0 | 5 | 0 | 0 | 1 |
| chr7: 126441593-126621501 | 3 | 0 | 0 | 0 | 3 | 0 | 0 | 2 |
| chr3: 7183953-7197236 | 4 | 0 | 0 | 0 | 2 | 0 | 0 | 0 |
| chr6: 146657076-146694047 | 5 | 2 | 1 | 1 | 0 | 0 | 0 | 0 |
| chr1: 72317292-72328395 | 4 | 0 | 0 | 0 | 0 | 0 | 0 | 1 |
| chr7: 153495598-153564827 | 5 | 0 | 1 | 0 | 0 | 0 | 0 | 2 |
| chr5: 65027976-65046520 | 4 | 0 | 0 | 0 | 1 | 0 | 0 | 0 |
| chr1: 56053497-56064495 | 2 | 0 | 0 | 0 | 3 | 0 | 0 | 0 |
| chr19: 38427720-38444834 | 5 | 2 | 0 | 0 | 1 | 0 | 0 | 1 |
| chr3: 1844168-1859889 | 4 | 0 | 0 | 0 | 0 | 0 | 0 | 2 |

TABLE 16-continued

Sample Source Contributions to Impacting CNV Loci.

| CNVR | PUWMa Parents | IMAGE II Cases | IMAGE II Controls | SAGE Illumina 1M Controls | AGRE Affy 5.0 Parents Controls | | Type | Gene |
|---|---|---|---|---|---|---|---|---|
| chr2: 81419297-81446082 | 2 | 0 | 0 | 0 | 1 | 0 | 3 | 0 |
| chr4: 113772340-113788584 | 2 | 0 | 0 | 0 | 1 | 0 | 0 | 1 |

| CNVR | PUWMa Parents | IMAGE II Cases | IMAGE II Controls | SAGE Illumina 1M Controls | AGRE Affy 5.0 Parents Controls | Type | Gene |
|---|---|---|---|---|---|---|---|
| chr11: 88269449-88351661 | 1 | 0 | 0 | 0 | 0 | Del | GRM5 |
| chr7: 126441593-126621501 | 0 | 0 | 0 | 0 | 0 | Del | GRM8 |
| chr3: 7183953-7197236 | 0 | 0 | 0 | 0 | 0 | Del | GRM7 |
| chr6: 146657076-146694047 | 0 | 1 | 0 | 0 | 0 | Dup | GRM1 |
| chr1: 72317292-72328395 | 0 | 0 | 0 | 0 | 0 | Dup | NEGR1 |
| chr7: 153495598-153564827 | 0 | 0 | 1 | 0 | 1 | Dup | DPP6 |
| chr5: 65027976-65046520 | 0 | 1 | 1 | 0 | 0 | Del | SGTB/NLN |
| chr1: 56053497-56064495 | 0 | 1 | 0 | 0 | 2 | Del | USP24 |
| chr19: 38427720-38444834 | 3 | 0 | 0 | 0 | 0 | Del | SLC7A10 |
| chr3: 1844168-1859889 | 2 (inh) | 1 | 1 | 4 | 1 | Del | CNTN4 |
| chr2: 81419297-81446082 | 0 | 1 | 0 | 0 | 0 | Dup | CTNNA2 |
| chr4: 113772340-113788584 | 1 | 0 | 0 | 1 | 1 | Dup | LARP7 |

TABLE 17

Boundaries of Individual CNVs in Table 1A and 1B.

| CNVR | Gene | Type | Sample ID | Region Called in Sample | Exon Distance* | Sample Validation Run |
|---|---|---|---|---|---|---|
| chr11: 88269449-88351661 | GRM5 | Del | 230-3 | chr11: 88269449-88351661 | 5,858 | Y |
| chr11: 88269449-88351661 | GRM5 | Del | 230-4 | chr11: 88269449-88351661 | 5,858 | Y |
| chr11: 88269449-88351661 | GRM5 | Del | 230-5 | chr11: 88269449-88351661 | 5,858 | Y |
| chr11: 88269449-88351661 | GRM5 | Del | 497 | chr11: 83876556-91038751 | 0 | Y |
| chr11: 88269449-88351661 | GRM5 | Del | 16794 | chr11: 87996654-88837360 | 0 | Y |
| chr11: 88269449-88351661 | GRM5 | Del | 13304 | chr11: 88109331-88827923 | 0 | Y |
| chr11: 88269449-88351661 | GRM5 | Del | 13270 | chr11: 88115425-88481107 | 0 | Y |
| chr11: 88269449-88351661 | GRM5 | Del | 13761 | chr11: 88305340-88385387 | 0 | Y |
| chr11: 88269449-88351661 | GRM5 | Del | 17580 | chr11: 88305340-88385387 | 0 | N^ |
| chr11: 88269449-88351661 | GRM5 | Del | M.Of.M.Cs.604401 | chr11: 88324615-88342595 | 14,924 | Y |
| chr7: 126441593-126621501 | GRM8 | Del | 1953313026_A | chr7: 126532786-126536202 | 0 | Y |
| chr7: 126441593-126621501 | GRM8 | Del | 1965040688_A | chr7: 126463602-126478050 | 54,536 | Y |
| chr7: 126441593-126621501 | GRM8 | Del | 4011452014_A | chr7: 126532786-126536202 | 0 | Y |
| chr7: 126441593-126621501 | GRM8 | Del | 14125 | chr7: 125660695-126036276 | 0 | N^ |
| chr7: 126441593-126621501 | GRM8 | Del | 16794 | chr7: 125660695-126036276 | 0 | N^ |
| chr7: 126441593-126621501 | GRM8 | Del | 11804 | chr7: 125679479-125937528 | 0 | N^ |
| chr7: 126441593-126621501 | GRM8 | Del | 987314 | chr7: 126503602-126563602 | 0 | Y |
| chr7: 126441593-126621501 | GRM8 | Del | 987124 | chr7: 126463602-126603602 | 0 | Y |
| chr3: 7183953-7197236 | GRM7 | Del | 2023340146 | chr3: 7053179-7144453 | 18,686 | Y |
| chr3: 7183953-7197236 | GRM7 | Del | 068-3 | chr3: 7183954-7197236 | 20,599 | Y |
| chr3: 7183953-7197236 | GRM7 | Del | 068-4 | chr3: 7183954-7197236 | 20,599 | Y |
| chr3: 7183953-7197236 | GRM7 | Del | 4079019863_A | chr3: 7183954-7197236 | 20,599 | Y |
| chr3: 7183953-7197236 | GRM7 | Del | 11891 | chr3: 6979874-7003319 | 101,280 | Y |
| chr3: 7183953-7197236 | GRM7 | Del | 11923 | chr3: 6980446-7001696 | 101,852 | Y |
| chr6: 146657076-146694047 | GRM1 | Dup | 388-3 | chr6: 146657077-146675511 | 0 | Y |
| chr6: 146657076-146694047 | GRM1 | Dup | 387-3 | chr6: 146657077-146675511 | 0 | Y |
| chr6: 146657076-146694047 | GRM1 | Dup | 386-3 | chr6: 146657077-146675511 | 0 | Y |
| chr6: 146657076-146694047 | GRM1 | Dup | 4301337678_R02C01 | chr6: 146657077-146675511 | 0 | Y |
| chr6: 146657076-146694047 | GRM1 | Dup | 4305910011_R01C02 | chr6: 146657077-146675511 | 0 | Y |
| chr6: 146657076-146694047 | GRM1 | Dup | 1181 | chr6: 146657077-146694047 | 0 | Y |
| chr6: 146657076-146694047 | GRM1 | Dup | 83158 | chr6: 146657077-146694047 | 0 | Y |
| chr6: 146657076-146694047 | GRM1 | Dup | b3_SF_0181 | chr6: 146685878-146701196 | 13,883 | Y |
| chr1: 72317292-72328395 | NEGR1 | Dup | 230-3 | chr1: 72317292-72328395 | 10,621 | Y |
| chr1: 72317292-72328395 | NEGR1 | Dup | 230-4 | chr1: 72317292-72328395 | 10,621 | Y |
| chr1: 72317292-72328395 | NEGR1 | Dup | 230-5 | chr1: 72317292-72328395 | 10,621 | Y |
| chr1: 72317292-72328395 | NEGR1 | Dup | TD207.1 | chr1: 71648994-73025013 | 0 | Y |
| chr1: 72317292-72328395 | NEGR1 | Dup | M.Of.M.Cs.6308601 | chr1: 72322424-72328395 | 10,621 | Y |
| chr7: 153495598-153564827 | DPP6 | Dup | 332-3 | chr7: 153495598-153578582 | 54,698 | Y |
| chr7: 153495598-153564827 | DPP6 | Dup | 4079019863_A | chr7: 153495598-153564827 | 68,453 | Y |
| chr7: 153495598-153564827 | DPP6 | Dup | 4193372403_B | chr7: 153495598-153554210 | 79,070 | Y |
| chr7: 153495598-153564827 | DPP6 | Dup | 4243114113_R01C02 | chr7: 153495598-153577484 | 55,796 | Y |
| chr7: 153495598-153564827 | DPP6 | Dup | 1135 | chr7: 153495598-153576455 | 56,825 | N^ |
| chr7: 153495598-153564827 | DPP6 | Dup | 8201671744 | chr7: 153118878-153338318 | 0 | Y |
| chr7: 153495598-153564827 | DPP6 | Dup | W.Of.F.Cs.140002 | chr7: 153502896-153517548 | 115,317 | Y |
| chr7: 153495598-153564827 | DPP6 | Dup | W.Of.M.Cs.234002 | chr7: 153545279-153559377 | 73,903 | Y |

TABLE 17-continued

Boundaries of Individual CNVs in Table 1A and 1B.

| CNVR | Gene | Type | Sample ID | Region Called in Sample | Exon Distance* | Sample Validation Run |
|---|---|---|---|---|---|---|
| chr5: 65027976-65046520 | SGTB/NLN | Del | 067-3 | chr5: 65027976-65046520 | 0 | Y |
| chr5: 65027976-65046520 | SGTB/NLN | Del | 117-3 | chr5: 65027976-65046520 | 0 | Y |
| chr5: 65027976-65046520 | SGTB/NLN | Del | 152-3 | chr5: 65027976-65046520 | 0 | Y |
| chr5: 65027976-65046520 | SGTB/NLN | Del | 1670639198_A | chr5: 65027976-65046520 | 0 | Y |
| chr5: 65027976-65046520 | SGTB/NLN | Del | 15962 | chr5: 64483534-65101307 | 0 | Y |
| chr5: 65027976-65046520 | SGTB/NLN | Del | b11_SF_1055 | chr5: 65020291-65030503 | 3,236 | Y |
| chr1: 56053497-56064495 | USP24 | Del | 4147907208_B | chr1: 56053497-56064495 | 80,234 | Y |
| chr1: 56053497-56064495 | USP24 | Del | 393-3 | chr1: 56053497-56064495 | 80,234 | Y |
| chr1: 56053497-56064495 | USP24 | Del | 11411 | chr1: 56040939-56132401 | 67,676 | Y |
| chr1: 56053497-56064495 | USP24 | Del | 11804 | chr1: 56040939-56263366 | 67,676 | Y |
| chr1: 56053497-56064495 | USP24 | Del | 11727 | chr1: 56053497-56064840 | 80,234 | Y |
| chr1: 56053497-56064495 | USP24 | Del | b2_SF_0094 | chr1: 56051215-56057576 | 77,952 | Y |
| chr19: 38427720-38444834 | SLC7A10 | Del | 120-3 | chr19: 38415546-38444834 | 6,998 | Y |
| chr19: 38427720-38444834 | SLC7A10 | Del | 224-3 | chr19: 38415546-38444834 | 6,998 | Y |
| chr19: 38427720-38444834 | SLC7A10 | Del | 305-3 | chr19: 38415545-38434210 | 6,997 | Y |
| chr19: 38427720-38444834 | SLC7A10 | Del | 134-4 | chr19: 38418216-38444834 | 9,668 | Y |
| chr19: 38427720-38444834 | SLC7A10 | Del | 168-3 | chr19: 38423641-38444834 | 15,093 | Y |
| chr19: 38427720-38444834 | SLC7A10 | Del | 11931 | chr19: 38427721-38455315 | 19,173 | Y |
| chr19: 38427720-38444834 | SLC7A10 | Del | W.Of.F.Cs.121001 | chr19: 38423391-38442154 | 14,843 | Y |
| chr3: 1844168-1859889 | CNTN4 | Del | 078-3 | chr3: 1273990-1859889 | 0 | Y |
| chr3: 1844168-1859889 | CNTN4 | Del | 078-4 | chr3: 1273990-1859889 | 0 | Y |
| chr3: 1844168-1859889 | CNTN4 | Del | 141-3 | chr3: 1756625-1928413 | 187,137 | Y |
| chr3: 1844168-1859889 | CNTN4 | Del | 177-3 | chr3: 1844168-1936623 | 178,927 | Y |
| chr3: 1844168-1859889 | CNTN4 | Del | M.Of.F.Cs.53701 | chr3: 1793056-1956567 | 158,983 | Y |
| chr3: 1844168-1859889 | CNTN4 | Del | U.Of.F.Cs.852301 | chr3: 1835561-1852134 | 263,416 | Y |
| chr3: 1844168-1859889 | CNTN4 | Del | b3_SF_0253 | chr3: 1797102-1930071 | 185,479 | Y |
| chr2: 81419297-81446082 | CTNNA2 | Dup | 134-4 | chr2: 81035643-81654296 | 0 | Y |
| chr2: 81419297-81446082 | CTNNA2 | Dup | 144-3 | chr2: 81035643-81654296 | 0 | Y |
| chr2: 81419297-81446082 | CTNNA2 | Dup | 11484 | chr2: 81419297-81446082 | 152,417 | Y |
| chr2: 81419297-81446082 | CTNNA2 | Dup | b10_SF_0900 | chr2: 81352586-81386102 | 85,706 | Y |
| chr4: 113772340-113788584 | LARP7 | Dup | 303-3 | chr4: 113744172-113798058 | 0 | Y |
| chr4: 113772340-113788584 | LARP7 | Dup | 314-3 | chr4: 113744172-113798058 | 0 | Y |
| chr4: 113772340-113788584 | LARP7 | Dup | 17190 | chr4: 113772340-113788584 | 0 | Y |
| chr4: 113772340-113788584 | LARP7 | Dup | M.Fa.M.Cs.6300503 | chr4: 113769438-113801755 | 0 | Y |

*exon distance of '0' indicates that exon is impacted by the CNV
^sample not available for qPCR validation (sample visually validated in Bead Studio).

TABLE 18

Frequency of CNVs in GRM Receptor Interacting Genes in ADHD Cases and Controls.

| Gene | Del Counts (cases:controls) | Dup Counts (cases:controls) | ADHD Enrichment |
|---|---|---|---|
| ACAT1 | 0:0 | 1:0 | Yes |
| ACCN1 | 0:0 | 3:1 | Yes |
| ACTR2 | 1:0 | 0:1 | Yes |
| ADCY1 | 0:0 | 1:1 | Yes |
| ADRBK1 | 1:0 | 0:0 | Yes |
| ALDOA | 3:8 | 2:6 | Yes |
| APP | 0:0 | 8:2 | Yes |
| ARL15 | 1:1 | 2:0 | Yes |
| ATXN7L3 | 1:1 | 0:0 | Yes |
| BDKRB2 | 1:1 | 0:0 | Yes |
| CA8 | 0:0 | 1:0 | Yes |
| CACNA1B | 0:0 | 2:2 | Yes |
| CACYBP | 1:0 | 0:0 | Yes |
| CALM1 | 1:2 | 0:0 | Yes |
| CHRM3 | 0:0 | 2:1 | Yes |
| CIC | 1:1 | 0:0 | Yes |
| CNP | 1:2 | 0:0 | Yes |
| CRHR1 | 1:0 | 0:0 | Yes |
| DISC1 | 0:0 | 4:7 | Yes |
| DYNLL1 | 0:0 | 1:0 | Yes |
| FPR1 | 0:0 | 1:1 | Yes |
| GAPDH | 0:2 | 1:1 | Yes |
| GNA15 | 1:1 | 1:0 | Yes |
| GNAI2 | 2:4 | 0:0 | Yes |
| GNAO1 | 0:0 | 1:1 | Yes |
| GNAQ | 1:0 | 0:0 | Yes |
| GRIK1 | 0:0 | 8:2 | Yes |
| GRIK3 | 1:0 | 0:0 | Yes |
| GRM1 | 0:0 | 7:2 | Yes |
| GRM2 | 1:0 | 1:0 | Yes |
| GRM3 | 0:0 | 1:0 | Yes |
| GRM5 | 4:0 | 3:2 | Yes |
| GRM6 | 1:0 | 0:4 | Yes |
| GRM7 | 4:0 | 0:0 | Yes |
| GRM8 | 3:0 | 1:1 | Yes |
| GSN | 1:0 | 1:0 | Yes |
| HOMER1 | 0:0 | 1:0 | Yes |
| HTR2A | 0:0 | 1:0 | Yes |
| MAPK1 | 1:0 | 0:0 | Yes |
| MTHFD1 | 1:1 | 0:0 | Yes |
| MX1 | 0:0 | 7:2 | Yes |
| NARG1 | 1:0 | 0:0 | Yes |
| NMI | 0:0 | 1:0 | Yes |
| PCBP3 | 3:2 | 6:3 | Yes |
| PDE1C | 1:0 | 1:1 | Yes |
| PPP2R1A | 0:0 | 1:0 | Yes |
| PRPSAP1 | 0:0 | 1:1 | Yes |
| PSMD11 | 2:24 | 1:0 | Yes |
| PSMD13 | 0:4 | 1:2 | Yes |
| PXN | 0:0 | 1:0 | Yes |
| QRICH2 | 1:1 | 0:1 | Yes |
| RANBP1 | 2:3 | 0:9 | Yes |

TABLE 18-continued

Frequency of CNVs in GRM Receptor Interacting Genes in ADHD Cases and Controls.

| Gene | Del Counts (cases:controls) | Dup Counts (cases:controls) | ADHD Enrichment |
|---|---|---|---|
| RAP2A | 0:0 | 1:1 | Yes |
| RCC1 | 0:0 | 1:0 | Yes |
| RGS12 | 2:0 | 0:0 | Yes |
| RIF1 | 0:0 | 1:0 | Yes |
| RUVBL2 | 1:0 | 0:3 | Yes |
| RYR1 | 1:2 | 1:1 | Yes |
| RYR2 | 1:0 | 1:0 | Yes |
| SDC3 | 1:0 | 0:1 | Yes |
| SELE | 1:0 | 0:0 | Yes |
| SERPINB9 | 0:0 | 1:0 | Yes |
| SETD4 | 2:0 | 8:3 | Yes |
| SHANK1 | 0:0 | 1:0 | Yes |
| SORD | 0:0 | 1:0 | Yes |
| STRAP | 0:0 | 1:1 | Yes |
| TK1 | 2:0 | 0:2 | Yes |
| TNIK | 1:0 | 0:0 | Yes |
| VHL | 0:0 | 1:0 | Yes |
| BTBD2 | 0:7 | 1:15 | No |
| ECHS1 | 0:1 | 1:22 | No |
| F2RL3 | 1:16 | 0:0 | No |
| GNB2L1 | 0:0 | 0:4 | No |
| HOMER3 | 1:12 | 1:9 | No |
| ITGB7 | 0:5 | 1:12 | No |
| KIAA1683 | 3:18 | 0:3 | No |
| PDE6G | 3:26 | 1:12 | No |
| PLCB3 | 0:5 | 0:2 | No |
| PYGM | 3:29 | 0:4 | No |
| RPLP2 | 8:92 | 1:6 | No |
| SLC6A3 | 0:0 | 0:11 | No |
| SRC | 1:19 | 0:2 | No |
| TBCA | 1:10 | 0:0 | No |
| TRAF2 | 5:24 | 1:11 | No |
| 40425 | 0:0 | 0:0 | NoSNPsOnGene |
| ADRA2A | 0:0 | 0:0 | NoSNPsOnGene |
| ADRA2C | 1:1 | 0:1 | NoSNPsOnGene |
| C17orf44 | 0:0 | 0:0 | NoSNPsOnGene |
| C7orf25 | 0:0 | 0:0 | NoSNPsOnGene |
| F2RL2 | 0:3 | 0:0 | NoSNPsOnGene |
| FKBP3 | 0:0 | 0:0 | NoSNPsOnGene |
| FSCN1 | 0:0 | 0:1 | NoSNPsOnGene |
| GRB7 | 0:0 | 0:0 | NoSNPsOnGene |
| HSP90AB1 | 1:0 | 0:0 | NoSNPsOnGene |
| IMPDH2 | 0:0 | 0:0 | NoSNPsOnGene |
| LOC642393 | 0:0 | 1:4 | NoSNPsOnGene |
| LOC653098 | 0:0 | 0:0 | NoSNPsOnGene |
| MC4R | 0:0 | 0:0 | NoSNPsOnGene |
| MGC11082 | 0:0 | 0:0 | NoSNPsOnGene |
| MRPS16 | 0:0 | 0:0 | NoSNPsOnGene |
| NPY2R | 1:0 | 0:0 | NoSNPsOnGene |
| PAFAH1B3 | 1:1 | 0:0 | NoSNPsOnGene |
| PCBP1 | 0:0 | 0:0 | NoSNPsOnGene |
| PCMT1 | 0:0 | 0:0 | NoSNPsOnGene |
| PHKG2 | 0:0 | 0:0 | NoSNPsOnGene |
| PRLHR | 0:0 | 0:0 | NoSNPsOnGene |
| PSME1 | 0:0 | 0:0 | NoSNPsOnGene |
| RAB2 | 2:2 | 0:1 | NoSNPsOnGene |
| RGS2 | 0:0 | 0:0 | NoSNPsOnGene |
| S100A6 | 0:0 | 0:0 | NoSNPsOnGene |
| SET | 0:0 | 0:0 | NoSNPsOnGene |
| SF3B14 | 0:0 | 0:0 | NoSNPsOnGene |
| TBXA2R | 10:44 | 0:10 | NoSNPsOnGene |
| TMEM4 | 0:0 | 0:0 | NoSNPsOnGene |
| TPI1 | 0:0 | 1:1 | NoSNPsOnGene |
| TRMT112 | 0:1 | 0:2 | NoSNPsOnGene |
| TUBA1 | 0:0 | 0:0 | NoSNPsOnGene |
| TUBA1A | 0:0 | 0:0 | NoSNPsOnGene |
| TUBA2 | 0:1 | 0:0 | NoSNPsOnGene |
| TUBB | 0:0 | 0:0 | NoSNPsOnGene |
| TUBG1 | 0:1 | 0:0 | NoSNPsOnGene |
| ACAT2 | 0:0 | 0:0 | |
| ACCN2 | 0:2 | 0:0 | |
| ACP1 | 0:0 | 0:3 | |
| ACTB | 0:0 | 0:0 | |
| ADA | 0:0 | 0:0 | |
| ADD1 | 0:0 | 0:0 | |
| ADD2 | 0:0 | 0:0 | |
| ADORA1 | 0:0 | 0:1 | |
| ADRA1B | 0:0 | 0:0 | |
| ADRB2 | 0:0 | 0:0 | |
| ANXA2 | 0:0 | 0:0 | |
| APTX | 0:0 | 0:0 | |
| AQP1 | 0:0 | 0:1 | |
| ARHGAP24 | 0:0 | 0:0 | |
| ARRB1 | 0:0 | 0:0 | |
| ARRB2 | 0:0 | 0:1 | |
| BDKRB1 | 0:0 | 0:0 | |
| BTG2 | 0:0 | 0:1 | |
| C1orf116 | 0:0 | 0:1 | |
| CALB2 | 0:0 | 0:0 | |
| CALM2 | 0:0 | 0:0 | |
| CALM3 | 0:0 | 0:0 | |
| CAMK1 | 0:0 | 0:0 | |
| CAMK2B | 0:0 | 0:0 | |
| CAMK4 | 0:0 | 0:0 | |
| CCNB1 | 0:0 | 0:0 | |
| CDC42 | 0:0 | 0:0 | |
| CENTG1 | 0:1 | 0:0 | |
| CHGB | 0:0 | 0:0 | |
| CHP | 0:0 | 0:0 | |
| CHRM2 | 0:0 | 0:0 | |
| CMPK | 0:0 | 0:0 | |
| CNR1 | 0:0 | 3:8 | |
| COPB2 | 0:0 | 0:0 | |
| CYCS | 0:0 | 0:0 | |
| DCN | 0:0 | 0:0 | |
| DHCR7 | 0:0 | 0:1 | |
| DLST | 0:0 | 0:0 | |
| DRD2 | 0:0 | 0:0 | |
| DRD3 | 0:0 | 0:0 | |
| DSTN | 0:0 | 0:0 | |
| EGFR | 0:0 | 0:0 | |
| EIF3S3 | 0:0 | 0:1 | |
| ERBB2 | 0:0 | 0:0 | |
| F2R | 0:0 | 0:0 | |
| F3 | 0:0 | 0:0 | |
| FURIN | 0:0 | 0:0 | |
| FYN | 0:0 | 0:0 | |
| GLP1R | 0:0 | 0:0 | |
| GLP2R | 0:0 | 0:0 | |
| GNAI1 | 0:0 | 0:0 | |
| GNAI3 | 0:0 | 0:0 | |
| GOT1 | 0:0 | 0:0 | |
| GP1BA | 0:0 | 0:0 | |
| GPR26 | 0:0 | 0:0 | |
| GRB2 | 0:0 | 0:0 | |
| GRIA1 | 0:0 | 0:0 | |
| GRM4 | 0:0 | 0:0 | |
| HBXIP | 0:0 | 0:0 | |
| HD | 0:0 | 0:0 | |
| HNRPA3 | 0:0 | 0:0 | |
| IL8RB | 0:0 | 0:0 | |
| IQGAP2 | 0:0 | 0:0 | |
| ITGB1 | 0:0 | 0:0 | |
| ITPR1 | 0:0 | 0:0 | |
| KIAA0090 | 0:1 | 0:0 | |
| LAMA4 | 0:0 | 0:0 | |
| LRP2BP | 0:3 | 0:0 | |
| LRRC59 | 0:0 | 0:0 | |
| LTA | 0:0 | 0:0 | |
| LYAR | 0:0 | 0:0 | |
| LYN | 1:3 | 0:0 | |
| MAP4 | 0:0 | 0:0 | |
| MAPT | 0:0 | 0:0 | |
| MARK4 | 0:0 | 0:0 | |
| MRPL14 | 0:0 | 0:0 | |
| MTNR1A | 0:3 | 0:0 | |
| MTNR1B | 0:0 | 0:0 | |
| MYC | 0:1 | 0:0 | |

TABLE 18-continued

Frequency of CNVs in GRM Receptor Interacting Genes in ADHD Cases and Controls.

| Gene | Del Counts (cases:controls) | Dup Counts (cases:controls) | ADHD Enrichment |
|---|---|---|---|
| MYO6 | 0:0 | 0:0 | |
| NANS | 0:0 | 0:0 | |
| NCK1 | 0:0 | 0:0 | |
| NFKBIA | 0:0 | 0:0 | |
| NUDC | 0:0 | 0:1 | |
| OPRD1 | 3:13 | 0:0 | |
| PCDHA4 | 0:0 | 0:0 | |
| PCID1 | 0:0 | 0:0 | |
| PDCD5 | 0:0 | 0:0 | |
| PDE1B | 0:0 | 0:0 | |
| PGM1 | 0:0 | 0:0 | |
| PHKB | 0:0 | 0:0 | |
| PICK1 | 0:3 | 0:1 | |
| PIK3CA | 0:0 | 0:0 | |
| PIK3R1 | 0:0 | 0:0 | |
| PLA2G7 | 0:0 | 0:0 | |
| PLCB1 | 0:0 | 0:0 | |
| PLCG2 | 0:0 | 0:0 | |
| PPIH | 0:0 | 0:0 | |
| PRDX1 | 0:0 | 0:0 | |
| PRKCA | 0:0 | 0:0 | |
| PRMT1 | 0:0 | 0:1 | |
| PSAT1 | 0:0 | 0:0 | |
| PSEN1 | 0:0 | 0:0 | |
| PSMA1 | 0:0 | 0:1 | |
| PSMC1 | 0:0 | 0:0 | |
| PSMD1 | 0:0 | 0:0 | |
| PSMD6 | 0:0 | 0:0 | |
| PTHR2 | 0:0 | 0:0 | |
| PYGL | 0:0 | 0:0 | |
| RALA | 0:0 | 0:0 | |
| RCC2 | 0:0 | 0:0 | |
| RHOA | 0:0 | 0:0 | |
| RPA2 | 0:0 | 0:0 | |
| RPN2 | 0:0 | 0:0 | |
| RPS14 | 0:0 | 0:0 | |
| RRM1 | 0:0 | 0:0 | |
| SACS | 0:0 | 0:1 | |
| SARS | 0:0 | 0:0 | |
| SCTR | 0:0 | 0:0 | |
| SHBG | 0:0 | 0:0 | |
| SIAH1 | 0:0 | 0:0 | |
| SLC2A1 | 0:0 | 0:0 | |
| SNCA | 0:0 | 0:0 | |
| SNRPB2 | 0:0 | 0:0 | |
| SOCS6 | 0:0 | 0:0 | |
| SOCS7 | 0:0 | 0:0 | |
| STAU1 | 0:0 | 0:0 | |
| STX12 | 0:0 | 0:0 | |
| SYK | 0:0 | 0:0 | |
| TCP1 | 0:0 | 0:0 | |
| TEAD3 | 0:0 | 0:0 | |
| TFAM | 0:0 | 0:0 | |
| TGM2 | 0:0 | 0:3 | |
| TJP1 | 0:0 | 0:2 | |
| TLR10 | 0:0 | 0:0 | |
| TUBA1B | 0:0 | 0:0 | |
| TXN | 0:0 | 0:0 | |
| TXNDC4 | 0:2 | 0:1 | |
| TXNL2 | 0:0 | 0:1 | |
| TYMS | 0:0 | 0:2 | |
| UBQLN4 | 0:0 | 0:0 | |
| UCHL1 | 0:0 | 0:0 | |
| VIPR1 | 0:0 | 0:0 | |
| YWHAQ | 0:0 | 0:0 | |
| ZAP70 | 0:0 | 0:0 | |

TABLE 19

Gene clusters based on the network of interacting genes

| Cluster # | Genes |
|---|---|
| 1 | SET, HNRPA3, RRM1, SORD, PSMC1, MTHFD1, CACYBP, PCBP1, TXNL2, 40425, SARS, PCID1, GSN, PSMD6, TBCA, MRPS16, RCC2, COPB2, RANBP1, PRMT1, ANXA2, FSCN1, RCC1, ACAT1, NUDC, EIF3S3, UCHL1, FKBP3, PDCD5, ACTR2, PSAT1, LYAR, PCBP3, SF3B14, LRRC59, ACP1, ACAT2, RUVBL2, GPR26, MAPK1, CYCS, MGC11082, STRAP, RAP2A, IMPDH2, ACTR2, PSMD1, SETD4, TRMT112, CMPK, MRPL14, SNRPB2, TEAD3, TMEM4, TFAM, DSTN, PRPSAP1, KIAA0090, PPIH, PSMA1, RPS14, DHCR7, PSMD13, TRAF2, TNIK, RPN2, TYMS, NCK1, NANS, NARG1, PPP2R1A, ECHS1, GOT1, PCMT1 |
| 2 | GRB7, PYGL, CRHR1, PDE1C, CALM1, GLP1R, PYGM, PHKG2, PTHR2, PDE1B, GLP2R, ADD2, ADCY1, SCTR, PHKB, VIPR1, ADD1, PGM1, PGM1, IQGAP2 |
| 3 | HBXIP, S100A6, TXN, SLC2A1, CAMK1, RAB2, PCDHA4, QRICH2, GAPDH, BTBD2, PAFAH1B3, SERPINB9, PSMD11, PRDX1, RPA2, CAMK2B, LAMA4, ARL15, TPI1, CAMK4, TK1, FYN, PGM1, ACTB, CHP |
| 4 | SLC6A3, UBQLN4, PRLHR, PICK1, CIC, APTX, ERBB2, ATXN7L3, ACCN2, AQP1, GRIA1, ACCN1, ECHS1, SACS, BTG2, LRP2BP, PRKCA |
| 5 | RALA, CDC42, DRD3, ITGB1, ITGB7, TLR10, HSP90AB1, TJP1, FURIN, VHL, MTNR1B, PSEN1, SHBG, DCN, F3, GRIK3, GP1BA, RHOA, SELE, DRD2, ARHGAP24, MTNR1A, FKBP3, ARRB2, GRM8 |
| 6 | NPY2R, RGS12, GNAI3, ADRA2C, GNAI2, GNAO1, CACNA1B, GNAI1, GRM6, IL8RB, PLCB3 |
| 7 | ADRA2A, PDE6G, SRC, MC4R, ARRB1, SNCA, RPLP2, FPR1, BDKRB2, ADRBK1, OPRD1 |
| 8 | PLCB1, TXNDC4, ITPR1, CCNB1, LYN, CA8, PLCG2 |
| 9 | F2RL3, HTR2A, ADRA1B, F2R, RGS2, HTR2A, GNAQ, F2RL2, CHRM3, PIK3CA, BDKRB2, TBXA2R, BDKRB1 |
| 10 | GNB2L1, CNP, STAU1, CHGB, PSME1, SOCS7, DLST, ALDOA, SYK, SDC3, TUBB, TGM2, HD, MARK4, MAP4, MX1, TUBA1A, SOCS6, C7orf25, PLA2G7 |
| 11 | HOMER1, STX12, CENTG1, RYR2, LOC653098, HOMER3, C1orf116, SHANK1, RYR1 |
| 12 | CNR1, GNA15, CHRM2, ADRB2 |

TABLE 19-continued

Gene clusters based on the network of interacting genes

| Cluster # | Genes |
|---|---|
| 13 | DYNLL1, PIK3R1, NMI, TUBA2, PXN, TUBG1, NFKBIA, TUBA1B, YWHAQ |
| 14 | HRPT2, RIF1, GRM3 |
| 15 | CALM3, GRM5, MYO6, KIAA1683, GRM7, LOC642393, C17orf44, CALM2 |
| 16 | CALB2, TCP1, LTA, TUBA1, ZAP70 |
| 17 | ADA, ADORA1 |

Additional analyses were preformed using an Agilent comparative genomic hybridization (CGH) array. The mGluR network genes are defined by both forward and reverse protein protein interactions using experimental data derived from a variety of experimental protocols including yeast 2 hybrid assays and mass spectrometry. The merged human interactome combines human interactions reported in IntAct, DIP, BIND and HPRD, in addition to papers by Rual et al. Nature 437, 1173-1178 (2005); Stelzl et al. Cell 122, 957-968 (2005); Ramani et al. Genome Biol. 2005; 6(5): R40. Epub 2005 Apr. 15; Venkatesan Nat. Methods 6, 83-90 (2009); and Yu et al. Nat. Methods 8, 478-480 (2011).

The original forward entries only considers GRM as the "source" of and gives other genes which are "targets" i.e. "GRM pp X" and "X pp Y" (where pp is protein protein interaction). Forward and reverse includes GRM as both the "source" and the "target" of a biological signal i.e. "GRM pp X", "X pp GRM", "X pp Y", and "Y pp X".

An Agilent comparative genomic hybridization (CGH) array with 173,997 genomic probes was created to capture the GRM gene network. Agilent SurePrint G3 Custom CGH Microarrays Custom 4×180K were used to assay 150 ADHD subjects. The protocol version was named "CGH_1100_Jul11" released Jul. 1, 2011. CNVs were called using Agilent Cytogenomics software. CNVs overlapping ADHD GRM network genes were extracted from the CNV calls. Many of these genes have already been listed in the tables above. 276 GRM network genes were listed previously based on forward interactions. We now have 868 GRM network genes. The previous CNV observation counts were based on Illumina 550k SNP microarray data. The data presented in Tables 20, 21 and 22 is based on Agilent CGH data.

| CNVCall(hg19) | Num Probes | Length | CN | SampleID | GRMNetworkGenes |
|---|---|---|---|---|---|
| chr10: 54016076-54018132 | 8 | 2056 | 3 | 540043624 | PRKG1 |
| chr10: 54015519-54018132 | 10 | 2613 | 3 | 634992689 | PRKG1 |
| chr12: 14094648-14095317 | 4 | 669 | 3 | 634992689 | GRIN2B |
| chr19: 3153225-3154967 | 3 | 1742 | 3 | 634992689 | GNA15 |
| chr10: 53203699-53211914 | 28 | 8215 | 1 | 706896538 | PRKG1 |
| chr3: 7400107-7401986 | 7 | 1879 | 1 | 706896538 | GRM7 |
| chr15: 67868548-67869255 | 4 | 707 | 1 | 706896538 | MAP2K5 |
| chr15: 45318599-45323810 | 14 | 5211 | 1 | 777193129 | SORD |
| chr10: 54015852-54017933 | 8 | 2081 | 1 | 1386063997 | PRKG1 |
| chr3: 7400107-7401986 | 7 | 1879 | 1 | 1386063997 | GRM7 |
| chr11: 108012158-108019887 | 24 | 7729 | 3 | 1449077767 | ACAT1 |
| chr10: 54016509-54018132 | 7 | 1623 | 1 | 1758814067 | PRKG1 |
| chr5: 159349807-159351427 | 6 | 1620 | 1 | 1758814067 | ADRA1B |
| chrX: 66761119-153603660 | 3596 | 86842541 | 3 | 1758814067 | AR EFNB1 DLG3 GJB1 PHKA1 PGK1 TSPAN6 BTK IRS4 HTR2C GRIA3 CNGA2 BCAP31 IRAK1 FLNA |
| chrX: 5805129-49057162 | 1965 | 43252033 | 3 | 1758814067 | TMSB4X PPEF1 PHKA2 CNKSR2 SAT1 XK HDAC6 PQBP1 |
| chrX: 7201364-43706264 | 678 | 36504900 | 3 | 1758814067 | TMSB4X PPEF1 PHKA2 CNKSR2 SAT1 XK |
| chrX: 152800026-153601624 | 419 | 801598 | 3 | 1758814067 | BCAP31 IRAK1 FLNA |
| chrX: 113819324-147033026 | 1925 | 33213702 | 3 | 1758814067 | HTR2C GRIA3 |
| chrX: 152841848-153361084 | 198 | 519236 | 3 | 1758814067 | BCAP31 IRAK1 |
| chrX: 153581560-153597649 | 47 | 16089 | 3 | 1758814067 | FLNA |
| chr10: 54015852-54018132 | 9 | 2280 | 1 | 1875095658 | PRKG1 |
| chrX: 66761119-153580971 | 3530 | 86819852 | 1 | 1909944985 | AR EFNB1 DLG3 GJB1 PHKA1 PGK1 TSPAN6 BTK IRS4 HTR2C GRIA3 CNGA2 BCAP31 IRAK1 FLNA |
| chrX: 5805129-49052017 | 1949 | 43246888 | 1 | 1909944985 | TMSB4X PPEF1 PHKA2 CNKSR2 SAT1 XK HDAC6 PQBP1 |

-continued

| CNVCall(hg19) | Num Probes | Length | CN | SampleID | GRMNetworkGenes |
|---|---|---|---|---|---|
| chrX: 70364402-113819143 | 95 | 43454741 | 1 | 1909944985 | GJB1 PHKA1 PGK1 TSPAN6 BTK IRS4 HTR2C |
| chrX: 7255863-43740570 | 634 | 36484707 | 1 | 1909944985 | TMSB4X PPEF1 PHKA2 CNKSR2 SAT1 XK |
| chrX: 113825958-151427216 | 2208 | 37601258 | 1 | 1909944985 | HTR2C GRIA3 CNGA2 |
| chrX: 43740963-49049852 | 30 | 5308889 | 1 | 1909944985 | HDAC6 PQBP1 |
| chrX: 153294925-153580753 | 193 | 285828 | 1 | 1909944985 | FLNA |
| chrX: 153582356-153603660 | 59 | 21304 | 1 | 1909944985 | FLNA |
| chr10: 54015852-54018132 | 9 | 2280 | 1 | 1909944985 | PRKG1 |
| chr21: 31136298-31138914 | 9 | 2616 | 1 | 2087655441 | GRIK1 |
| chr10: 54015852-54018132 | 9 | 2280 | 1 | 2087655441 | PRKG1 |
| chr4: 86705101-86707016 | 8 | 1915 | 1 | 2087655441 | ARHGAP24 |
| chr20: 8410187-8410935 | 3 | 748 | 1 | 2087655441 | PLCB1 |
| chr10: 54016076-54018132 | 8 | 2056 | 0 | 2263247074 | PRKG1 |
| chr10: 54016076-54018132 | 8 | 2056 | 3 | 2480284985 | PRKG1 |
| chr10: 53203699-53211914 | 28 | 8215 | 1 | 2506463349 | PRKG1 |
| chr19: 51196003-51197183 | 6 | 1180 | 1 | 2506463349 | SHANK1 |
| chr10: 54016076-54017933 | 7 | 1857 | 3 | 2745704925 | PRKG1 |
| chr1: 237961127-239798000 | 111 | 1836873 | 1 | 2783498413 | RYR2 CHRM3 |
| chr10: 53203699-53211736 | 27 | 8037 | 1 | 2783498413 | PRKG1 |
| chr13: 98103980-98107960 | 13 | 3980 | 1 | 2783498413 | RAP2A |
| chr14: 64886906-64887666 | 3 | 760 | 4 | 2783498413 | MTHFD1 |
| chr3: 7634038-7634315 | 3 | 277 | 4 | 2783498413 | GRM7 |
| chr1: 237800047-237800335 | 3 | 288 | 4 | 2783498413 | RYR2 |
| chr10: 54016076-54018451 | 9 | 2375 | 3 | 2788109451 | PRKG1 |
| chr13: 98103980-98107960 | 13 | 3980 | 1 | 3011405439 | RAP2A |
| chr15: 67868548-67869255 | 4 | 707 | 1 | 3011405439 | MAP2K5 |
| chr15: 45317893-45323810 | 17 | 5917 | 3 | 3011405439 | SORD |
| chr20: 10233322-10233792 | 3 | 470 | 3 | 3011405439 | SNAP25 |
| chr3: 7634038-7634315 | 3 | 277 | 3 | 3011405439 | GRM7 |
| chr14: 64886906-64887666 | 3 | 760 | 3 | 3011405439 | MTHFD1 |
| chr19: 3153225-3154967 | 3 | 1742 | 3 | 3011405439 | GNA15 |
| chr1: 237800047-237800335 | 3 | 288 | 3 | 3011405439 | RYR2 |
| chr10: 54016076-54018132 | 8 | 2056 | 1 | 3067349136 | PRKG1 |
| chr3: 7400107-7401986 | 7 | 1879 | 1 | 3067349136 | GRM7 |
| chr10: 54015852-54018132 | 9 | 2280 | 1 | 3362075486 | PRKG1 |
| chr3: 7400950-7401986 | 5 | 1036 | 1 | 3362075486 | GRM7 |
| chrX: 66761119-153603660 | 3595 | 86842541 | 3 | 3422467772 | AR EFNB1 DLG3 GJB1 PHKA1 PGK1 TSPAN6 BTK IRS4 HTR2C GRIA3 CNGA2 BCAP31 IRAK1 FLNA |
| chrX: 5805129-49057162 | 1966 | 43252033 | 3 | 3422467772 | TMSB4X PPEF1 PHKA2 CNKSR2 SAT1 XK HDAC6 PQBP1 |
| chrX: 7200554-43651291 | 526 | 36450737 | 3 | 3422467772 | TMSB4X PPEF1 PHKA2 CNKSR2 SAT1 XK |
| chrX: 115569223-147027070 | 1096 | 31457847 | 3 | 3422467772 | GRIA3 |
| chrX: 153361694-153601429 | 80 | 239735 | 3 | 3422467772 | FLNA |
| chr10: 54015519-54018451 | 11 | 2932 | 3 | 3422467772 | PRKG1 |
| chr1: 237800047-237800335 | 3 | 288 | 3 | 3422467772 | RYR2 |
| chr14: 73689858-73690133 | 3 | 275 | 3 | 3422467772 | PSEN1 |
| chrX: 66761119-153581425 | 3530 | 86820306 | 3 | 3517579824 | AR EFNB1 DLG3 GJB1 PHKA1 PGK1 TSPAN6 BTK IRS4 HTR2C GRIA3 CNGA2 BCAP31 IRAK1 FLNA |
| chrX: 5805129-49057162 | 1963 | 43252033 | 3 | 3517579824 | TMSB4X PPEF1 PHKA2 CNKSR2 SAT1 XK HDAC6 PQBP1 |
| chrX: 7249057-43702934 | 537 | 36453877 | 3 | 3517579824 | TMSB4X PPEF1 PHKA2 CNKSR2 SAT1 XK |
| chrX: 113819324-151394125 | 2162 | 37574801 | 3 | 3517579824 | HTR2C GRIA3 CNGA2 |
| chrX: 153582115-153603660 | 60 | 21545 | 3 | 3517579824 | FLNA |
| chr3: 7400950-7401986 | 5 | 1036 | 1 | 3699727928 | GRM7 |
| chr10: 54016076-54018132 | 8 | 2056 | 3 | 3699727928 | PRKG1 |
| chr10: 53203699-53211914 | 28 | 8215 | 1 | 3798219453 | PRKG1 |

-continued

| CNVCall(hg19) | Num Probes | Length | CN | SampleID | GRMNetworkGenes |
|---|---|---|---|---|---|
| chr13: 98103980-98108313 | 14 | 4333 | 1 | 3798219453 | RAP2A |
| chrX: 66761119-153580971 | 3533 | 86819852 | 3 | 3798219453 | AR EFNB1 DLG3 GJB1 PHKA1 PGK1 TSPAN6 BTK IRS4 HTR2C GRIA3 CNGA2 BCAP31 IRAK1 FLNA |
| chrX: 66944242-113819143 | 107 | 46874901 | 3 | 3798219453 | EFNB1 DLG3 GJB1 PHKA1 PGK1 TSPAN6 BTK IRS4 HTR2C |
| chrX: 5805129-49057162 | 1965 | 43252033 | 3 | 3798219453 | TMSB4X PPEF1 PHKA2 CNKSR2 SAT1 XK HDAC6 PQBP1 |
| chrX: 113848523-146991850 | 1723 | 33143327 | 3 | 3798219453 | HTR2C GRIA3 |
| chrX: 153582356-153603660 | 59 | 21304 | 3 | 3798219453 | FLNA |
| chr10: 54015852-54018132 | 9 | 2280 | 3 | 3798219453 | PRKG1 |
| chr14: 73689858-73690133 | 3 | 275 | 3 | 3798219453 | PSEN1 |
| chr14: 64886906-64887666 | 3 | 760 | 3 | 3798219453 | MTHFD1 |
| chr1: 237800047-237800335 | 3 | 288 | 3 | 3798219453 | RYR2 |
| chr13: 98103980-98108313 | 14 | 4333 | 3 | 3870877985 | RAP2A |
| chr10: 54015852-54017933 | 8 | 2081 | 1 | 3870877985 | PRKG1 |
| chr3: 171042118-171043337 | 3 | 1219 | 0 | 3912314851 | TNIK |
| chr12: 7348541-8089521 | 47 | 740980 | 3 | 3912314851 | CD163 |
| chr15: 67879375-67888404 | 29 | 9029 | 3 | 3912314851 | MAP2K5 |
| chr3: 7634038-7634315 | 3 | 277 | 3 | 3912314851 | GRM7 |
| chr1: 237800047-237800335 | 3 | 288 | 3 | 3912314851 | RYR2 |
| chr10: 54015852-54018132 | 9 | 2280 | 1 | 4094894821 | PRKG1 |
| chr13: 98103980-98108313 | 14 | 4333 | 1 | 4186136103 | RAP2A |
| chr10: 54015852-54017428 | 6 | 1576 | 3 | 4186136103 | PRKG1 |
| chrX: 66761119-153603660 | 3594 | 86842541 | 3 | 4312916573 | AR EFNB1 DLG3 GJB1 PHKA1 PGK1 TSPAN6 BTK IRS4 HTR2C GRIA3 CNGA2 BCAP31 IRAK1 FLNA |
| chrX: 5805129-49057162 | 1963 | 43252033 | 3 | 4312916573 | TMSB4X PPEF1 PHKA2 CNKSR2 SAT1 XK HDAC6 PQBP1 |
| chrX: 113819324-151381971 | 2136 | 37562647 | 3 | 4312916573 | HTR2C GRIA3 CNGA2 |
| chrX: 152800026-153601624 | 418 | 801598 | 3 | 4312916573 | BCAP31 IRAK1 FLNA |
| chrX: 152844142-153580971 | 217 | 736829 | 3 | 4312916573 | BCAP31 IRAK1 FLNA |
| chrX: 153581833-153597649 | 45 | 15816 | 3 | 4312916573 | FLNA |
| chr10: 54016076-54018132 | 8 | 2056 | 3 | 4312916573 | PRKG1 |
| chr10: 54016076-54018132 | 8 | 2056 | 0 | 4568504054 | PRKG1 |
| chr21: 31136298-31138914 | 9 | 2616 | 1 | 4568504054 | GRIK1 |
| chr13: 23970623-23971130 | 3 | 507 | 1 | 4879516384 | SACS |
| chr15: 67868782-67869255 | 3 | 473 | 0 | 5019244906 | MAP2K5 |
| chr21: 31136298-31138914 | 9 | 2616 | 1 | 5019244906 | GRIK1 |
| chr19: 51196003-51197569 | 8 | 1566 | 1 | 5019244906 | SHANK1 |
| chr10: 53203699-53211914 | 28 | 8215 | 1 | 5249007609 | PRKG1 |
| chr13: 98103980-98108313 | 14 | 4333 | 1 | 5249007609 | RAP2A |
| chr10: 54016076-54018132 | 8 | 2056 | 1 | 5249007609 | PRKG1 |
| chr6: 152390044-152392065 | 7 | 2021 | 1 | 5249007609 | ESR1 |
| chr3: 7400950-7401986 | 5 | 1036 | 1 | 5249007609 | GRM7 |
| chr12: 14094648-14094993 | 3 | 345 | 3 | 5249007609 | GRIN2B |
| chr14: 73689858-73690133 | 3 | 275 | 3 | 5249007609 | PSEN1 |
| chr1: 237800047-237800335 | 3 | 288 | 3 | 5249007609 | RYR2 |
| chr10: 54016076-54018132 | 8 | 2056 | 3 | 5504576456 | PRKG1 |
| chr10: 54015852-54018132 | 9 | 2280 | 3 | 6512183041 | PRKG1 |
| chr10: 54015852-54018132 | 9 | 2280 | 1 | 6631887946 | PRKG1 |
| chr12: 7348541-8089521 | 47 | 740980 | 3 | 6631887946 | CD163 |
| chrX: 66796137-66821227 | 73 | 25090 | 0 | 6815706198 | AR |
| chrX: 66761543-153603332 | 3588 | 86841789 | 1 | 6815706198 | AR EFNB1 DLG3 GJB1 PHKA1 PGK1 TSPAN6 BTK IRS4 HTR2C GRIA3 CNGA2 BCAP31 IRAK1 FLNA |

-continued

| CNVCall(hg19) | Num Probes | Length | CN | SampleID | GRMNetworkGenes |
|---|---|---|---|---|---|
| chrX: 5805129-49051018 | 1949 | 43245889 | 1 | 6815706198 | TMSB4X PPEF1 PHKA2 CNKSR2 SAT1 XK HDAC6 PQBP1 |
| chrX: 7244669-43572092 | 236 | 36327423 | 1 | 6815706198 | TMSB4X PPEF1 PHKA2 CNKSR2 SAT1 XK |
| chrX: 151615620-153601624 | 438 | 1986004 | 1 | 6815706198 | BCAP31 IRAK1 FLNA |
| chrX: 113824488-122325013 | 906 | 8500525 | 1 | 6815706198 | HTR2C GRIA3 |
| chrX: 152844958-153298046 | 31 | 453088 | 1 | 6815706198 | BCAP31 IRAK1 |
| chrX: 146994463-151118845 | 123 | 4124382 | 1 | 6815706198 | CNGA2 |
| chrX: 153338815-153580971 | 82 | 242156 | 1 | 6815706198 | FLNA |
| chr5: 159349807-159351164 | 5 | 1357 | 1 | 6815706198 | ADRA1B |
| chr3: 47985150-47987833 | 7 | 2683 | 1 | 6874498376 | MAP4 |
| chr10: 54016076-54018132 | 8 | 2056 | 0 | 6916433107 | PRKG1 |
| chr11: 88253885-88257180 | 12 | 3295 | 1 | 6916433107 | GRM5 |
| chr3: 7400107-7401986 | 7 | 1879 | 1 | 6916433107 | GRM7 |
| chr10: 54016076-54017933 | 7 | 1857 | 1 | 7315108852 | PRKG1 |
| chr7: 126514925-126529917 | 17 | 14992 | 1 | 7315108852 | GRM8 |
| chr3: 171042118-171043337 | 3 | 1219 | 0 | 7318361083 | TNIK |
| chr15: 67878138-67888404 | 33 | 10266 | 3 | 7318361083 | MAP2K5 |
| chr12: 14094648-14094993 | 3 | 345 | 3 | 7322778785 | GRIN2B |
| chr15: 67878764-67888404 | 31 | 9640 | 3 | 7415787021 | MAP2K5 |
| chr10: 54015852-54017650 | 7 | 1798 | 3 | 7415787021 | PRKG1 |
| chr6: 150083379-150085073 | 4 | 1694 | 3 | 7415787021 | PCMT1 |
| chr1: 237800047-237800335 | 3 | 288 | 4 | 7415787021 | RYR2 |
| chr19: 51196003-51197390 | 7 | 1387 | 1 | 8115359545 | SHANK1 |
| chr10: 54016076-54018132 | 8 | 2056 | 3 | 8115359545 | PRKG1 |
| chr10: 54015852-54018132 | 9 | 2280 | 3 | 8344392353 | PRKG1 |
| chr10: 54016509-54018132 | 7 | 1623 | 1 | 8574874421 | PRKG1 |
| chr1: 237799565-237800335 | 4 | 770 | 3 | 8574874421 | RYR2 |
| chr7: 126514925-126523697 | 13 | 8772 | 3 | 8594759249 | GRM8 |
| chr15: 67868548-67869255 | 4 | 707 | 0 | 8783639811 | MAP2K5 |
| chrX: 66761543-153603660 | 3594 | 86842117 | 1 | 8783639811 | AR EFNB1 DLG3 GJB1 PHKA1 PGK1 TSPAN6 BTK IRS4 HTR2C GRIA3 CNGA2 BCAP31 IRAK1 FLNA |
| chrX: 5805129-49051018 | 1949 | 43245889 | 1 | 8783639811 | TMSB4X PPEF1 PHKA2 CNKSR2 SAT1 XK HDAC6 PQBP1 |
| chrX: 151571917-153603660 | 537 | 2031743 | 1 | 8783639811 | BCAP31 IRAK1 FLNA |
| chrX: 113820904-115588655 | 868 | 1767751 | 1 | 8783639811 | HTR2C |
| chrX: 66784200-66832422 | 151 | 48222 | 1 | 8783639811 | AR |
| chrX: 153317043-153580971 | 131 | 263928 | 1 | 8783639811 | FLNA |
| chr5: 53457886-53498009 | 98 | 40123 | 3 | 8783639811 | ARL15 |
| chr1: 237792067-237792654 | 3 | 587 | 3 | 8783639811 | RYR2 |
| chr1: 237800047-237800335 | 3 | 288 | 3 | 8783639811 | RYR2 |
| chr15: 67863370-67888404 | 73 | 25034 | 3 | 8894236501 | MAP2K5 |
| chr10: 54015852-54017650 | 7 | 1798 | 3 | 8894236501 | PRKG1 |
| chr5: 53569361-53570064 | 4 | 703 | 3 | 8894236501 | ARL15 |
| chr1: 237800047-237800335 | 3 | 288 | 3 | 8894236501 | RYR2 |
| chr3: 7634038-7634315 | 3 | 277 | 3 | 8894236501 | GRM7 |
| chrX: 66761119-153580971 | 3532 | 86819852 | 3 | 9023329892 | AR EFNB1 DLG3 GJB1 PHKA1 PGK1 TSPAN6 BTK IRS4 HTR2C GRIA3 CNGA2 BCAP31 IRAK1 FLNA |
| chrX: 66935629-113819143 | 133 | 46883514 | 3 | 9023329892 | AR EFNB1 DLG3 GJB1 PHKA1 PGK1 TSPAN6 BTK IRS4 HTR2C |
| chrX: 5805129-49057162 | 1966 | 43252033 | 3 | 9023329892 | TMSB4X PPEF1 PHKA2 CNKSR2 SAT1 XK HDAC6 PQBP1 |
| chrX: 115571479-146991276 | 975 | 31419797 | 3 | 9023329892 | GRIA3 |
| chrX: 153582356-153603660 | 58 | 21304 | 3 | 9023329892 | FLNA |
| chrX: 153362125-153580753 | 21 | 218628 | 3 | 9023329892 | FLNA |
| chr5: 78674209-78680667 | 15 | 6458 | 3 | 9023329892 | HOMER1 |
| chr10: 54015852-54018132 | 9 | 2280 | 3 | 9023329892 | PRKG1 |
| chr3: 7634038-7634315 | 3 | 277 | 4 | 9023329892 | GRM7 |

-continued

| CNVCall(hg19) | Num Probes | Length | CN | SampleID | GRMNetworkGenes |
|---|---|---|---|---|---|
| chr3: 47985150-47987833 | 7 | 2683 | 1 | 9087812957 | MAP4 |
| chr20: 8410187-8410935 | 3 | 748 | 1 | 9087812957 | PLCB1 |
| chrX: 66761119-153580971 | 3533 | 86819852 | 3 | 9087812957 | AR EFNB1 DLG3 GJB1 PHKA1 PGK1 TSPAN6 BTK IRS4 HTR2C GRIA3 CNGA2 BCAP31 IRAK1 FLNA |
| chrX: 66935880-113819143 | 132 | 46883263 | 3 | 9087812957 | AR EFNB1 DLG3 GJB1 PHKA1 PGK1 TSPAN6 BTK IRS4 HTR2C |
| chrX: 5805129-49057162 | 1966 | 43252033 | 3 | 9087812957 | TMSB4X PPEF1 PHKA2 CNKSR2 SAT1 XK HDAC6 PQBP1 |
| chrX: 113885458-147025473 | 1719 | 33140015 | 3 | 9087812957 | HTR2C GRIA3 |
| chrX: 153581379-153603660 | 63 | 22281 | 3 | 9087812957 | FLNA |
| chrX: 153362125-153577703 | 11 | 215578 | 3 | 9087812957 | FLNA |
| chr12: 79617078-79619484 | 9 | 2406 | 3 | 9087812957 | SYT1 |
| chr3: 7390277-7390613 | 3 | 336 | 3 | 9087812957 | GRM7 |
| chr14: 64886906-64887666 | 3 | 760 | 3 | 9087812957 | MTHFD1 |
| chr1: 237800047-237800335 | 3 | 288 | 3 | 9087812957 | RYR2 |
| chrX: 66761119-153603660 | 3595 | 86842541 | 1 | 9195709287 | AR EFNB1 DLG3 GJB1 PHKA1 PGK1 TSPAN6 BTK IRS4 HTR2C GRIA3 CNGA2 BCAP31 IRAK1 FLNA |
| chrX: 5805129-49053961 | 1955 | 43248832 | 1 | 9195709287 | TMSB4X PPEF1 PHKA2 CNKSR2 SAT1 XK HDAC6 PQBP1 |
| chrX: 113828384-151119409 | 1898 | 37291025 | 1 | 9195709287 | HTR2C GRIA3 CNGA2 |
| chrX: 153581379-153601624 | 57 | 20245 | 1 | 9195709287 | FLNA |
| chr3: 7400107-7401986 | 7 | 1879 | 1 | 9195709287 | GRM7 |
| chr10: 54016076-54018132 | 8 | 2056 | 1 | 9233697867 | PRKG1 |
| chr3: 171042118-171043337 | 3 | 1219 | 1 | 9233697867 | TNIK |
| chr12: 14094648-14095317 | 4 | 669 | 3 | 9233697867 | GRIN2B |
| chr10: 54016076-54018132 | 8 | 2056 | 1 | 9255801185 | PRKG1 |
| chrX: 66761119-153598601 | 3583 | 86837482 | 1 | 9483766919 | AR EFNB1 DLG3 GJB1 PHKA1 PGK1 TSPAN6 BTK IRS4 HTR2C GRIA3 CNGA2 BCAP31 IRAK1 FLNA |
| chrX: 5805129-49053961 | 1957 | 43248832 | 1 | 9483766919 | TMSB4X PPEF1 PHKA2 CNKSR2 SAT1 XK HDAC6 PQBP1 |
| chrX: 70364402-113819143 | 95 | 43454741 | 1 | 9483766919 | GJB1 PHKA1 PGK1 TSPAN6 BTK IRS4 HTR2C |
| chrX: 7255096-43740570 | 636 | 36485474 | 1 | 9483766919 | TMSB4X PPEF1 PHKA2 CNKSR2 SAT1 XK |
| chrX: 113819324-147010211 | 1855 | 33190887 | 1 | 9483766919 | HTR2C GRIA3 |
| chrX: 153580374-153597649 | 51 | 17275 | 1 | 9483766919 | FLNA |
| chr10: 54015852-54018132 | 9 | 2280 | 1 | 9483766919 | PRKG1 |
| chrX: 153601574-153603660 | 7 | 2086 | 1 | 9483766919 | FLNA |
| chr15: 67868782-67869255 | 3 | 473 | 1 | 9483766919 | MAP2K5 |
| chr5: 53497673-53506897 | 27 | 9224 | 1 | 9494272713 | ARL15 |
| chr15: 67868548-67869255 | 4 | 707 | 1 | 9494272713 | MAP2K5 |
| chr3: 7634038-7634315 | 3 | 277 | 4 | 03C18188A | GRM7 |
| chr1: 237800047-237800335 | 3 | 288 | 4 | 03C18188A | RYR2 |
| chr3: 7401335-7401986 | 4 | 651 | 1 | 03C18198A | GRM7 |
| chr15: 67879136-67888404 | 30 | 9268 | 3 | 03C18198A | MAP2K5 |
| chr20: 8284793-8285347 | 4 | 554 | 3 | 03C18198A | PLCB1 |
| chr14: 73689858-73690133 | 3 | 275 | 3 | 03C18198A | PSEN1 |
| chr14: 64886906-64887666 | 3 | 760 | 3 | 03C18198A | MTHFD1 |
| chr13: 98103980-98108313 | 14 | 4333 | 1 | 03C18292A | RAP2A |
| chr10: 54015852-54017933 | 8 | 2081 | 1 | 03C18292A | PRKG1 |
| chr6: 152390044-152392065 | 7 | 2021 | 1 | 03C18292A | ESR1 |
| chr19: 51196003-51196458 | 4 | 455 | 1 | 03C18292A | SHANK1 |
| chr10: 54016076-54018132 | 8 | 2056 | 0 | 03C18293A | PRKG1 |
| chr13: 98103980-98108313 | 14 | 4333 | 1 | 03C18293A | RAP2A |

-continued

| CNVCall(hg19) | Num Probes | Length | CN | SampleID | GRMNetworkGenes |
|---|---|---|---|---|---|
| chr8: 56797311-56800527 | 10 | 3216 | 1 | 03C18293A | LYN |
| chr1: 237800047-237800335 | 3 | 288 | 3 | 03C18293A | RYR2 |
| chr14: 73689858-73690133 | 3 | 275 | 4 | 03C18293A | PSEN1 |
| chrX: 122372904-122373436 | 3 | 532 | 0 | 03C18304A | GRIA3 |
| chr13: 98103980-98108313 | 14 | 4333 | 1 | 03C18304A | RAP2A |
| chr8: 56797726-56801075 | 11 | 3349 | 1 | 03C18304A | LYN |
| chr10: 54015852-54018132 | 9 | 2280 | 3 | 03C18304A | PRKG1 |
| chr6: 152390044-152392065 | 7 | 2021 | 0 | 03C18593A | ESR1 |
| chr10: 54016726-54018132 | 6 | 1406 | 1 | 03C18593A | PRKG1 |
| chr6: 88846690-88867529 | 65 | 20839 | 3 | 03C18593A | CNR1 |
| chr15: 67879136-67888404 | 30 | 9268 | 3 | 03C18593A | MAP2K5 |
| chr20: 8284793-8285347 | 4 | 554 | 3 | 03C18593A | PLCB1 |
| chr1: 237800047-237800335 | 3 | 288 | 3 | 03C18593A | RYR2 |
| chr1: 169699983-169700272 | 3 | 289 | 3 | 03C18593A | SELE |
| chr10: 54016076-54018132 | 8 | 2056 | 1 | 03C18601A | PRKG1 |
| chr6: 152390044-152392065 | 7 | 2021 | 1 | 03C18601A | ESR1 |
| chr6: 88846690-88867225 | 64 | 20535 | 3 | 03C18601A | CNR1 |
| chr20: 8284793-8285347 | 4 | 554 | 3 | 03C18601A | PLCB1 |
| chr7: 126514722-126534591 | 21 | 19869 | 3 | 03C20235A | GRM8 |
| chr10: 54016509-54018132 | 7 | 1623 | 1 | 03C20236A | PRKG1 |
| chr1: 237883563-237884209 | 3 | 646 | 0 | 03C202518 | RYR2 |
| chrX: 122476453-122477214 | 3 | 761 | 0 | 03C202518 | GRIA3 |
| chr1: 240026455-240028177 | 3 | 1722 | 0 | 03C202518 | CHRM3 |
| chr3: 47917471-47918280 | 2 | 809 | 0 | 03C202518 | MAP4 |
| chr3: 7578629-7580831 | 8 | 2202 | 1 | 03C202518 | GRM7 |
| chr9: 140881415-140882496 | 5 | 1081 | 1 | 03C202518 | CACNA1B |
| chr12: 79440378-79441073 | 3 | 695 | 1 | 03C202518 | SYT1 |
| chr5: 53400288-53400785 | 3 | 497 | 1 | 03C202518 | ARL15 |
| chr22: 22116258-22117111 | 3 | 853 | 1 | 03C202518 | MAPK1 |
| chr3: 7390277-7390613 | 3 | 336 | 4 | 03C21030A | GRM7 |
| chr1: 237800047-237800335 | 3 | 288 | 4 | 03C21030A | RYR2 |
| chr10: 54016076-54018132 | 8 | 2056 | 1 | 03C21031A | PRKG1 |
| chr15: 67879136-67888404 | 30 | 9268 | 3 | 03C21031A | MAP2K5 |
| chr20: 8284793-8285347 | 4 | 554 | 3 | 03C21031A | PLCB1 |
| chr12: 14094648-14094993 | 3 | 345 | 3 | 03C21031A | GRIN2B |
| chr1: 237800047-237800335 | 3 | 288 | 3 | 03C21031A | RYR2 |
| chr14: 96684129-96690516 | 19 | 6387 | 1 | 03C21050A | BDKRB2 |
| chr3: 47985150-47987833 | 7 | 2683 | 1 | 03C21050A | MAP4 |
| chr10: 54016726-54017933 | 5 | 1207 | 1 | 03C21050A | PRKG1 |
| chr7: 45674826-45676797 | 5 | 1971 | 3 | 03C21050A | ADCY1 |
| chr1: 237800047-237800335 | 3 | 288 | 3 | 03C21050A | RYR2 |
| chr12: 14094648-14094993 | 3 | 345 | 3 | 03C21050A | GRIN2B |
| chr14: 73689858-73690133 | 3 | 275 | 3 | 03C21050A | PSEN1 |
| chr14: 96684129-96690516 | 19 | 6387 | 1 | 03C21067A | BDKRB2 |
| chr10: 54016076-54017933 | 7 | 1857 | 1 | 03C21067A | PRKG1 |
| chr3: 7400950-7401986 | 5 | 1036 | 1 | 03C21067A | GRM7 |
| chr10: 54016076-54018451 | 9 | 2375 | 3 | 03C21638A | PRKG1 |
| chr10: 52927188-52928527 | 5 | 1339 | 3 | 03C22182A | PRKG1 |
| chr1: 237800047-237800335 | 3 | 288 | 4 | 03C22182A | RYR2 |
| chr5: 159349807-159351427 | 6 | 1620 | 1 | 03C23117 | ADRA1B |
| chr14: 73689858-73690133 | 3 | 275 | 3 | 03C23117 | PSEN1 |
| chr1: 237800047-237800335 | 3 | 288 | 3 | 03C23117 | RYR2 |
| chr10: 54015852-54017933 | 8 | 2081 | 3 | 03C23667A | PRKG1 |
| chr20: 8284793-8285347 | 4 | 554 | 3 | 03C23667A | PLCB1 |
| chr1: 237800047-237800335 | 3 | 288 | 3 | 03C23667A | RYR2 |
| chr1: 237800047-237800335 | 3 | 288 | 4 | 03C23695A | RYR2 |
| chr3: 7634038-7634315 | 3 | 277 | 4 | 03C23695A | GRM7 |
| chr20: 10233322-10233792 | 3 | 470 | 4 | 03C23695A | SNAP25 |
| chr10: 54016076-54018132 | 8 | 2056 | 0 | 03C23696A | PRKG1 |
| chr3: 7400107-7401986 | 7 | 1879 | 1 | 03C23696A | GRM7 |
| chr1: 237800047-237800335 | 3 | 288 | 4 | 03C23696A | RYR2 |
| chr22: 22179976-22216245 | 81 | 36269 | 1 | 04C23704A | MAPK1 |
| chr1: 237800047-237800335 | 3 | 288 | 4 | 04C23704A | RYR2 |
| chr11: 88635175-88664145 | 25 | 28970 | 1 | 04C24102A | GRM5 |
| chrX: 66761119-153581425 | 3533 | 86820306 | 3 | 04C24102A | AR EFNB1 DLG3 GJB1 PHKA1 PGK1 TSPAN6 BTK IRS4 HTR2C GRIA3 CNGA2 BCAP31 IRAK1 FLNA |
| chrX: 66941941-113819143 | 113 | 46877202 | 3 | 04C24102A | AR EFNB1 DLG3 GJB1 PHKA1 PGK1 TSPAN6 BTK IRS4 HTR2C |

-continued

| CNVCall(hg19) | Num Probes | Length | CN | SampleID | GRMNetworkGenes |
|---|---|---|---|---|---|
| chrX: 5805129-49057162 | 1965 | 43252033 | 3 | 04C24102A | TMSB4X PPEF1 PHKA2 CNKSR2 SAT1 XK HDAC6 PQBP1 |
| chrX: 113843040-147033557 | 1866 | 33190517 | 3 | 04C24102A | HTR2C GRIA3 |
| chrX: 43739511-49056654 | 55 | 5317143 | 3 | 04C24102A | HDAC6 PQBP1 |
| chrX: 153582356-153603660 | 59 | 21304 | 3 | 04C24102A | FLNA |
| chrX: 153361694-153577703 | 13 | 216009 | 3 | 04C24102A | FLNA |
| chr10: 54015852-54018132 | 9 | 2280 | 3 | 04C24102A | PRKG1 |
| chrX: 66761119-153584620 | 3537 | 86823501 | 1 | 04C24103A | AR EFNB1 DLG3 GJB1 PHKA1 PGK1 TSPAN6 BTK IRS4 HTR2C GRIA3 CNGA2 BCAP31 IRAK1 FLNA |
| chrX: 5805129-49051018 | 1945 | 43245889 | 1 | 04C24103A | TMSB4X PPEF1 PHKA2 CNKSR2 SAT1 XK HDAC6 PQBP1 |
| chrX: 7244669-43740265 | 662 | 36495596 | 1 | 04C24103A | TMSB4X PPEF1 PHKA2 CNKSR2 SAT1 XK |
| chrX: 113819324-122325013 | 924 | 8505689 | 1 | 04C24103A | HTR2C GRIA3 |
| chrX: 153294925-153583648 | 203 | 288723 | 1 | 04C24103A | FLNA |
| chrX: 66784200-66813604 | 98 | 29404 | 1 | 04C24103A | AR |
| chrX: 153585928-153603660 | 49 | 17732 | 1 | 04C24103A | FLNA |
| chr9: 140783374-140785168 | 6 | 1794 | 1 | 04C24103A | CACNA1B |
| chr5: 159349807-159351164 | 5 | 1357 | 1 | 04C24103A | ADRA1B |
| chr3: 7205629-7227957 | 62 | 22328 | 1 | 04C24700 | GRM7 |
| chr4: 86705101-86707016 | 8 | 1915 | 1 | 04C24700 | ARHGAP24 |
| chr3: 7400950-7401986 | 5 | 1036 | 1 | 04C24700 | GRM7 |
| chr10: 54016509-54018132 | 7 | 1623 | 3 | 04C24700 | PRKG1 |
| chr20: 10233322-10233792 | 3 | 470 | 3 | 04C24700 | SNAP25 |
| chr3: 7634038-7634315 | 3 | 277 | 3 | 04C24700 | GRM7 |
| chr1: 237800047-237800335 | 3 | 288 | 3 | 04C24700 | RYR2 |
| chr3: 7400950-7401986 | 5 | 1036 | 0 | 04C25535A | GRM7 |
| chr10: 54015852-54017933 | 8 | 2081 | 1 | 04C25535A | PRKG1 |
| chr3: 7400950-7401986 | 5 | 1036 | 0 | 04C25539A | GRM7 |
| chr10: 54016076-54018132 | 8 | 2056 | 1 | 04C25539A | PRKG1 |
| chr20: 8284793-8285347 | 4 | 554 | 3 | 04C25539A | PLCB1 |
| chr1: 237800047-237800335 | 3 | 288 | 3 | 04C25539A | RYR2 |
| chr19: 45768317-45768929 | 3 | 612 | 3 | 04C25539A | MARK4 |
| chr3: 7401335-7401986 | 4 | 651 | 0 | 04C25727A | GRM7 |
| chr3: 7205629-7227957 | 62 | 22328 | 1 | 04C25727A | GRM7 |
| chr4: 86705101-86707016 | 8 | 1915 | 1 | 04C25727A | ARHGAP24 |
| chr3: 7634038-7634315 | 3 | 277 | 3 | 04C25727A | GRM7 |
| chr3: 7400950-7401986 | 5 | 1036 | 0 | 04C25776A | GRM7 |
| chr10: 54016076-54018132 | 8 | 2056 | 1 | 04C25776A | PRKG1 |
| chrX: 66761119-153603660 | 3595 | 86842541 | 3 | 04C25776A | AR EFNB1 DLG3 GJB1 PHKA1 PGK1 TSPAN6 BTK IRS4 HTR2C GRIA3 CNGA2 BCAP31 IRAK1 FLNA |
| chrX: 5805129-49057162 | 1966 | 43252033 | 3 | 04C25776A | TMSB4X PPEF1 PHKA2 CNKSR2 SAT1 XK HDAC6 PQBP1 |
| chrX: 7200554-43702934 | 670 | 36502380 | 3 | 04C25776A | TMSB4X PPEF1 PHKA2 CNKSR2 SAT1 XK |
| chrX: 113849160-151475320 | 2229 | 37626160 | 3 | 04C25776A | HTR2C GRIA3 CNGA2 |
| chrX: 152800026-153601624 | 419 | 801598 | 3 | 04C25776A | BCAP31 IRAK1 FLNA |
| chrX: 152844142-153361493 | 193 | 517351 | 3 | 04C25776A | BCAP31 IRAK1 |
| chrX: 153584976-153597649 | 37 | 12673 | 3 | 04C25776A | FLNA |
| chr10: 54016076-54018132 | 8 | 2056 | 0 | 04C25781A | PRKG1 |
| chrX: 66761119-153598601 | 3581 | 86837482 | 1 | 04C25781A | AR EFNB1 DLG3 GJB1 PHKA1 PGK1 TSPAN6 BTK IRS4 HTR2C GRIA3 CNGA2 BCAP31 IRAK1 FLNA |

-continued

| CNVCall(hg19) | Num Probes | Length | CN | SampleID | GRMNetworkGenes |
|---|---|---|---|---|---|
| chrX: 5805129-49052017 | 1950 | 43246888 | 1 | 04C25781A | TMSB4X PPEF1 PHKA2 CNKSR2 SAT1 XK HDAC6 PQBP1 |
| chrX: 70364402-113819143 | 94 | 43454741 | 1 | 04C25781A | GJB1 PHKA1 PGK1 TSPAN6 BTK IRS4 HTR2C |
| chrX: 152800026-153597649 | 409 | 797623 | 1 | 04C25781A | BCAP31 IRAK1 FLNA |
| chrX: 152844958-153576946 | 200 | 731988 | 1 | 04C25781A | BCAP31 IRAK1 FLNA |
| chrX: 113819324-122431297 | 1244 | 8611973 | 1 | 04C25781A | HTR2C GRIA3 |
| chrX: 147004748-151570873 | 661 | 4566125 | 1 | 04C25781A | CNGA2 |
| chrX: 66785040-66937048 | 358 | 152008 | 1 | 04C25781A | AR |
| chr3: 7400107-7401986 | 7 | 1879 | 1 | 04C25781A | GRM7 |
| chrX: 153601574-153603660 | 7 | 2086 | 1 | 04C25781A | FLNA |
| chr5: 159349807-159351164 | 5 | 1357 | 1 | 04C25781A | ADRA1B |
| chrX: 122350880-122351648 | 4 | 768 | 1 | 04C25781A | GRIA3 |
| chr10: 54015852-54017933 | 8 | 2081 | 3 | 04C27115 | PRKG1 |
| chr10: 54015852-54018132 | 9 | 2280 | 3 | 04C29842 | PRKG1 |
| chr1: 237800047-237800335 | 3 | 288 | 3 | 04C29842 | RYR2 |
| chr20: 8284793-8285347 | 4 | 554 | 3 | 04C30025 | PLCB1 |
| chr19: 3153225-3154967 | 3 | 1742 | 3 | 04C30025 | GNA15 |
| chr1: 169699983-169700272 | 3 | 289 | 3 | 04C30025 | SELE |
| chr1: 237800047-237800335 | 3 | 288 | 3 | 04C30025 | RYR2 |
| chr10: 54016076-54018132 | 8 | 2056 | 0 | 04C31454 | PRKG1 |
| chr3: 7400950-7401986 | 5 | 1036 | 0 | 04C31454 | GRM7 |
| chr3: 7400950-7401986 | 5 | 1036 | 1 | 04C33421A | GRM7 |
| chr15: 67868782-67869255 | 3 | 473 | 1 | 04C33421A | MAP2K5 |
| chr5: 78674209-78681761 | 16 | 7552 | 3 | 04C33421A | HOMER1 |
| chr20: 8832925-8833223 | 3 | 298 | 3 | 04C33421A | PLCB1 |
| chr1: 237800047-237800335 | 3 | 288 | 4 | 04C33421A | RYR2 |
| chr3: 7634038-7634315 | 3 | 277 | 4 | 04C33421A | GRM7 |
| chr10: 54016076-54018132 | 8 | 2056 | 0 | 04C34109A | PRKG1 |
| chr13: 98103980-98108313 | 14 | 4333 | 1 | 04C34109A | RAP2A |
| chr5: 78674209-78680667 | 15 | 6458 | 3 | 04C34109A | HOMER1 |
| chr1: 237800047-237800335 | 3 | 288 | 4 | 04C34109A | RYR2 |
| chr3: 7634038-7634315 | 3 | 277 | 4 | 04C34109A | GRM7 |
| chr5: 159349807-159351164 | 5 | 1357 | 1 | 04C34647 | ADRA1B |
| chr20: 10233322-10233792 | 3 | 470 | 3 | 04C34647 | SNAP25 |
| chr1: 237800047-237800335 | 3 | 288 | 3 | 04C34647 | RYR2 |
| chr5: 78674209-78680667 | 15 | 6458 | 3 | 04C34670A | HOMER1 |
| chr3: 7634038-7634315 | 3 | 277 | 4 | 04C34670A | GRM7 |
| chr1: 237800047-237800335 | 3 | 288 | 4 | 04C34670A | RYR2 |
| chr10: 54015852-54018132 | 9 | 2280 | 3 | 04C34687A | PRKG1 |
| chr1: 237800047-237800335 | 3 | 288 | 3 | 04C34687A | RYR2 |
| chr21: 31077464-31078899 | 6 | 1435 | 1 | 04C35100A | GRIK1 |
| chr20: 8284793-8285347 | 4 | 554 | 3 | 04C35100A | PLCB1 |
| chr20: 8476391-8477382 | 4 | 991 | 3 | 04C35100A | PLCB1 |
| chr1: 237800047-237800335 | 3 | 288 | 3 | 04C35100A | RYR2 |
| chr10: 53203699-53211914 | 28 | 8215 | 1 | 04C35139 | PRKG1 |
| chr10: 54016076-54017933 | 7 | 1857 | 1 | 04C35139 | PRKG1 |
| chr10: 54016076-54018132 | 8 | 2056 | 1 | 04C35147 | PRKG1 |
| chrX: 122372904-122373436 | 3 | 532 | 0 | 04C35397A | GRIA3 |
| chr10: 54015852-54017428 | 6 | 1576 | 3 | 04C35397A | PRKG1 |
| chr20: 10233322-10233792 | 3 | 470 | 3 | 04C35397A | SNAP25 |
| chr1: 237800047-237800335 | 3 | 288 | 3 | 04C35397A | RYR2 |
| chr3: 7390277-7390613 | 3 | 336 | 3 | 04C35397A | GRM7 |
| chr14: 73689858-73690133 | 3 | 275 | 4 | 04C35397A | PSEN1 |
| chr11: 67046852-67054810 | 28 | 7958 | 1 | 04C35733A | ADRBK1 |
| chr13: 23992587-23999573 | 24 | 6986 | 1 | 04C35733A | SACS |
| chr10: 112835849-112841123 | 16 | 5274 | 1 | 04C35733A | ADRA2A |
| chr3: 48028424-48058083 | 56 | 29659 | 3 | 04C35733A | MAP4 |
| chr6: 152152611-152156721 | 13 | 4110 | 3 | 04C35733A | ESR1 |
| chr6: 152196877-152198173 | 6 | 1296 | 3 | 04C35733A | ESR1 |
| chr19: 51193847-51194583 | 4 | 736 | 3 | 04C35733A | SHANK1 |
| chr1: 237800047-237800335 | 3 | 288 | 4 | 04C35733A | RYR2 |
| chr10: 112836168-112838471 | 8 | 2303 | 1 | 04C36096A | ADRA2A |
| chr15: 45318916-45323810 | 13 | 4894 | 3 | 04C36096A | SORD |
| chr19: 45767849-45768929 | 5 | 1080 | 3 | 04C36096A | MARK4 |
| chr1: 237800047-237800335 | 3 | 288 | 3 | 04C36096A | RYR2 |
| chr10: 54016076-54018132 | 8 | 2056 | 0 | 04C36504A | PRKG1 |
| chr13: 98103980-98108313 | 14 | 4333 | 1 | 04C36504A | RAP2A |
| chr10: 112836168-112838471 | 8 | 2303 | 1 | 04C36504A | ADRA2A |
| chr3: 7401335-7401986 | 4 | 651 | 1 | 04C36504A | GRM7 |
| chr1: 237800047-237800335 | 3 | 288 | 3 | 04C36504A | RYR2 |
| chr10: 54015852-54018132 | 9 | 2280 | 3 | 04C37450 | PRKG1 |

-continued

| CNVCall(hg19) | Num Probes | Length | CN | SampleID | GRMNetworkGenes |
|---|---|---|---|---|---|
| chr12: 14094648-14094993 | 3 | 345 | 3 | 04C37450 | GRIN2B |
| chr10: 54016076-54018132 | 8 | 2056 | 0 | 04C37686A | PRKG1 |
| chr20: 8410187-8410935 | 3 | 748 | 1 | 04C37686A | PLCB1 |
| chr1: 237800047-237800335 | 3 | 288 | 3 | 04C37686A | RYR2 |
| chr20: 8832925-8833223 | 3 | 298 | 3 | 04C37703A | PLCB1 |
| chr14: 73689858-73690133 | 3 | 275 | 3 | 04C37703A | PSEN1 |
| chr1: 237800047-237800335 | 3 | 288 | 3 | 04C37703A | RYR2 |
| chrX: 122372591-122373436 | 4 | 845 | 0 | 04C37866 | GRIA3 |
| chr3: 7401335-7401986 | 4 | 651 | 1 | 04C37866 | GRM7 |
| chrX: 66761119-153361962 | 3509 | 86600843 | 3 | 04C37866 | AR EFNB1 DLG3 GJB1 PHKA1 PGK1 TSPAN6 BTK IRS4 HTR2C GRIA3 CNGA2 BCAP31 IRAK1 |
| chrX: 5805129-49057162 | 1964 | 43252033 | 3 | 04C37866 | TMSB4X PPEF1 PHKA2 CNKSR2 SAT1 XK HDAC6 PQBP1 |
| chr10: 54015852-54017428 | 6 | 1576 | 3 | 04C37866 | PRKG1 |
| chr20: 8284793-8285347 | 4 | 554 | 3 | 04C37866 | PLCB1 |
| chr20: 8832925-8833223 | 3 | 298 | 3 | 04C37866 | PLCB1 |
| chr1: 237800047-237800335 | 3 | 288 | 3 | 04C37866 | RYR2 |
| chr13: 98103980-98108313 | 14 | 4333 | 1 | 04C38210A | RAP2A |
| chr10: 54015852-54019607 | 14 | 3755 | 1 | 04C38210A | PRKG1 |
| chr10: 54016076-54018132 | 8 | 2056 | 1 | 04C38472A | PRKG1 |
| chr3: 7400107-7401986 | 7 | 1879 | 1 | 04C38472A | GRM7 |
| chr6: 152390044-152392065 | 7 | 2021 | 1 | 04C38472A | ESR1 |
| chr15: 67868548-67869255 | 4 | 707 | 1 | 04C38472A | MAP2K5 |
| chr1: 237800047-237800335 | 3 | 288 | 4 | 04C38496A | RYR2 |
| chr3: 7390277-7390613 | 3 | 336 | 4 | 04C38496A | GRM7 |
| chr3: 7634038-7634315 | 3 | 277 | 4 | 04C38496A | GRM7 |
| chr1: 237800047-237800335 | 3 | 288 | 4 | 04C38497A | RYR2 |
| chr3: 7634038-7634315 | 3 | 277 | 4 | 04C38497A | GRM7 |
| chr11: 67046852-67054810 | 28 | 7958 | 1 | 05C38718 | ADRBK1 |
| chr10: 112835849-112841123 | 16 | 5274 | 1 | 05C38718 | ADRA2A |
| chr10: 54017100-54018132 | 5 | 1032 | 1 | 05C38718 | PRKG1 |
| chr6: 152154091-152156521 | 7 | 2430 | 3 | 05C38718 | ESR1 |
| chr15: 67879375-67880467 | 5 | 1092 | 3 | 05C38718 | MAP2K5 |
| chr20: 8832925-8833223 | 3 | 298 | 3 | 05C38718 | PLCB1 |
| chr1: 237800047-237800335 | 3 | 288 | 3 | 05C38718 | RYR2 |
| chr3: 7400107-7401986 | 7 | 1879 | 1 | 05C39206 | GRM7 |
| chr3: 7400107-7401986 | 7 | 1879 | 1 | 05C39207 | GRM7 |
| chr20: 8284793-8285347 | 4 | 554 | 3 | 05C39207 | PLCB1 |
| chr14: 73689858-73690133 | 3 | 275 | 3 | 05C39207 | PSEN1 |
| chr3: 7634038-7634315 | 3 | 277 | 3 | 05C39207 | GRM7 |
| chr1: 237800047-237800335 | 3 | 288 | 3 | 05C39207 | RYR2 |
| chr15: 67868548-67869255 | 4 | 707 | 0 | 05C39293 | MAP2K5 |
| chr10: 54016076-54018132 | 8 | 2056 | 1 | 05C39303 | PRKG1 |
| chr6: 152389170-152392065 | 11 | 2895 | 1 | 05C39303 | ESR1 |
| chr5: 78674209-78682669 | 17 | 8460 | 3 | 05C39303 | HOMER1 |
| chr12: 79617078-79619484 | 9 | 2406 | 3 | 05C39303 | SYT1 |
| chr1: 237800047-237800335 | 3 | 288 | 3 | 05C39303 | RYR2 |
| chr11: 67046852-67054006 | 25 | 7154 | 1 | 05C39753A | ADRBK1 |
| chr1: 237800047-237800335 | 3 | 288 | 3 | 05C39753A | RYR2 |
| chr5: 78678983-78680667 | 3 | 1684 | 4 | 05C39753A | HOMER1 |
| chr3: 7634038-7634315 | 3 | 277 | 4 | 05C39753A | GRM7 |
| chr10: 54015852-54018132 | 9 | 2280 | 0 | 05C40121 | PRKG1 |
| chrX: 122372591-122373436 | 4 | 845 | 0 | 05C40121 | GRIA3 |
| chr4: 158246480-158288169 | 127 | 41689 | 1 | 05C40121 | GRIA2 |
| chr11: 88422009-88445927 | 85 | 23918 | 1 | 05C40121 | GRM5 |
| chr1: 239882350-239901631 | 63 | 19281 | 1 | 05C40121 | CHRM3 |
| chr13: 47415498-47430157 | 47 | 14659 | 1 | 05C40121 | HTR2A |
| chr4: 86705101-86714668 | 32 | 9567 | 1 | 05C40121 | ARHGAP24 |
| chr4: 158214305-158222060 | 30 | 7755 | 1 | 05C40121 | GRIA2 |
| chrX: 122361879-122369973 | 29 | 8094 | 1 | 05C40121 | GRIA3 |
| chr7: 126150890-126158673 | 27 | 7783 | 1 | 05C40121 | GRM8 |
| chr13: 47466827-48655019 | 20 | 1188192 | 1 | 05C40121 | HTR2A |
| chr12: 79800156-79805320 | 16 | 5164 | 1 | 05C40121 | SYT1 |
| chr5: 78674209-78680667 | 15 | 6458 | 1 | 05C40121 | HOMER1 |
| chr12: 79748574-79751065 | 9 | 2491 | 1 | 05C40121 | SYT1 |
| chr1: 237210290-237211943 | 8 | 1653 | 1 | 05C40121 | RYR2 |
| chr1: 237917997-237919027 | 7 | 1030 | 1 | 05C40121 | RYR2 |
| chr19: 3152363-3154967 | 6 | 2604 | 1 | 05C40121 | GNA15 |
| chr6: 146759565-150131412 | 125 | 3371847 | 3 | 05C40121 | PCMT1 |
| chr3: 48064539-48128750 | 93 | 64211 | 3 | 05C40121 | MAP4 |
| chr8: 56791171-56820593 | 66 | 29422 | 3 | 05C40121 | LYN |

-continued

| CNVCall(hg19) | Num Probes | Length | CN | SampleID | GRMNetworkGenes |
|---|---|---|---|---|---|
| chr11: 108001419-108018579 | 43 | 17160 | 3 | 05C40121 | ACAT1 |
| chr8: 56848498-56860495 | 30 | 11997 | 3 | 05C40121 | LYN |
| chr1: 237465780-237476925 | 27 | 11145 | 3 | 05C40121 | RYR2 |
| chr12: 79698309-79707403 | 20 | 9094 | 3 | 05C40121 | SYT1 |
| chr7: 45611468-45616912 | 15 | 5444 | 3 | 05C40121 | ADCY1 |
| chr14: 73647557-73654465 | 9 | 6908 | 3 | 05C40121 | PSEN1 |
| chr1: 237657230-237998101 | 963 | 340871 | 3 | 05C42621A | RYR2 |
| chr10: 54016076-54018132 | 8 | 2056 | 3 | 05C42733 | PRKG1 |
| chr3: 7400107-7401986 | 7 | 1879 | 1 | 05C42734 | GRM7 |
| chr15: 67868548-67869255 | 4 | 707 | 1 | 05C42734 | MAP2K5 |
| chr15: 67878584-67888404 | 32 | 9820 | 3 | 05C42734 | MAP2K5 |
| chr6: 152390044-152394474 | 15 | 4430 | 3 | 05C42734 | ESR1 |
| chr10: 54016076-54017933 | 7 | 1857 | 3 | 05C42734 | PRKG1 |
| chr1: 237800047-237800335 | 3 | 288 | 3 | 05C42734 | RYR2 |
| chr20: 8476391-8477382 | 4 | 991 | 3 | 05C43931 | PLCB1 |
| chr3: 7634038-7634315 | 3 | 277 | 3 | 05C43931 | GRM7 |
| chr3: 7390277-7390613 | 3 | 336 | 3 | 05C43931 | GRM7 |
| chr10: 54016076-54017933 | 7 | 1857 | 3 | 05C44090A | PRKG1 |
| chr10: 54016509-54018132 | 7 | 1623 | 1 | 05C44389 | PRKG1 |
| chr15: 67868548-67869255 | 4 | 707 | 1 | 05C44389 | MAP2K5 |
| chr5: 78674209-78680667 | 15 | 6458 | 3 | 05C44389 | HOMER1 |
| chr12: 79617078-79618980 | 7 | 1902 | 3 | 05C44389 | SYT1 |
| chr1: 237800047-237800335 | 3 | 288 | 4 | 05C44389 | RYR2 |
| chr5: 159349807-159351427 | 6 | 1620 | 1 | 05C44390 | ADRA1B |
| chr10: 54015852-54018132 | 9 | 2280 | 3 | 05C44390 | PRKG1 |
| chr13: 98103980-98107960 | 13 | 3980 | 1 | 05C45522 | RAP2A |
| chr5: 78674209-78680667 | 15 | 6458 | 3 | 05C45522 | HOMER1 |
| chr12: 13835447-13836832 | 5 | 1385 | 3 | 05C45522 | GRIN2B |
| chr1: 237800047-237800335 | 3 | 288 | 3 | 05C45522 | RYR2 |
| chr3: 7634038-7634315 | 3 | 277 | 3 | 05C45522 | GRM7 |
| chr11: 88614158-88719775 | 109 | 105617 | 1 | 05C45572 | GRM5 |
| chr11: 88614158-88719775 | 109 | 105617 | 1 | 05C46062 | GRM5 |
| chr3: 7400107-7401986 | 7 | 1879 | 1 | 05C46062 | GRM7 |
| chr11: 88614158-88719775 | 109 | 105617 | 1 | 05C46063 | GRM5 |
| chr10: 54015852-54018132 | 9 | 2280 | 1 | 05C46063 | PRKG1 |
| chr6: 152390044-152392065 | 7 | 2021 | 1 | 05C46063 | ESR1 |
| chr3: 7400107-7401986 | 7 | 1879 | 1 | 05C46063 | GRM7 |
| chr3: 47985150-47987833 | 7 | 2683 | 1 | 05C46596A | MAP4 |
| chr5: 78674209-78682669 | 17 | 8460 | 3 | 05C46672 | HOMER1 |
| chr20: 8832925-8833223 | 3 | 298 | 4 | 05C46672 | PLCB1 |
| chr3: 7390277-7390613 | 3 | 336 | 4 | 05C46672 | GRM7 |
| chr1: 237800047-237800335 | 3 | 288 | 4 | 05C46672 | RYR2 |
| chr11: 88637835-88662604 | 21 | 24769 | 1 | 05C46673 | GRM5 |
| chr10: 54015852-54018132 | 9 | 2280 | 3 | 05C46673 | PRKG1 |
| chr1: 237800047-237800335 | 3 | 288 | 4 | 05C46673 | RYR2 |
| chr19: 51196003-51196458 | 4 | 455 | 1 | 05C46991 | SHANK1 |
| chrX: 66761119-153603660 | 3596 | 86842541 | 3 | 05C46991 | AR EFNB1 DLG3 GJB1 PHKA1 PGK1 TSPAN6 BTK IRS4 HTR2C GRIA3 CNGA2 BCAP31 IRAK1 FLNA |
| chrX: 5805129-49053394 | 1955 | 43248265 | 3 | 05C46991 | TMSB4X PPEF1 PHKA2 CNKSR2 SAT1 XK HDAC6 PQBP1 |
| chrX: 113825397-151361733 | 2056 | 37536336 | 3 | 05C46991 | HTR2C GRIA3 CNGA2 |
| chrX: 152800026-153602907 | 423 | 802881 | 3 | 05C46991 | BCAP31 IRAK1 FLNA |
| chrX: 152844718-153361493 | 191 | 516775 | 3 | 05C46991 | BCAP31 IRAK1 |
| chrX: 66785892-66873353 | 229 | 87461 | 3 | 05C46991 | AR |
| chrX: 153584976-153597649 | 37 | 12673 | 3 | 05C46991 | FLNA |
| chrX: 113816265-113819143 | 11 | 2878 | 3 | 05C46991 | HTR2C |
| chr10: 54015852-54017933 | 8 | 2081 | 1 | 05C47048 | PRKG1 |
| chr9: 140783374-140785168 | 6 | 1794 | 1 | 05C47049 | CACNA1B |
| chr10: 54016076-54018132 | 8 | 2056 | 1 | 05C47086 | PRKG1 |
| chr3: 47985150-47987833 | 7 | 2683 | 1 | 05C47086 | MAP4 |

TABLE 20

CNV regions are listed by location and affected genes. CN refers to copy number state

| Gene | Count Samples Deletion | Count Samples Duplication |
|---|---|---|
| ACAT1 | 0 | 2 |
| ADCY1 | 0 | 2 |
| ADRA1B | 7 | 0 |
| ADRA2A | 4 | 0 |
| ADRBK1 | 3 | 0 |
| ARHGAP24 | 4 | 0 |
| ARL15 | 2 | 2 |
| BCAP31 | 12 | 19 |
| BDKRB2 | 2 | 0 |
| BTK | 10 | 15 |
| CACNA1B | 3 | 0 |
| CHRM3 | 3 | 0 |
| CNR1 | 0 | 2 |
| EFNB1 | 7 | 15 |
| FLNA | 21 | 28 |
| GNA15 | 1 | 3 |
| GRIK1 | 4 | 0 |
| GRM5 | 7 | 0 |
| GRM7 | 30 | 24 |
| GRM8 | 1 | 3 |
| HOMER1 | 1 | 9 |
| HTR2A | 2 | 0 |
| HTR2C | 17 | 24 |
| LYN | 2 | 2 |
| MAP4 | 6 | 2 |
| MAPK1 | 2 | 0 |
| MARK4 | 0 | 2 |
| MTHFD1 | 0 | 5 |
| PCMT1 | 0 | 2 |
| PHKA1 | 10 | 15 |
| PHKA2 | 11 | 15 |
| PLCB1 | 3 | 17 |
| PSEN1 | 0 | 11 |
| RAP2A | 13 | 0 |
| RYR2 | 4 | 54 |
| SACS | 2 | 0 |
| SELE | 0 | 2 |
| SHANK1 | 5 | 1 |
| SORD | 1 | 2 |
| TNIK | 3 | 0 |
| AR | 11 | 15 |
| CD163 | 0 | 2 |
| CNGA2 | 11 | 15 |
| CNKSR2 | 11 | 15 |
| DLG3 | 7 | 15 |
| ESR1 | 7 | 4 |
| GJB1 | 10 | 15 |
| GRIA2 | 2 | 0 |
| GRIA3 | 20 | 21 |
| GRIN2B | 0 | 8 |
| HDAC6 | 8 | 12 |
| IRAK1 | 12 | 19 |
| IRS4 | 10 | 15 |
| MAP2K5 | 11 | 9 |
| PGK1 | 10 | 15 |
| PPEF1 | 11 | 15 |
| PQBP1 | 8 | 12 |
| PRKG1 | 53 | 34 |
| SAT1 | 11 | 15 |
| SNAP25 | 0 | 5 |
| SYT1 | 3 | 4 |
| TMSB4X | 11 | 15 |
| TSPAN6 | 10 | 15 |
| XK | 11 | 15 |

(1 deletion; 2 normal wt; 3 duplication).

Table 21 shows 64 network genes which are enriched for CNVs and lists number of case subjects per CNV. These genes provide new targets for the design of therapeutics useful for the treatment and diagnosis of ADHD.

Several additional genes were identified using the Agilent system and are listed below.

Forward Only Gene Querying 2 degrees protein-protein interaction with GRM genes based on Cytoscape Human Interactome (As reported in Elia J, Glessner J T, et al. (2011) Genome-wide copy number variation study associates metabotropic glutamate receptor gene networks with attention deficit hyperactivity disorder. Nat Genet. 44, 78-84) are: GRM1; GRM2; GRM3; GRM4; GRM5; GRM6; GRM7; GRM8; TUBB; ITPR1; GAPDH; ADORA1; ADRBK1; GNA15; GNAQ; RGS12; RIF1; TNIK; HRPT2; FLNA; CALM2; HOMER1; CALM3; CALM1; GNAO1; TUBA1B; TUBA1A; PICK1; TUBA1; TUBA2; ADA; MC4R; RPLP2; ADRA2A; SRC; BDKRB2; ARRB1; SNCA; FPR1; OPRD1; PDE6G; IQGAP2; ADD2; PDE1C; PYGM; PHKG2; GLP2R; PTHR2; VIPR1; PHKA1; GLP1R; GRB7; ADD1; PDE1B; PYGL; PHKA2; SCTR; PHKB; CRHR1; ADCY1; KIAA1683; C17orf44; MYO6; LOC642393; DCN; ITGB1; GRB2; DRD3; FURIN; ARRB2; CDC42; RHOA; SELE; DRD2; HSP90AB1; VHL; GRIK1; F3; MTNR1A; GRIK3; ARHGAP24; ITGB7; TJP1; PSEN1; RALA; GP1BA; SHBG; TLR10; MTNR1B; ARL15; PCDHA4; RAB2; PSMD11; CAMK4; HBXIP; ACTB; PAFAH1B3; CAMK2B; BTBD2; G6PD; PGM1; PRDX1; CHP; CAMK1; EGFR; TK1; TXN; APP; RPA2; SLC2A1; LAMA4; SERPINB9; TPI1; QRICH2; S100A6; CNR1; CHRM2; ADRB2; GNAI1; ADRA2C; F2R; RGS2; HTR2A; TBXA2R; PIK3CA; BDKRB1; F2RL3; HTR2C; CHRM3; ADRA1B; BTK; F2RL2; TXNDC4; CA8; CCNB1; PLCB1; LYN; PLCG2; NPY2R; GNAI2; GNAI3; PLCB3; CACNA1B; IL8RB; MAPT; CALB2; LTA; FYN; TCP1; ZAP70; MYC; NMI; SIAH1; YWHAQ; PXN; TUBG1; DYNLL1; SDC3; SOCS6; SYK; SOCS7; MARK4; CNP; STAU1; PLA2G7; LOC653098; RYR2; SHANK1; STX12; CENTG1; C1orf116; GRIA1; HOMER3; GRM1; RYR1; APTX; AQP1; SACS; SLC6A3; LRP2BP; EFNB1; PRLHR; ACCN1; PRKCA; UBQLN4; ACCN2; ATXN7L3; ERBB2; CIC; BTG2; NFKBIA; PIK3R1; RAP2A; PSMC1; ANXA2; NANS; IMPDH2; SEPT4; RPN2; NUDC; MGC11082; MAPK1; TMEM4; UCHL1; PSMA1; SNRPB2; PSMD6; SET; COPB2; ACTR2; FKBP3; ACAT1; TBCA; PRPSAP1; PCMT1; MRPL14; EIF3S3; CMPK; PSMD13; NARG1; PCID1; RRM1; TRMT112; CACYBP; TYMS; GSN; SORD; SARS; PSMD1; KIAA0090; TRAF2; LRRC59; DISC1; PPP2R1A; STRAP; RANBP1; PSAT1; BCAP31; SETD4; GOT1; MTHFD1; NCK1; PCBP3; MRPS16; TXNL2; SF3B14; PPIH; ACP1; TEAD3; TFAM; DHCR7; ACAT2; DSTN; PCBP1; PRMT1; FSCN1; GPR26; HNRPA3; RPS14; RUVBL2; ECHS1; CYCS; PDCD5; RCC1; RCC2; LYAR; GNB2L1; HD; MX1; DLST; CHGB; ALDOA; PSME1; C7orf25; MAP4; and TGM2.

Reciprocal Gene Querying 2 degrees protein-protein interaction with GRM genes based on Cytoscape Human Interactome (forward/reverse) are: GRM1; GRM2; GRM3; GRM4; GRM5; GRM6; GRM7; GRM8; TUBB; ITPR1; GAPDH; ADORA1; ADRBK1; GNA15; GNAQ; RGS12; RIF1; TNIK; HRPT2; FLNA; CALM2; HOMER1; CALM3; CALM1; GNAO1; TUBA1B; TUBA1A; PICK1; TUBA1; TUBA2; PRKCA; HOMER2; PDCD8; C9orf25; SDCBP; PPM1A; PRKCZ; TUBA5; ACAT1; ACAT2; ACCN1; ACCN2; ACP1; ACTA1; ACTB; ADA; ADCY1; ADD1; ADD2; ADD3; ADRA1B; ADRA2A; ADRA2C; ADRB2; AKT1; ALDOA; ANXA2; APLP2; APP; AQP1; RHOA; ARRB1; ARRB2; ATP2B1; ATP2B2; BCL2; BDKRB1; BDKRB2; BTK; CA8; CACNA1B; CALB2; CAMK4; CAMK2B; CASP3; CASR; CBL; CCNB1; CD5; CD9; CDC42; CFTR; CHAT; RCC1; CHGB; CHRM2; CHRM3; CNP; CNR1; CREM; CRHR1; CSNK2B; DBN1;

DCN; DDX5; DHCR7; DLST; DNM1; DRD2; DRD3; DVL2; ECHS1; EEF1D; EEF2; EFNB1; EFNB2; EGFR; ERBB2; EWSR1; F2R; F2RL2; F3; FKBP3; FPR1; FYN; G6PD; GABRR1; GFAP; GFPT1; GJA1; GJB1; GLP1R; GMFB; GNAI1; GNAI2; GNAI3; GOT1; GP1BA; GPM6A; PRLHR; GRB2; GRB7; GRIA1; GRIA2; GRIA3; GRIA4; GRIK1; GRIK3; GRIN2A; GRIN2B; GSK3A; GSK3B; GSN; HD; HLA-A; HMGB1; HMGN1; HMGN2; PRMT1; HES1; HSPA1A; HSP90AB1; HTR2A; HTR2C; IKBKB; IL5RA; IL8RB; IMPDH2; INSR; IRS1; ITGB1; ITGB2; ITGB7; ITPKA; ITPKB; KCNE1; KIT; KRT10; KRT18; LAMA4; LCK; LMNA; LMNB1; LTA; LYN; MARCKS; MAP4; MAPT; MBP; MC4R; MGMT; MSN; MTHFD1; MTNR1A; MTNR1B; MX1; MYC; MYO6; MYOD1; NCF1C; NCK1; NCL; NFATC1; NFKBIA; NOS1; NPY2R; NRGN; OPRD1; PA2G4; FURIN; PAFAH1B3; PRDX1; PAM; PCBP1; PCMT1; PDE1C; PDE6D; PDE6G; PDE1B; PFKFB2; PGM1; PHKA1; PHKA2; PHKB; PHKG2; SERPINB9; PIK3CA; PIK3R1; PLCB3; PLCG2; PLD1; SEPT4; PPP2R1A; PPP3CA; PRKCD; PRKG1; MAPK1; PRPSAP1; PSEN1; PSMA1; PSMC1; PSMD1; PSMD11; PSMD13; PSME1; PTGIR; PTHR2; PTPN6; PTPN11; PTPN12; PTPRJ; PXN; PYGL; PYGM; RAB2; RAB5A; RAF1; RALA; RANBP1; RAP2A; RELA; RGS2; RGS7; RHO; RPA2; RPL10; RPLP2; RPN2; RPS14; RRAD; RRM1; RYR1; RYR2; S100A6; SARS; SCTR; SDC1; SDC2; SDC4; SELE; SET; SHBG; SHC1; STAHL SLC1A1; SLC2A1; SLC6A3; SLC6A9; SNAP25; SNCA; FSCN1; SNRPB2; SORD; SOX4; SPAG1; SPP1; SRC; STAU1; STX4; STXBP1; SYK; TBCA; TBXA2R; TCP1; TEAD3; TFAM; TGM2; TJP1; TK1; TNNI3; TNNT2; TOP2A; TP53; TPI1; TRAF2; TRPC3; TUBG1; TXN; TYMS; UCHL1; VCL; VHL; VIL2; VIPR1; VTN; YWHAB; ZAP70; BTG2; PLA2G7; DGKZ; DGKD; CAMK1; STC2; DYNLL1; EIF3S3; PEA15; EDF1; SNAP23; F2RL3; NMI; PDCD5; PSCD2; COPB2; SOCS6; CD163; GLP2R; HAND1; HOMER3; SDC3; PSMD6; SETDB1; ACTR2; BCAP31; RGS19; TMEM4; GNB2L1; PPIH; PCID1; TXNL2; HBXIP; NUDC; IQGAP2; RUVBL2; YWHAQ; CENTA1; DSTN; STRAP; CHP; HABP4; KIAA0090; TXNDC4; CIC; PLCB1; WWC1; POLA2; STX12; SACS; HSPB8; CACYBP; DISC1; WDR91; PSAT1; SOCS7; DRD1IP; F11R; SHANK1; MRPS16; TRMT112; SF3B14; CMPK; PCBP3; SETD4; NANS; CYCS; ARL15; APTX; LRRC59; TRPV6; IXL; BTBD2; LYAR; LRP2BP; RCC2; PCDHA4; UBQLN4; ATXN7L3; CORO1B; MARK4; MRPL14; C7orf25; C1orf116; NARG1; KIAA1683; TSC22D4; TLR10; ARHGAP24; QRICH2; C4orf14; MGC11082; PPP1R14A; CENTG1; GPR26; HNRPA3; C17orf44; LOC642393; LOC653098; GNAZ; EPB41L2; DRD1; GNAS; P2RY1; AKAP12; CCR5; PRKACA; CAPN2; PIK3CG; FSHR; CAV1; GIT2; MAPK3; AGTR1; GIT1; RCVRN; PDCL; PRKCG; PDC; FREQ; CCR4; PRKCB1; KRAS; CSNK2A1; KCNQ2; DLG3; MYO9B; PHKG1; ASCL2; ADCY8; HMMR; PIK3C3; SNTA1; GRIN1; LYST; CALD1; MYO10; MYOG; GRK4; PDE1A; FER; MIP; KCNN2; GAP43; CALCR; AKAP5; RALB; IQGAP1; YWHAE; ADCYAP1R1; CLTB; STRN4; CAMKK2; MYF6; REL; CABIN1; TRPV4; LTF; PPEF1; CNGA2; CSNK2A2; OBSCN; ESR2; FAS; RGS10; KCNQ3; OPRM1; RIT2; MYLK; MYF5; KCNN4; TRPV1; KCNQ5; CCNE1; NEUROD1; CNN1; HSP9OAA1; CAMKK1; RGS4; GRK1; PPEF2; MYO7A; TNNI2; ESRRG; RAB3B; TCF3; ESR1; SYT1; PCP4; CCND1; PTPRA; PLCD1; STRN; CAMK2G; TCF4; TTN; DLG1; PCNT; IQCB1; LOC340357; AKAP9; TCF1; PPYR1; RIOK3; GH1; HLA-C; IKBKE; CAMK2A; CACNA1C; EIF1B; DIRAS2; SH2B3; ITGB5; AR; SMAD3; FBLIM1; BRCA2; NPHP1; KIF3A; MAP2K4; FLNB; PTMAP7; TRIO; MAP3K3; TNIP2; KCNJ2; CMIP; RAC1; MAP3K7IP2; MAP3K7; MYOT; YWHAG; TNFRSF1B; PSEN2; SMAD5; MAPK14; IKBKG; SUMO4; ATN1; BPGM; TBK1; PDIA2; RIPK2; PRKCI; TRAF1; HTATIP; LOC400604; MYOC; PGK1; MCC; PLD2; ATXN1; F1141278; LOC154092; LTB4R; TTC1; CNR2; OPRK1; IL8RA; HRH4; PTPRU; NGB; GPSM2; RGS5; RIC8A; TSHR; SCN8A; KLHL3; EDGE; RGS16; FFAR2; NUCB1; RGS14; EDG3; GALR2; RIC8B; HTR6; TUB; HTR2B; SLC9A3R1; EDGS; FFAR1; KDR; AKAP13; RGS18; PLCB2; RGS13; KIAA1549; C1orf128; KCNH2; HSPA4; TOMM20; LOC285147; ANXA6; GC; AHCYL1; EPB41L1; STARD13; CABP1; TRPC4; BANK1; ITPR3; MRVI1; CDC2; ARHGAP1; FKBP1A; DVL1; DVL3; LXN; CTNNB1; SGOL2; SGOL1; POLB; KCNE4; SEMG2; TRIM29; ARHGEF1; ADCYS; PPARA; XK; AFAP1; AVPR1A; GABRR2; DLG4; GNA12; STXBP3; OGG1; ANXA7; TIAM1; SDPR; PDLIM7; TEP1; TERT; HAND2; SEMG1; CISH; YWHAZ; ITGB4; C1QBP; PDPK1; CASP8; FRS2; PAWR; FEZ2; NFATC2; IRS4; PRG2; FEZ1; JAK1; CASP6; DAPK3; SQSTM1; MAP2K5; MAP2K1; PARD6A; FADD; PARD6B; CASP7; TRAF6; PARD6G; GRB14; IRAK1; IL4R; NF2; ULK1; RNF11; EPHB2; IGSF4; NFASC; SDCBP2; TGFA; B4GALT1; VAV1; MAP1A; PLK1; RAB8B; RACGAP1; ENO2; MAP1LC3A; VDAC1; HDAC6; C4orf17; RTN4; SIRT2; RBM23; S100A8; ACTN2; RPL12; TAOK2; BRCA1; CKAP1; MAGED1; C5orf25; PFDN4; TBCE; HSPH1; DPYSL2; EPB41; NCALD; BCAR1; LGALS2; TM4SF1; RELB; MAP3K7IP1; MAP3K8; NFKB2; RIPK1; TANK; NFKBIE; CHUK; PFDN5; TRADD; TNFRSF1A; NFKBIB; PAFAH1B1; ARL3; C20orf24; MLF2; TNFRSF14; BRF2; PTP4A3; HSPA1B; PELO; ABI3; TANC1; DNM3; TRPC1; GFI1B; FXN; COIL; ARF1; LOC147004; GFI1; ATXN7; ARF3; ATXN3; USP7; SNAP91; PTP4A1; NCOR2; MYT1L; CLU; HARS; ANK2; DST; SPTBN1; PPP1R13B; CNKSR2; LOC100133669; TRIM2; LOC613126; SRGAP3; PDE4DIP; PSMA2; PSMD2; COX17; HLA-DQA2; STX5; CPE; CHD3; DDIT4; SELENBP1; CKMT2; HMOX2; FXR1; MLLT3; KLHL20; TRBV21-1; NP; MAD2L1BP; MNAT1; SPG7; RPL37A; HMP19; BMI1; SAT1; AKR1C3; UBE2V2; PFDN1; ETHE1; GSTM4; ATP1B1; ITGB3BP; BRMS1; PSG9; VIM; WDR62; ANKRD24; BOC; HSPB1; LOC339290; NHP2L1; PFN1; RIT1; HSPB3; KIAA1377; CETN3; RHOH; HSPBP1; RAB27A; KLK10; CRADD; ATF3; PIAS4; HSPE1; PSPC1; NRBP1; C1orf42; NACA; BRD7; TSPAN6; PQBP1; MRPS6; SMPD3; SMN2; CCDC106; PABPC4; CBX1; RBM5; MRPS12; ZNF24; POLR3F; DEFB1; RFC5; LOC93444; TDGF1; PREI3; RNF10; TMSB4X; MPHOSPH6; PLEKHA4; SULT1E1; POLR2C; CDKN2C; DNMT2; PAEP; SNURF; PTPRS; RASSF1; ARL8B; CRIPT; MAP6; MAP3K10; TTK; BMPR2; SYT9; TTBK1; TBCD; RABAC1; FLJ31945; and C20orf20.

Example IV

Biological effects of a GRM5 CNV (deletion) identified in a family of ADHD patients carrying a large deletion in one copy of their GRM5 genes, was examined in PBMC derived cell lines transformed by Epstein-Barr virus (EBV). It is reported in the literature that PBMC cells express both mGluR1 and mGluR5 and the mGluRs may play a role in T cell activation. We first examined expression of mGluR5 in EBV transformed cell lines derived from healthy subjects by qRT-PCR and flow cytometry. The results confirmed the expression of mGluR5. We then compared four cell lines derived from the ADHD family with four control cell lines by quantitative analysis of fluorescent signal in flow cytometry. The ratio of fluorescence value between the mGluR5 Ab staining and the control Ab staining was calculated. The mean ratio of the ADHD group was 4.6 (±0.4), whereas the mean of the control was 7.3 (±1.7). The difference is statistically significant (t-test, p=0.024), representing about 36% reduction of mGluR5 expression in the deleted cases. This result provides the first evidence that this CNV in GRM5 gene results in reduction of mGluR5 expression.

The following materials and methods are provided to facilitate the practice of Example IV.

qRT-PCR.

TaqMan probe and primers were purchased from Applied Biosystems (Cat# Hs00168275-m1). Real-time PCR was performed in 384 well plates by using 7900HTreal-time PCR system (Applied Biosystems). Templates were cDNA synthesized from total RNA and random primer by using the RT cDNA synthesis kit (Applied Biosystems, Cat#4374867). RNA was isolated from the cells cultured in RPMI 1640 media containing 10% FBS.

Flow Cytometry.

Cells were fixed with paraformaldehyde and stained with specific mGluR5 monoclonal antibody (R&D, Cat# MAB4514) or isotype matched control antibody (R&D, Cat# MAB002) followed by phycoerythrin-conjugated anti-mouse antibody. Stained cells were analyzed by using BD FACS Calibur flow cytometer.

Results

Cells of each subject were divided into three samples. One of them was used as background control with staining, and two of them were stained by mGluR5 Ab and control Ab, respectively. The mean fluorescence of cells stained with mGluR5 Ab and control Ab for each subject is listed in Table A. Ratio of the mGluR Ab staining and control Ab staining was calculated and presented in Table 1 too. The mean ratio of the ADHD group was 4.6 (±0.4), whereas the mean of the control was 7.3 (±1.7). The difference is statistically significant (t-test, p=0.024), representing about 36% reduction of mGluR5 expression.

These data show that biological consequences of CNVs in the various gene targets provided herein can be experimentally determined and verified in biological systems thereby facilitating the identification and characterization of beneficial therapeutic agents which can for example restore the biological activity that is lost as a result of these deletions.

TABLE A

Results of flow cytometry analysis of PBMC derived cell lines

| Subject | Fluorescence | | Ratio |
| --- | --- | --- | --- |
| | mGluR5 Ab | Control Ab | |
| ADHD-1 | 52.8 | 11.3 | 4.7 |
| ADHD-2 | 50.8 | 11.2 | 4.5 |
| ADHD-3 | 79.8 | 15.4 | 5.2 |
| ADHD-4 | 56.5 | 13.3 | 4.2 |
| Control-1 | 120 | 19.3 | 6.2 |
| Control-2 | 92 | 13.3 | 6.9 |

TABLE A-continued

Results of flow cytometry analysis of PBMC derived cell lines

| Subject | Fluorescence | | Ratio |
| --- | --- | --- | --- |
| | mGluR5 Ab | Control Ab | |
| Control-3 | 56.7 | 9.01 | 6.3 |
| Control-4 | 116 | 11.7 | 9.9 |

REFERENCES

1. Glessner J T, Wang K, Cai G, et al. Autism genome-wide copy number variation reveals ubiquitin and neuronal genes. Nature 2009; 459:569-573.
2. Derks E M, Hudziak J J, Dolan C V, van Beijsterveldt T C, Verhulst F C, Boomsma D I. Genetic and environmental influences on the relation between attention problems and attention deficit hyperactivity disorder. Behav Genet 38(1), 11-23 (2008).
3. Wood A C, Rijsdijk F, Saudino K J, Asherson P, Kuntsi J. High heritability for a composite index of children's activity level measures. Behav Genet 38(3), 266-276 (2008).
4. Haberstick B C, Timberlake D, Hopfer C J, Lessem J M, Ehringer M A, Hewitt J K. Genetic and environmental contributions to retrospectively reported DSM-IV childhood attention deficit hyperactivity disorder. Psychol Med 38, 1057-1066 (2008).
5. Wang K, Zhang H, Ma D, et al., Common genetic variants on 5p14.1 associate with autism spectrum disorders. Nature 459, 528-533 (2009).
6. Franke B, Neale B M, Faraone S V, Genome-wide association studies in ADHD. Hum Genet. doi: 10.1007/s00439-009-0663-4 (2009).
7. Neale B M, Lasky-Su J, Anney R, et al. Genome-wide association scan of attention deficit hyperactivity disorder. Am J Med Genet B Neuropsychiatr Genet 147B, 1337-1344. (2008).
8. Lasky-Su J, Neale B M, Franke B et al., Genome-wide association scan of quantitative traits for attention deficit hyperactivity disorder identifies novel associations and confirms candidate gene associations. American Journal of Medical Genetics Part B: Neuropsychiatric Genetics 147B(8), 1345-1354 (2008).
9. Lesch K P, Timmesfeld N, Renner T J, et al. Molecular genetics of adult ADHD: converging evidence from genome-wide association and extended pedigree linkage studies. J Neural Transm 115, 1573-1585 (2008).
10. Wang K, Li M, Hadley D, et al. PennCNV: an integrated hidden Markov model designed for high-resolution copy number variation detection in whole-genome SNP genotyping data. Genome Res. 17, 1665-1674 (2007).
11. Zhou K, Dempfle A, Arcos-Burgos M et al. Meta-analysis of genome-wide linkage scans of attention deficit hyperactivity disorder. Am J Med Genet B Neuropsychiatr Genet. 147B(8), 1392-8 (2008).
12. Kent W J, Sugnet C W, Furey T S, et al. The human genome browser at UCSC. Genome Res. 12(6), 996-1006 (2002).
13. Elia, J., Gai, X., et. al. Rare Structural Variants found in Attention-Deficit Hyperactivity Disorder are Preferentially Associated with Neurodevelopmental Genes. Molecular Psychiatry Jun. 23 2009 Epub.
14. Taniura, H., Sanada, N., Kuramoto, N., Yoneda, Y. Metabotropic Glutamate Receptor Family Gene in Dictyostelium discoideum. J. Biol. Chem., 281(18), 12336-12343, (2006).

15. Conn, P. J. & Pin, J. Phamacology and Functions of Metabotropic Glutamate Receptors. Annu. Rev. Pharmacol. Toxicol. 37, 205-37 (1997).
16. Berthele A, Platzer S, Laurie D J, et al. Expression of metabotropic glutamate receptor subtype mRNA (mGluR1-8) in human cerebellum. NeuroReport 10(18), 3861-3867 (1999).
17. Koob, G. F., Sanna, P P, Bloom, F. E., Neuroscience of Addiction. Neuron, 21, 467-476, (1998).
18. Cryan J F, Kelly P H, Neijt H C, Sansig G, Flor P J, van Der Putten H. Antidepressant and anxiolytic-like effects in mice lacking the group III metabotropic glutamate receptor mGluR7. European Journal of Neuroscience. 17(11):2409-2417, (2003).
19. Makoff, A., Pillinga, C, Harrington, K., Emson, P. Human metabotropic glutamate receptor type 7: Molecular cloning and mRNA distribution in the CNS. Molecular Brain Research. 40(1), 165-170 (1996).
20. Turic D, Langley K, Mills S, et al. Follow-up of genetic linkage findings on chromosome 16p13: evidence of association of N-methyl-D aspartate glutamate receptor 2A gene polymorphism with ADHD. Mol Psychiatry 9, 169-173 (2004).
21. Mick, E. and Faraone, S. V., Genetics of attention deficit hyperactivity disorder. Child Adolesc Psychiatr Clin N Am 17, 261-284, vii-viii. (2008).
22. Turic D, Langley K, Williams H, et al. A family based study implicates solute carrier family 1-member 3 (SLC1A3) gene in attention-deficit/hyperactivity disorder. Biol Psychiatry 2005 Jun. 1; 57(11):1461-6.
23. Elia J, Capasso M, Zaheer Z, et al. Candidate gene analysis in an on-going genome-wide association study of attention-deficit hyperactivity disorder: suggestive association signals in ADRA1A. Psychiatr Genet. PMID: 19352218 (2009).
24. Mick E, Neale B, Middleton F A, McGough J J, Faraone S V. Genome-wide association study of response to methylphenidate in 187 children with attention-deficit/hyperactivity disorder. Am J Med Genet B Neuropsychiatr Genet 147B, 1412-1418 (2008).
25. Dorval K M, Wigg K G, Crosbie J, et al., Association of the glutamate receptor subunit gene GRIN2B with attention-deficit/hyperactivity disorder. Genes Brain Behav. 6(5) (2007).
26. Jin Z, Zang Y F, Zeng Y W, Zhang L, Wang Y F. Striatal neuronal loss or dysfunction and choline rise in children with attention-deficit hyperactivity disorder: a 1H-magnetic resonance spectroscopy study. Neurosci Lett 315, 45-48 (2001).
27. MacMaster F P, Caney N. Sparkes S, Kusumakar V Proton spectroscopy in medication-free pediatric attention-deficit/hyperactivity disorder. Biol Psychiatry 53:184-187. (2003).
28. Courvoisie H, Hooper S R, Fine C, Kwock L, Castillo M. Neurometabolic functioning and neuropsychological correlates in children with ADHD-H: preliminary findings. J Neuropsychiatry Clin Neurosci 16, 63-69 (2004).
29. Caney N, MacMaster F P, Fogel J, et al. Metabolite changes resulting from treatment in children with ADHD: a 1H-MRS study. Clin Neuropharmacol 26, 218-221 (2003).
30. Gainetdinov R R, Wetsel W C, Jones S R, Levin E D, Jaber M, Caron M G. Role of serotonin in the paradoxical calming effect of psychostimulants on hyperactivity. Science 283, 397-401 (1999).
31. Gainetdinov, R. R., Mohn, A. R., Bohn, L. M., Caron, M. G. Glutamatergic modulation of hyperactivity in mice lacking the dopamine transporter. Proc Natl Acad Sci USA 98, 11047-11054 (2001).
32. Masuo, Y. Ishido, M., Morita, M., Oka, S. Effects of neonatal 6-hydroxydopamine lesion on the gene expression profile in young adult rats. Neurosci Lett 335, 124-128 (2002).
33. Miyamoto K, Nakanishi H, Moriguchi S, et al. Involvement of enhanced sensitivity of N-methyl-D-aspartate receptors in vulnerability of developing cortical neurons to methylmercury neurotoxicity. Brain Res 901, 252-258 (2001).
34. Russell V, Allie S, Wiggins T. Increased noradrenergic activity in prefrontal cortex slices of an animal model for attention-deficit hyperactivity disorder—the spontaneously hypertensive rat. Behav Brain Res 117, 69-74 (2000).
35. Russell V A. Dopamine hypofunction possibly results from a defect in glutamate-stimulated release of dopamine in the nucleus accumbens shell of a rat model for attention deficit hyperactivity disorder—the spontaneously hypertensive rat. Neurosci Biobehav Rev 27, 671-682 (2003).
36. DasBanerjee T, Middleton F A, Berger D F, Lombardo J P, Sagvolden T, Faraone S V. A comparison of molecular alterations in environmental and genetic rat models of ADHD: a pilot study. Am J Med Genet B Neuropsychiatr Genet 147B, 1554-63 (2008).
37. Sagvolden T, Johansen E B, Wøien G, et al. The spontaneously hypertensive rat model of ADHD—the importance of selecting the appropriate reference strain. Neuropharmacology 57, 619-26 (2009).
38. Del Bo R, Ghezzi S, Corti S, et. al., DPP6 gene variability confers increased risk of developing sporadic amyotrophic lateral sclerosis in Italian patients. Journal of Neurology, Neurosurgery & Psychiatry 79(9), 1085 (2008).
39. Cronin S, Tomik B, Bradley D G, Slowik A, Hardiman O Screening for replication of genome-wide SNP associations in sporadic ALS. European Journal of Human Genetics 17, 213-218 (2009).
40. Marshall C R, Noor A, Vincent J B, et al. Structural variation of chromosomes in autism spectrum disorder. Am. J. Hum. Genet. 82, 477-88 (2008).
41. Renström F, Payne F, Nordstrom A, et al. Replication and extension of genome-wide association study results for obesity in 4923 adults from northern Sweden Human Molecular Genetics 18(8):1489-1496 (2009).
42. Kessler R C, Adler L A, Barkley R, et al., Patterns and predictors of attention-deficit/hyperactivity disorder persistence into adulthood: results from the national comorbidity survey replication. Biological Psychiatry 57(11), 1442-1451 (2005).
43. Diskin S, Li M, Hou C, et al., Adjustment of genomic waves in signal intensities from whole-genome SNP genotyping platforms. Nucleic Acids Research. 36(19) (2008).
44. Dennis G Jr, Sherman B T, Hosack D A, et al., DAVID: Database for Annotation, Visualization, and Integrated Discovery. Genome Biology. 4(9), (2003).
45. Lesch K P, Selch S, Renner T J, et al. Genome-wide copy number variation analysis in ADHD: association with neuropeptide Y gene dosage in an extended pedigree. Mol Psychiatry, Epub ahead of print (2010).
46. Oades R D, Daniels R, Rancher W. Plasma neuropeptide Y levels, monoamine metabolism, electrolyte excretion, and drinking behavior in children with attention-deficit hyperactivity-disorder (ADHD). Psychiat Res., 80, 77-186. (1998).

47. Shannon P, Markiel A, Ozier O, Baliga N S, Wang J T, Ramage D, Amin N, Schwikowski B, Ideker T. Cytoscape: a software environment for integrated models of biomolecular interaction networks. Genome Res. 2003 November; 13(11):2498-504.
48. Potkin S G, Turner J A, Guffanti G, Lakatos A, Fallon J H, Nguyen D D, Mathalon D, Ford J, Lauriello J, Macciardi F; FBIRN. A genome-wide association study of schizophrenia using brain activation as a quantitative phenotype. Schizophr Bull. 2009 January; 35(1):96-108. Epub 2008 Nov. 20.
49. Wang X, Bao X, Pal R, Agbas A, Michaelis E K. Transcriptomic responses in mouse brain exposed to chronic excess of the neurotransmitter glutamate. BMC Genomics. 2010 Jun. 7; 11:360.
50. C. de Lanerolle, Nihal; Eid, Tore; Lee, Tih-Shih. Genomic Expression in the Epileptogenic Hippocampus and Psychiatric Co-Morbidities. Current Psychiatry Reviews, Volume 6, Number 2, May 2010, pp. 135-144 (10).
51. Ule, J., Stefani, G., Mele, A., Ruggiu, M., Wang, X., Taneri, B., et al. (2006). An RNA map predicting Nova-dependent splicing regulation. Nature, 444(7119), 580-6. doi: 10.1038/nature05304.
52. Ule, J., Ule, A., Spencer, J., Williams, A., Hu, J., Cline, M., et al. (2005). Nova regulates brain-specific splicing to shape the synapse. Nature genetics, 37(8), 844-52. doi: 10.1038/ng1610.
53. Murias, M., Swanson, J. M., & Srinivasan, R. (2007). Functional connectivity of frontal cortex in healthy and ADHD children reflected in EEG coherence. Cerebral cortex (New York, N.Y.: 1991), 17(8), 1788-99. doi: 10.1093/cercor/bh1089.
54. Wang, L., Zhu, C., He, Y., Zang, Y., Cao, Q., Zhang, H., et al. (2009). Altered small-world brain functional networks in children with attention-deficit/hyperactivity disorder Human brain mapping, 30(2), 638-49. doi: 10.1002/hbm.20530.

While certain of the preferred embodiments of the present invention have been described and specifically exemplified above, it is not intended that the invention be limited to such embodiments. It will be apparent to one skilled in the art that various changes and modifications can be made therein without departing from the scope of the present invention, as set forth in the following claims.

What is claimed is:
1. A method for treating attention deficit hyperactivity disorder (ADHD) in a human subject with at least one ADHD-associated copy number variation (CNV), comprising testing said sample for the presence of each of the following CNVs
(1)
a) a CNV that comprises a deletion in GRM5 gene sequences between rs604179 and rs669724 in the physical chromosome range chr11:88269449-88351661 and rs694665;
b) a CNV that comprises a deletion in GRM8 gene sequences between rs7794734 and rs2237790 in the physical chromosome range chr7:126525124-126536202, and rs6975798;
c) a CNV that comprises a deletion in GRM7 gene sequences between rs1516302 and rs6784317 in the physical chromosome range chr3:7183953-7197236, and rs10866078;
d) a CNV that comprises a deletion in SGTB/NLN gene sequences between rs10073281 and rs972501 in the physical chromosome range chr5:65027976-65046520, and rs17590975;
e) a CNV that comprises a deletion in USP24 gene sequences between rs7527177 and rs4333889 in the physical chromosome range chr1:56053497-56064495, and rs4512692;
f) a CNV that comprises a deletion in SLC7A10 gene sequences between rs748680 and rs4530278 in the physical chromosome range chr19:38427720-38444834, and rs7256230;
g) a CNV that comprises a duplication in GRM1 gene sequences between rs12200797 and rs362949 in the physical chromosome range chr6:146657076-146694047, and rs1009085;
h) a CNV comprising a duplication in NEGR1 gene sequences between rs12033161 and rs2821257 in the physical chromosome range chr1:72317292-72328395, and rs2821267;
i) a CNV comprising a duplication in DPP6 gene sequences between rs4389846 and rs12703329 in the physical chromosome range chr7:153495598-153564827, and rs12703323;
j) a CNV comprising a duplication in CNTN4 gene sequences between rs10510218 and rs7625240 in the physical chromosome range chr3:1844168-1859889, and rs17044355 and;
k) a CNV comprising a duplication in LARP7 gene sequences between rs12054518 and rs7690429 in the physical chromosome range chr4: 113772340-113788584, and rs6533635; wherein said chromosomal ranges in each of steps a)-k) are provided in build 36/hg18; wherein the presence of
at least one ADHD-associated CNV in the sample indicates ADHD in the subject; and
(2) administering an effective amount of (+)-5-oxo-D-prolinepiperidinamide,

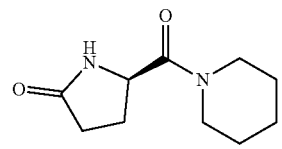 [SMILES: O=C1CC[C@H](C(=O)N2CCCCC2)N1]

and/or at least one pharmaceutically acceptable acid addition salt and/or solvate thereof to a subject having the at least one ADHD-associated CNV wherein said CNV is 1 kB or larger.
2. The method of claim 1, wherein the ADHD-associated CNV is detected by measuring the intensity of one or more detectably labeled nucleic acids harboring single nucleotide polymorphisms (SNPs) located within the CNV, and comparing the measured intensity to the intensity of detectably labeled nucleic acids harboring SNPs of control subjects.
3. The method of claim 1, comprising measuring the intensity of detectably labeled single nucleotide polymorphisms (SNPs) located within the CNV and any one or more of the following snps, and comparing the measured intensity to the intensity of detectably labeled SNPs found in control subjects:
a) GRM5 snps: rs506811, rs604179, rs1954979, rs693008, rs594561, rs585423, rs2047507, rs598758, rs547644, rs316090, rs656544, rs641052, rs11021670, cnvi0116228, rs541046, rs475872, rs694665, rs573912, rs563371, rs533163, rs5027960, rs644170, rs675010, cnvi0050221, rs518167, rs591849, rs655683, rs597462, rs539752, rs477399, rs597303, rs669724, rs677526;
b) GRM8 snps: rs10954144, rs7794734, rs12375090, rs6975798, rs1557644, rs12706778, rs2237790, rs11563719;
c) GRM7 snps: rs9864350, rs1516302, rs1400163, rs965170, rs11131064, rs10866078, rs1400166, rs17235039, rs10510351, rs11715681, rs6784317, rs1963265;
d) GRM1 snps: rs6570746, rs12200797, rs1555084, rs1009085, rs362962, rs362949, rs362835;
e) NEGR1 snps: rs2821267, rs12033161, rs988421, rs2821255, rs2821257, rs10493493;
f) DPP6 snps: rs3115157, rs4389846, rs4131646, rs7790046, rs7794112, rs12532924, rs4452722, rs11975478, rs11976255, rs10280963, rs4507681, rs6955717, rs7811481, rs6945869, rs4074568, rs4074817, rs4726385, rs4380850, rs12703323, rs9791911, rs4397308, rs10224365, rs10267846, cnvi0096121, cnvi0096122, cnvi0096123, cnvi0096124, cnvi0096125, cnvi0096126, rs10952466, cnvi0096127, rs10952467, cnvi0096128, cnvi0096129, rs10272007, cnvi0096130, cnvi0096131, cnvi0096132, rs4726389, rs12674128, rs10254647, rs12703329, rs12668613;
g) SGTB/NLN snps: rs112314, rs10073281, rs17590975, rs972501, rs252646;
h) USP24 snps: rs4367814, rs7527177, rs10888939, rs4512692, rs6588574, rs4333889, rs10493190;
i) SLC7A10 snps: rs752503, rs748680, rs7256230, rs10500264, rs4530278, rs736289;
j) CNTN4 snps: rs9825865, rs10510218, rs12488941, rs9860556, rs17044355, rs13322503, rs6781373, rs7625240, rs1387084;
k) LARP7 snps: rs1565010, rs12054518, rs1129065, rs4834296, rs4409021, cnvi0018439, rs4488992, rs6533635, rs11722959, rs4555714, rs11946967, rs2352050, rs10031435, rs7690429, rs4834302.

4. The method of claim 1, wherein the (+)-5-oxo-D-prolinepiperidinamide and/or at least one pharmaceutically acceptable acid addition salt and/or solvate thereof is (+)-5-oxo-D-prolinepiperidinamide monohydrate

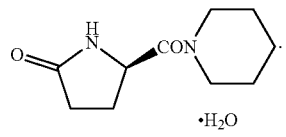

5. The method of claim 2, wherein said detectable label is a fluorescent label.

* * * * *